US011566249B2

(12) United States Patent
Akai

(10) Patent No.: US 11,566,249 B2
(45) Date of Patent: Jan. 31, 2023

(54) DNA FRAGMENT, RECOMBINANT VECTOR, TRANSFORMANT, AND NITROGEN FIXATION ENZYME

(71) Applicant: TOYOTA BOSHOKU KABUSHIKI KAISHA, Aichi-ken (JP)

(72) Inventor: Masaro Akai, Aichi-ken (JP)

(73) Assignee: TOYOTA BOSHOKU KABUSHIKI KAISHA, Aichi-Ken (JP)

( * ) Notice: Subject to any disclaimer, the term of this patent is extended or adjusted under 35 U.S.C. 154(b) by 15 days.

(21) Appl. No.: 16/965,838

(22) PCT Filed: Jan. 11, 2019

(86) PCT No.: PCT/JP2019/000707

§ 371 (c)(1),
(2) Date: Jul. 29, 2020

(87) PCT Pub. No.: WO2019/150919

PCT Pub. Date: Aug. 8, 2019

(65) Prior Publication Data

US 2021/0054385 A1 Feb. 25, 2021

(30) Foreign Application Priority Data

Jan. 30, 2018 (JP) ............................ JP2018-014185

(51) Int. Cl.
*C12N 15/74* (2006.01)
*C12N 9/02* (2006.01)

(52) U.S. Cl.
CPC ........... *C12N 15/74* (2013.01); *C12N 9/0004* (2013.01)

(58) Field of Classification Search
CPC ........ C12N 9/0004; C12N 15/70; C12N 5/10; C12N 15/74
See application file for complete search history.

(56) References Cited

FOREIGN PATENT DOCUMENTS

| | | | |
|---|---|---|---|
| JP | 2007-159417 | A | 6/2007 |
| JP | 2014-003920 | A | 1/2014 |
| JP | 2016-136972 | A | 8/2016 |
| WO | 2012/111810 | A1 | 8/2012 |

OTHER PUBLICATIONS

Welsh et al. The genome of Cyanothece 51142, a unicellular diazotrophic cyanobacterium important in the marine nitrogen cycle. PNAS (2008), 105(39): 15094-15099.*

Whisstock et al. Quaterly Reviews of Biophysics, 2003, "Prediction of protein function from protein sequence and structure", 36(3):307-340.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Magrini et al. Fosmid-Based Physical Mapping of the Histoplasma capsulatum Genome. Genome Research (2004), 14:1603-1609.*

Thiel, "Characterization of Genes for an Alternative Nitrogenase in the Cyanobacterium *Anabaena variabilis", Journal of Bacteriology*, vol. 175, No. 19, pp. 6276-6286 (1993).

Welsh et al., "The Genome of *Cyanothece* 51142, a Unicellular Diazotrophic Cyanobacterium Important in the Marine Nitrogen Cycle", *Proceedings of the National Academy of Sciences*, vol. 105, No. 39, pp. 15094-15099 (2008).

International Search Report issued in PCT/JP2019/000707, dated Mar. 12, 2019, along with an English language translation.

International Preliminary Report on Patentability issued in PCT/JP2019/000707, dated Aug. 13, 2020.

Office Action issued in JP Patent Application No. 2019-568969, dated Jul. 5, 2022, translation.

* cited by examiner

*Primary Examiner* — Iqbal H Chowdhury

(74) *Attorney, Agent, or Firm* — Greenblum & Bernstein, P.L.C.

(57) ABSTRACT

A DNA fragment to encode a nitrogen fixation enzyme includes a base sequence of SEQ ID NO:1 or a base sequence having not less than 50% identity with the SEQ ID NO:1.

8 Claims, 3 Drawing Sheets

Specification includes a Sequence Listing.

DNA FRAGMENT, RECOMBINANT VECTOR, TRANSFORMANT, AND NITROGEN FIXATION ENZYME

SEQUENCE LISTING

The instant application contains a Sequence Listing which has been submitted electronically in ASCII format and is hereby incorporated by reference in its entirety. Said ASCII copy, created on May 7, 2022, is named P60687_SL.txt and is 151,502 bytes in size.

TECHNICAL FIELD

The present invention relates to a DNA fragment encoding a nitrogen fixation enzyme, a recombinant vector containing the DNA fragment, a transformant transformed by the recombinant vector, and a nitrogen fixation enzyme.

BACKGROUND ART

In general, *Escherichia coli* is inhibited from growing in a media without any nitrogen source (ammonium chloride, sodium nitrate, etc.) and it is thus necessary to add a nitrogen source to media for its multiplication.

As a nitrogen fixation process other than the conventional Haber-Bosch process, there is an enzymatic process using nitrogenase. In this process, atmospheric nitrogen can be fixed as ammonia in an environment at ordinary temperature and normal pressure. Therefore, in the presence of nitrogenase, it is possible to eliminate the need for the above-mentioned addition of a nitrogen source.

On the other hand, nitrogenase is a metal enzyme containing V or Mo (see, e.g., Patent Literature 1).

CITATION LIST

Patent Literature

Patent Literature 1: JP 2016/136972 A (paragraphs 0006 and 0007)

SUMMARY OF INVENTION

Technical Problem

However, if nitrogen fixation is carried out using *Escherichia coli* with nitrogenase introduced thereinto, a metallic element as an active center, such as V or Mo, is not enough and, therefore, addition of the metallic element such as V or Mo is essentially needed so as to multiple the *Escherichia coli* with nitrogenase introduced thereinto in a medium without any nitrogen source.

It is an object of the invention to provide a DNA fragment which encodes a nitrogen fixation enzyme allowing for elimination of the need for a nitrogen source required to be added to a medium for multiplication of *Escherichia coli*, a recombinant vector containing the DNA fragment, a transformant transformed by the recombinant vector, and the nitrogen fixation enzyme.

It is an another object of the invention to provide a DNA fragment which encodes a nitrogen fixation enzyme allowing for multiplication of *Escherichia coli* without adding a metallic element such as V or Mo to a medium, a recombinant vector containing the DNA fragment, a transformant transformed by the recombinant vector, and the nitrogen fixation enzyme.

Solution to Problem

According to an embodiment of the invention, a DNA fragment, a recombinant vector, a transformant and a nitrogen fixation enzyme defined by [1] to [12] below, are provided. The nitrogen fixation enzyme as used herein means an enzyme which promotes multiplication (growth) of *Escherichia coli* in a medium without any nitrogen source (ammonium chloride, sodium nitrate, etc.).

[1] A DNA fragment to encode a nitrogen fixation enzyme, comprising a base sequence of SEQ ID NO:1 or a base sequence having not less than 50% identity with the SEQ ID NO:1.

[2] The DNA fragment according to [1], wherein the DNA fragment comprising the base sequence of SEQ ID NO:1 is derived from a genomic DNA of cyanobacteria.

[3] A DNA fragment to encode a nitrogen fixation enzyme, comprising any one or more of base sequences of SEQ ID NOs:2 to 33.

[4] The DNA fragment according to [3], wherein the DNA fragment is derived from a genomic DNA of cyanobacteria.

[5] The DNA fragment according to [2] or [4], wherein the cyanobacteria comprises *Cyanothece* sp. ATCC 51142.

[6] A recombinant vector, comprising the DNA fragment according to any one of [1] to [5].

[7] The recombinant vector according to [6], comprising a fosmid vector comprising the DNA fragment incorporated thereto.

[8] A transformant transformed by the recombinant vector according to [6] or [7].

[9] A nitrogen fixation enzyme expressed by the transformant according to [8].

[10] A nitrogen fixation enzyme, comprising a same amino acid sequence as the nitrogen fixation enzyme according to [9], or an amino acid sequence having not less than 40% identity with the amino acid sequence.

[11] The nitrogen fixation enzyme according to [9] or [10], comprising any one or more of amino sequences of SEQ ID NOs: 34 to 65.

[12] A nitrogen fixation enzyme, comprising any one or more of amino sequence of SEQ ID NOs: 34 to 65.

Advantageous Effects of Invention

According to an embodiment of the invention, it is possible to provide a DNA fragment to encode a nitrogen fixation enzyme allowing for elimination of the need for a nitrogen source required to be added to a medium for multiplication of *Escherichia coli*, a recombinant vector containing the DNA fragment, a transformant transformed by the recombinant vector, and the nitrogen fixation enzyme.

Also, according to an embodiment of the invention, it is possible to provide a DNA fragment to encode a nitrogen fixation enzyme allowing for multiplication of *Escherichia coli* without adding a metallic element such as V or Mo to a medium, a recombinant vector containing the DNA fragment, a transformant transformed by the recombinant vector, and the nitrogen fixation enzyme.

DESCRIPTION OF EMBODIMENTS (DNA fragment)

Figure 1:
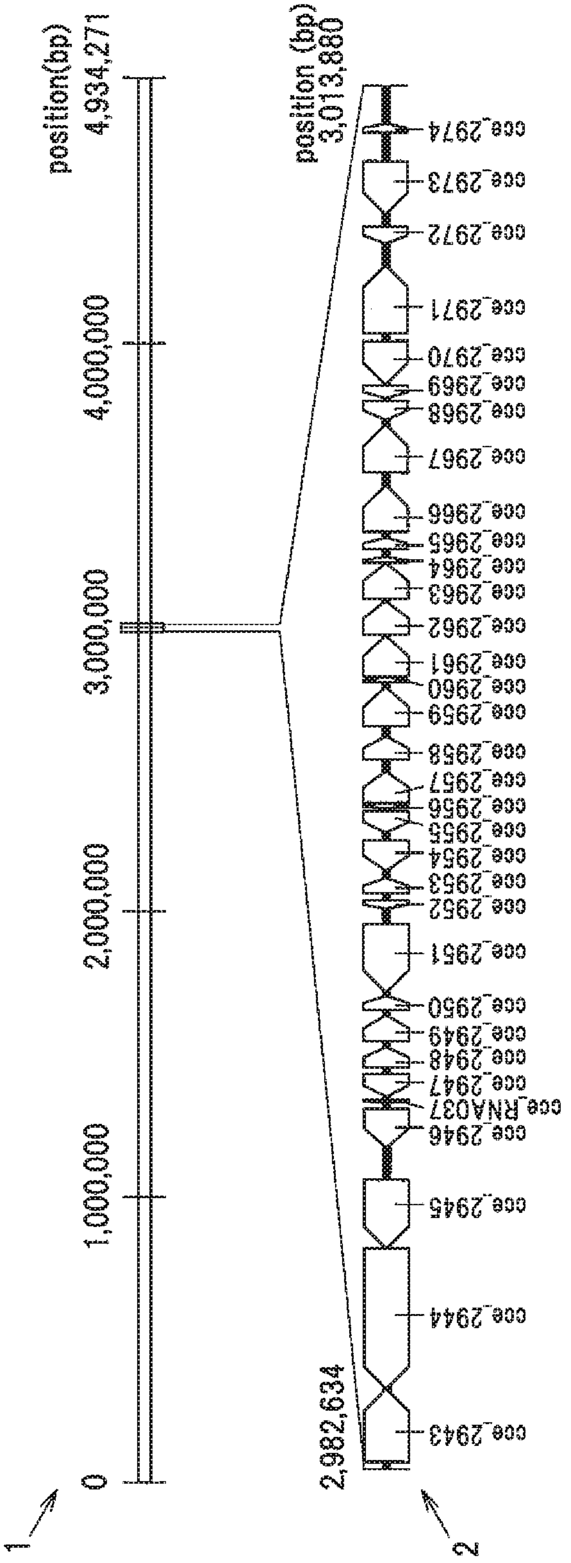
FIG. 1 is an explanatory diagram illustrating a position of a DNA fragment in an embodiment of the present invention in a genomic DNA and thirty-two open reading frames contained in the DNA fragment.

FIG. 1 is an explanatory diagram illustrating a position of a DNA fragment in an embodiment of the invention in a genomic DNA and thirty-two open reading frames contained in the DNA fragment.

A DNA fragment 2 in the embodiment of the invention has a base sequence of SEQ ID NO:1, or a base sequence having not less than 50% identity with the SEQ ID NO:1, which encodes a nitrogen fixation enzyme. In the embodiment of the invention, the nitrogen fixation enzyme means a nitrogen fixation enzyme allowing for elimination of the need for a nitrogen source required to be added to a medium for multiplication of *Escherichia coli*, or a nitrogen fixation enzyme allowing for multiplication of *Escherichia coli* without adding a metallic element required for nitrogenase, such as V or Mo, to a medium. In a more desirable embodiment of the invention, it means a nitrogen fixation enzyme which is active in photosynthetic organisms producing oxygen, such as algae or plants.

The DNA fragment having a base sequence of SEQ ID NO:1 (indicated by the number 2 in FIG. 1) is derived from, e.g., a genomic DNA (indicated by the number 1 in FIG. 1) of cyanobacteria (also called blue-green alga) (a 31247 base sequence, from 2982634$^{th}$ to 3013880$^{th}$). The cyanobacteria is, e.g., *Cyanothece* sp. ATCC 51142. The *Cyanothece* sp. ATCC 51142 can be obtained from, e.g., The American Type Culture Collection (ATCC).

The base sequence encoding the nitrogen fixation enzyme may be a base sequence having not less than 500% identity with the SEQ ID NO:1, and is preferably a base sequence having not less than 60% identity with the SEQ ID NO:1, more preferably a base sequence having not less than 70% identity with the SEQ ID NO:1, further preferably a base sequence having not less than 80% identity with the SEQ ID NO:1, further preferably a base sequence having not less than 90% identity with the SEQ ID NO:1, further preferably a base sequence having not less than 95% identity with the SEQ ID NO:1, and further preferably a base sequence having not less than 98% identity with the SEQ ID NO:1.

The DNA fragment having a base sequence of SEQ ID NO:1 or a base sequence having not less than 50% identity with the SEQ ID NO:1 may be artificially synthesized by a genetic engineering procedure.

The DNA fragment in the embodiment of the invention has any one or more of base sequences of SEQ ID NOs:2 to 33 which encode the nitrogen fixation enzyme. The base sequences of SEQ ID NOs:2 to 33 respectively correspond to open reading frames (Gene ID: from cce_2943 to cce_2974) shown in FIG. 1. The gene ID is defined in, e.g., CyanoBase ([genome.microbedb.jp/cyanobase/]) or KEGG, Kyoto Encyclopedia of Genes and Genomes ([hypertext transfer protocol//www.genome.jp.kegg/]).

The DNA fragment in the embodiment of the invention has preferably not less than 5, more preferably not less than 10, further preferably not less than 15, further preferably not less than 20, further preferably not less than 25, further preferably not less than 28, and further preferably not less than 30 of the base sequences of SEQ ID NOs:2 to 33. The order of the base sequences of SEQ ID NOs:2 to 33 may be changed but is preferably not changed.

The DNA fragment 2 in the embodiment of the invention shown in FIG. 1 has the base sequence of SEQ ID NO:1 and also has all the base sequences of SEQ ID NOs:2 to 33. The DNA fragment 2 in the embodiment of the invention may have a base sequence other than the base sequences of SEQ ID NOs:2 to 33, and may have, e.g., a base sequence of tRNA (Gene ID: cce_RNA037).

The DNA fragment having any one or more of the base sequences of SEQ ID NOs:2 to 33 is derived from, e.g., a genomic DNA of cyanobacteria. The cyanobacteria is, e.g., *Cyanothece* sp. ATCC 51142.

The DNA fragment 2 can be isolated from a cyanobacterial genomic DNA by following the commonly performed operating procedure as described in 1 to 5 below. In more detail, it is possible to isolate according to, e.g., Example which is described later. The procedure of each operation is not specifically limited and various known methods can be employed.

1. Mass culture of Cyanobacteria
2. Extraction and Fragmentation of Genomic DNA of cyanobacteria: As a step of increasing purity of DNA, polysaccharides may be removed after the fragmentation.
3. Cloning
   (1) Modify the ends of DNA fragments
   (2) Sort according to size by electrophoresis (e.g., using a low-melting-point agarose for polymer separation, at 18V for 24 hours)
   (3) Collect DNA fragments of about 25 to 40 kb
   (4) Insert each of the collected DNA fragments into a vector (e.g., a fosmid vector), thereby forming vectors with various DNA fragments (recombinant vectors)
4. Produce Transformant
   (1) The vectors with various DNA fragments are introduced (packaging) into bacteriophages
   (2) Infect Host such as *Escherichia coli* with the bacteriophages in the above (1), thereby obtaining *Escherichia coli* having vectors with various DNA fragments (transformants)
   (3) The transformants are grown in agar media and then obtained as colonies
5. Screening
   (1) Select *Escherichia coli* which can be grown in media not containing any nitrogen source (a nitrogen compound such as ammonium chloride, sodium nitrate)
   (2) Extract the vectors from the *Escherichia coli*
   (3) Decode genetic information of the DNA fragments inserted into the vectors The DNA fragment having any one or more of the base sequences of SEQ ID NOs:2 to 33 may be artificially synthesized by a genetic engineering procedure.

(Recombinant Vector)

Figure 2:
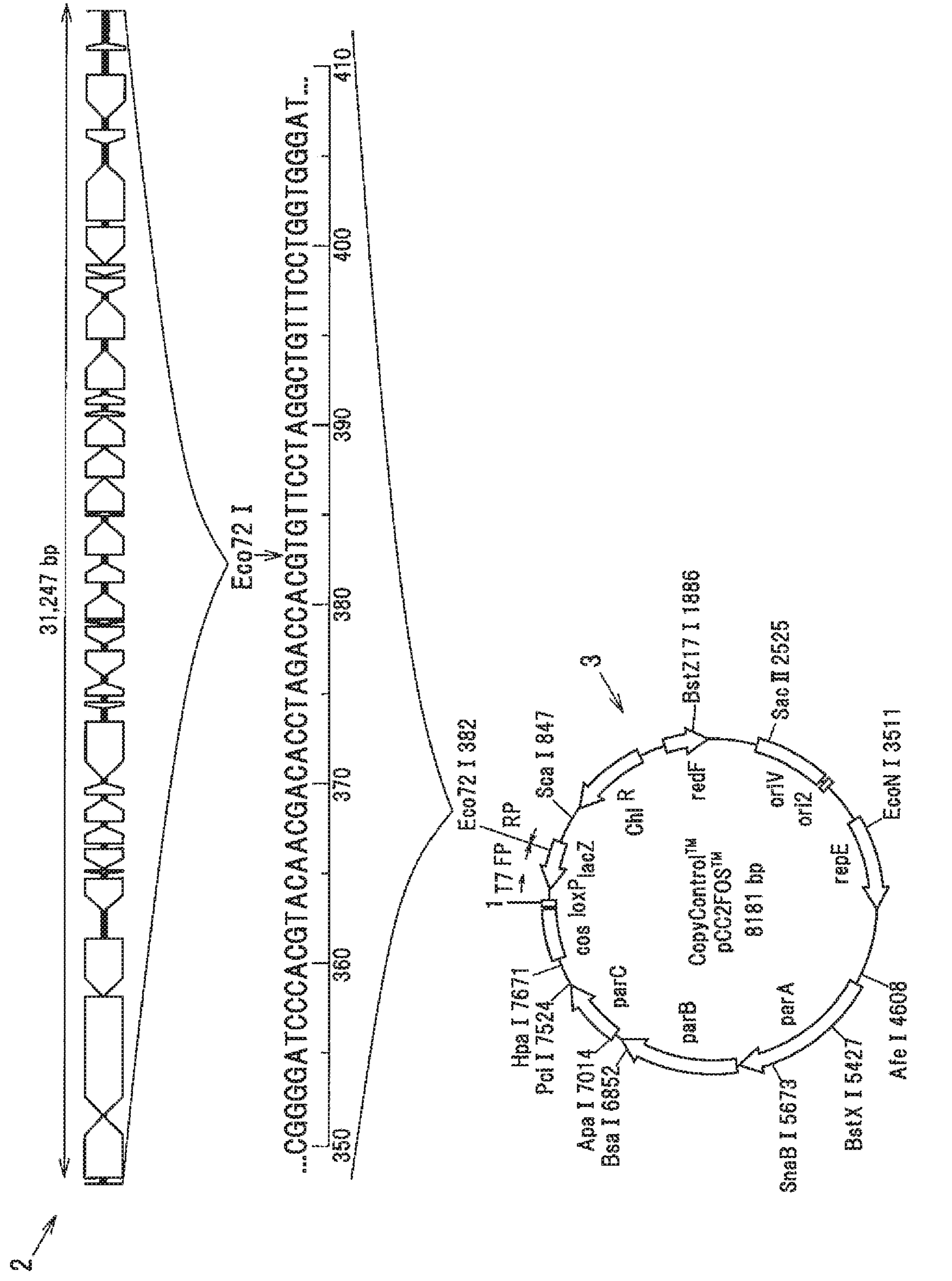
FIG. 2 is an explanatory diagram illustrating a position in a fosmid vector at which the DNA fragment in the embodiment of the invention is incorporated. The polynucleotide sequence shown is SEQ ID NO: 66.

FIG. 2 is an explanatory diagram illustrating a position in a fosmid vector at which the DNA fragment in the embodiment of the invention is incorporated.

A recombinant vector 3 in the embodiment of the invention contains the above-described DNA fragment in the embodiment of the invention. The recombinant vector 3 is preferably obtained by incorporating (inserting) the DNA fragment into a fosmid vector, but it is not limited thereto. It may be obtained by incorporation into, e.g., a plasmid vector, a cosmid vector or a virus vector, etc.

The recombinant vector 3 in the embodiment of the invention can be obtained by following, e.g., the above-mentioned operating procedure for isolating the DNA fragment 2 from the cyanobacterial genomic DNA.

(Transformant)

The transformant in the embodiment of the invention is obtained by transforming a host such as *Escherichia coli* using the above-described recombinant vector in the embodiment of the invention.

The transformant in the embodiment of the invention can be obtained by following, e.g., the above-mentioned operating procedure for isolating the DNA fragment 2 from the cyanobacterial genomic DNA.

(Nitrogen Fixation Enzyme)

The nitrogen fixation enzyme in the embodiment of the invention is expressed by the above-described transformant in the embodiment of the invention. The nitrogen fixation enzyme in the embodiment of the invention preferably has amino sequences of SEQ ID NOs: 34 to 65 which are arranged in this order (with SEQ ID NO: 34 on the left end side and SEQ ID NO: 65 on the right end side) and respectively correspond to the base sequences of SEQ ID NOs:2 to 33 (see Table 1 below; SEQ ID NO:2 corresponds to SEQ ID NO: 34, . . . and SEQ ID NO:33 corresponds to SEQ ID NO: 65). Any one or more of the amino acid sequences of SEQ ID NOs: 34 to 65 may be amino acid sequences in which one or more amino acids are inserted, replaced, deleted and/or added and which encode a nitrogen fixation enzyme functionally equivalent to the above-described nitrogen fixation enzyme (the same applied to the nitrogen fixation enzyme in an another embodiment of the invention described later). In such a nitrogen fixation enzyme, e.g., 1 to 30, preferably 1 to 20, more preferably 1 to 10, further preferably 1 to 5, most preferably 1 to 2 amino acids can be inserted, replaced, deleted and/or added (the same applied to the nitrogen fixation enzyme in an another embodiment of the invention described later).

TABLE 1

| Gene | | | | | | | Gene product | | | | | |
|---|---|---|---|---|---|---|---|---|---|---|---|---|
| Gene ID (CyanoBase-ID) | Type of Sequence | Molecular type | Number of strands | Topology | Length (bp) | SEQ ID NO | Protein ID (NCBI-Protein ID) | Type of Sequence | Molecular type | Topology | Length (aa) | SEQ ID NO |
| cce_2943 | DNA | cDNA | Double-stranded | Linear | 1665 | 2 | ACB52291 | Amino acid | Protein | Linear | 554 | 34 |
| cce_2944 | DNA | cDNA | Double-stranded | Linear | 3198 | 3 | ACB52292 | Amino acid | Protein | Linear | 1065 | 35 |
| cce_2945 | DNA | cDNA | Double-stranded | Linear | 1572 | 4 | ACB52293 | Amino acid | Protein | Linear | 523 | 36 |
| cce_2946 | DNA | cDNA | Double-stranded | Linear | 885 | 5 | ACB52294 | Amino acid | Protein | Linear | 294 | 37 |
| cce_2947 | DNA | cDNA | Double-stranded | Linear | 525 | 6 | ACB52295 | Amino acid | Protein | Linear | 174 | 38 |
| cce_2948 | DNA | cDNA | Double-stranded | Linear | 465 | 7 | ACB52296 | Amino acid | Protein | Linear | 154 | 39 |
| cce_2949 | DNA | cDNA | Double-stranded | Linear | 600 | 8 | ACB52297 | Amino acid | Protein | Linear | 199 | 40 |
| cce_2950 | DNA | cDNA | Double-stranded | Linear | 321 | 9 | ACB52298 | Amino acid | Protein | Linear | 106 | 41 |
| cce_2951 | DNA | cDNA | Double-stranded | Linear | 1566 | 10 | ACB52299 | Amino acid | Protein | Linear | 521 | 42 |
| cce_2952 | DNA | cDNA | Double-stranded | Linear | 183 | 11 | ACB52300 | Amino acid | Protein | Linear | 60 | 43 |
| cce_2953 | DNA | cDNA | Double-stranded | Linear | 345 | 12 | ACB52301 | Amino acid | Protein | Linear | 114 | 44 |
| cce_2954 | DNA | cDNA | Double-stranded | Linear | 702 | 13 | ACB52302 | Amino acid | Protein | Linear | 233 | 45 |
| cce_2955 | DNA | cDNA | Double-stranded | Linear | 486 | 14 | ACB52303 | Amino acid | Protein | Linear | 161 | 46 |
| cce_2956 | DNA | cDNA | Double-stranded | Linear | 96 | 15 | ACB52304 | Amino acid | Protein | Linear | 31 | 47 |
| cce_2957 | DNA | cDNA | Double-stranded | Linear | 714 | 16 | ACB52305 | Amino acid | Protein | Linear | 237 | 48 |
| cce_2958 | DNA | cDNA | Double-stranded | Linear | 543 | 17 | ACB52306 | Amino acid | Protein | Linear | 180 | 49 |
| cce_2959 | DNA | cDNA | Double-stranded | Linear | 912 | 18 | ACB52307 | Amino acid | Protein | Linear | 303 | 50 |
| cce_2960 | DNA | cDNA | Double-stranded | Linear | 99 | 19 | ACB52308 | Amino acid | Protein | Linear | 32 | 51 |
| cce_2961 | DNA | cDNA | Double-stranded | Linear | 933 | 20 | ACB52309 | Amino acid | Protein | Linear | 310 | 52 |
| cce_2962 | DNA | cDNA | Double-stranded | Linear | 780 | 21 | ACB52310 | Amino acid | Protein | Linear | 259 | 53 |
| cce_2963 | DNA | cDNA | Double-stranded | Linear | 816 | 22 | ACB52311 | Amino acid | Protein | Linear | 271 | 54 |
| cce_2964 | DNA | cDNA | Double-stranded | Linear | 129 | 23 | ACB52312 | Amino acid | Protein | Linear | 42 | 55 |
| cce_2965 | DNA | cDNA | Double-stranded | Linear | 267 | 24 | ACB52313 | Amino acid | Protein | Linear | 88 | 56 |
| cce_2966 | DNA | cDNA | Double-stranded | Linear | 1065 | 25 | ACB52314 | Amino acid | Protein | Linear | 354 | 57 |
| cce_2967 | DNA | cDNA | Double-stranded | Linear | 1107 | 26 | ACB52315 | Amino acid | Protein | Linear | 368 | 58 |
| cce_2968 | DNA | cDNA | Double-stranded | Linear | 444 | 27 | ACB52316 | Amino acid | Protein | Linear | 147 | 59 |

TABLE 1-continued

| Gene | | | | | | | Gene product | | | | | |
|---|---|---|---|---|---|---|---|---|---|---|---|---|
| Gene ID (CyanoBase-ID) | Type of Sequence | Molecular type | Number of strands | Topology | Length (bp) | SEQ ID NO | Protein ID (NCBI-Protein ID) | Type of Sequence | Molecular type | Topology | Length (aa) | SEQ ID NO |
| cce_2969 | DNA | cDNA | Double-stranded | Linear | 285 | 28 | ACB52317 | Amino acid | Protein | Linear | 94 | 60 |
| cce_2970 | DNA | cDNA | Double-stranded | Linear | 1011 | 29 | ACB52318 | Amino acid | Protein | Linear | 336 | 61 |
| cce_2971 | DNA | cDNA | Double-stranded | Linear | 1560 | 30 | ACB52319 | Amino acid | Protein | Linear | 519 | 62 |
| cce_2972 | DNA | cDNA | Double-stranded | Linear | 387 | 31 | ACB52320 | Amino acid | Protein | Linear | 128 | 63 |
| cce_2973 | DNA | cDNA | Double-stranded | Linear | 1221 | 32 | ACB52321 | Amino acid | Protein | Linear | 406 | 64 |
| cce_2974 | DNA | cDNA | Double-stranded | Linear | 204 | 33 | ACB52322 | Amino acid | Protein | Linear | 67 | 65 |

Alternatively, the nitrogen fixation enzyme in the embodiment of the invention may have any one or more of the amino sequences of SEQ ID NOs: 34 to 65.

The nitrogen fixation enzyme in the embodiment of the invention has preferably not less than 5, more preferably not less than 10, further preferably not less than 15, further preferably not less than 20, further preferably not less than 25, further preferably not less than 28, and further preferably not less than 30 of the amino sequences of SEQ ID NOs: 34 to 65. The order of the amino sequences of SEQ ID NOs: 34 to 65 ma be changed but is preferably not changed.

In addition, the nitrogen fixation enzyme in another embodiment of the invention is not limited to that expressed by the above-described transformant in the embodiment of the invention as long as it is a nitrogen fixation enzyme having the same amino acid sequence as that of the above-described nitrogen fixation enzyme in the embodiment of the invention. For example, it may be, e.g., that synthesized by a commercially available protein synthesizer.

The nitrogen fixation enzyme described above is not limited to that having the same amino acid sequence as that of the above-described nitrogen fixation enzyme in the embodiment of the invention and may be a nitrogen fixation enzyme with an amino acid sequence having not less than 40% identity with said amino acid sequence. It is preferably a nitrogen fixation enzyme with an amino acid sequence having not less than 50% identity with said amino acid sequence, more preferably a nitrogen fixation enzyme with an amino acid sequence having not less than 60% identity with said amino acid sequence, further preferably a nitrogen fixation enzyme with an amino acid sequence having not less than 70% identity with said amino acid sequence, further preferably a nitrogen fixation enzyme with an amino acid sequence having not less than 80% identity with said amino acid sequence, further preferably a nitrogen fixation enzyme with an amino acid sequence having not less than 90% identity with said amino acid sequence, further preferably a nitrogen fixation enzyme with an amino acid sequence having not less than 95% identity with said amino acid sequence, and further preferably a nitrogen fixation enzyme with an amino acid sequence having not less than 98% identity with said amino acid sequence.

The nitrogen fixation enzyme with an amino acid sequence having not less than 40% identity with the above-described nitrogen fixation enzyme may be artificially synthesized by a commercially available protein synthesizer.

"Identity" of the base sequence or the amino acid sequence as used herein means a level of homology of bases, or amino acid residues, constituting each sequence between sequences to be compared. Regarding the amino acid sequence, a presence of gaps and properties of amino acid are taken account of (Wilbur, Proc. Natl. Acad. Sci. U.S.A. 80:726-730 (1983)). To calculate the identity, it is possible to use BLAST (Altschul: J. Mol. Biol. 215: 403-410 (1990)) or FASTA (Peasron: Methods in Enzymology 183:63-69 (1990)), etc., which are commercially available software. Any numerical values for "identity" only need to be numerical values calculated by a homology search program known to those skilled in the art and can be calculated by using, e.g., default (initial setting) parameters on homology algorithm BLAST (Basic local alignment search tool) hypertext transfer protocol/www./ncbi.nlm.nih.gov/BLAST of National Center for Biotechnology Information (NCBI).

Effects of the Embodiments of the Invention

The following effects are obtained in the embodiments of the invention.

(1) It is possible to provide a DNA fragment which encodes a nitrogen fixation enzyme allowing for elimination of the need for a nitrogen source required to be added to a medium for multiplication of *Escherichia coli*, a recombinant vector containing the DNA fragment, a transformant transformed by the recombinant vector, and the nitrogen fixation enzyme.

(2) It is possible to provide a DNA fragment which encodes a nitrogen fixation enzyme allowing for multiplication of *Escherichia coli* without adding a rare metallic element such as V or Mo to a medium, a recombinant vector containing the DNA fragment, a transformant transformed by the recombinant vector, and the nitrogen fixation enzyme.

(3) The nitrogen fixation enzyme is expressed using a gene derived from cyanobacteria which is a photosynthetic organism producing oxygen (it is a nitrogen fixation enzyme different from nitrogenase). Therefore, it is possible to carry out nitrogen fixation in photosynthetic organisms producing oxygen, such as algae or plants.

(4) It is an energy-saving nitrogen fixation reaction which works under ordinary temperature and normal pressure and it is thus possible to significantly reduce the energy cost as compared to the Haber-Bosch process which requires a large amount of energy in a high-temperature and high-pressure environment.

(5) By introducing the DNA fragment in the embodiment of the invention into industrially useful bacteria, algae or plants, it is possible to obtain a species which can be grown without the need for nitrogen fertilizer (ammonia, ammonium chloride, sodium nitrate, etc.).

EXAMPLES

The invention will be described in more detail below based on Examples below. However, the invention is not limited thereto.

(Isolation of DNA Fragment to Encode a Nitrogen Fixation Enzyme of the Invention)

A genomic DNA extracted from cyanobacteria *Cyanothece* sp. ATCC 51142 (ATCC number (accession number): 51142) was physically sheared, in detail, an extracted genomic DNA solution was drawn up and dispensed five times by a fine-tipped pipette tip (from Quality Scientific Plastics, Inc.) and blunt ends were generated by End-Repair Enzyme Mix (from Epicentre). Alternatively, vortex or sonication, etc., may be used for the physical shearing. The blunt-ended DNA fragments were sorted by size using electrophoresis, and the DNA fragments having an average strand length of 25 to 40 kb were extracted. Next, the DNA fragments were respectively ligated to CopyControl™, pCC2FOS™ Fosmid Vectors (from Epicentre) having a chloramphenicol resistance gene (cut and linearized at Eco72 I site (between $382^{nd}$ C and $383^{rd}$ G) and dephosphorylated) (see FIG. 2). T4DNA ligase (from TaKaRa) was used for ligation to the fosmid vectors. MaxPlax™ Lambda Packaging Extracts (from Epicentre) were used for in vitro packaging of the DNA fragments ligated to the fosmid vectors. *E. coli* EPI-300T1R (from Epicentre) (hereinafter, referred to as EPI300), which is *Escherichia coli*, was used as a host microorganism. Then, transformed *Escherichia coli* (transformant) was obtained in LB medium (LB/Cm) agar plates containing 12.5 mg/mL of chloramphenicol.

A colony of the transformed *Escherichia coli* was taken and placed in 4 mL of LB medium (LB/Cm) containing 12.5 mg/mL of chloramphenicol, and cultured in the air at 37° C. and 180 rpm for 18 hours. Next, the cultured *Escherichia coli* was collected, was washed three times with a M9−N medium (0.6% $Na_2HPO_4$, 0.3% $KH_2PO_4$, 0.05% NaCl, 0.2% glucose, 0.00147% $CaCl_2 \times 2H_2O$, 0.05% $MgSO_4 \times 7H_2O$, 0.01% L-leucine) not containing any nitrogen source (a nitrogen compound such as ammonium chloride, sodium nitrate), and was then resuspended with a M9−N medium. The prepared *Escherichia coli* suspension was plated into a M9−N medium (M9−N/Cm) agar plate containing 12.5 mg/mL of chloramphenicol and was cultured at 37° C. for 72 hours. The obtained colony was subcultured in a M9−N medium (M9−N/Cm) agar plate again, and a strain showing growth was isolated as a clone with nitrogen fixation phenotype. The clone was named Transformant 1.

Next, a base sequence inserted into the fosmid vector of the clone exhibiting nitrogen fixation phenotype was analyzed. As a result, it was found that the previously-described base sequence of SEQ ID NO:1 was inserted into the transformant 1. In this base sequence, it was found that the previously-mentioned thirty-two open reading frames having the base sequences of SEQ ID NOs:2 to 33 are contained and respectively encode the previously-described amino sequences of SEQ ID NOs: 34 to 65. These protein's amino acid sequences are not homologous with the known nitrogen-fixing protein (nitrogenase) and it was thus judged that the nitrogen fixation enzyme and the DNA fragment encoding it, which were obtained in this example, are novel. The base sequence inserted into the fosmid vector was analyzed using pCC2 forward-b and pCC2 reverse-b primers. The base sequences of the used primers are as followed;

```
pCC2 forward-b;
                                    (SEQ ID NO: 67)
CCAGTCACGACGTTGTAAAACG

pCC2 reverse-b;
                                    (SEQ ID NO: 68)
CGCCAAGCTATTTAGGTGAGAC
```

(Evaluation of Nitrogen Fixation Ability of the Transformant)

Figure 3:
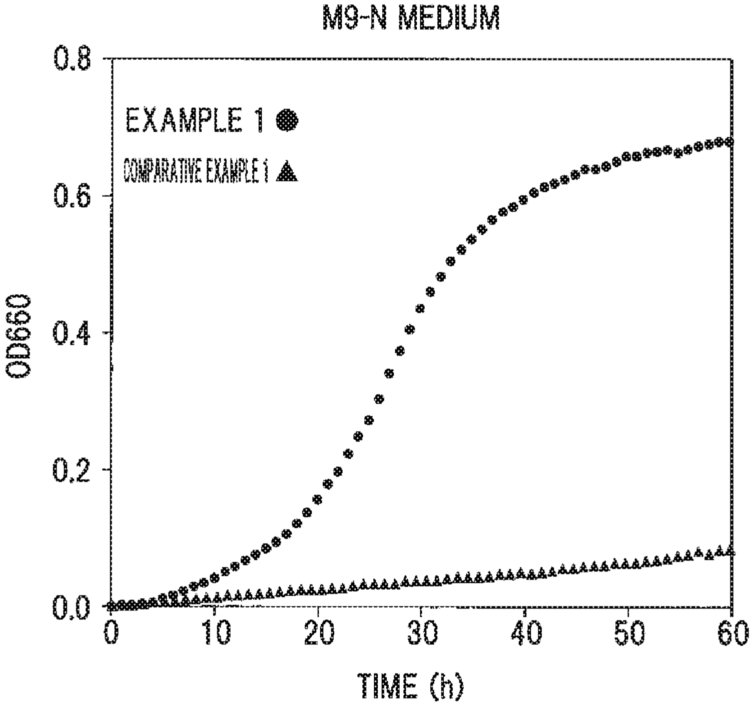
FIG. 3 is a graph showing evaluation results of nitrogen fixation ability in Example.

Using a M9−N medium not containing a nitrogen source, a multiplication test was conducted to evaluate nitrogen fixation ability of the transformant 1. The transformant 1 (Example 1) and EPI300 with a pCC2FOS™ Fosmid Vector (from Epicentre) with no DNA fragment insertion described above (Comparative Example 1) were cultured for 24 hours in M9+N media (M9+N/Cm) each obtained by adding 0.1% ammonium chloride as a nitrogen source to a M9−N medium, and bacterial cells were collected, were washed three times with a M9−N medium and were then inoculated into 5 mL of a M9−N medium (M9−N/Cm) so that the optical density at a wavelength of 660 nm (hereinafter, described as OD660) was 0.02. Shaking culture was carried out at 37° C. and 45 rpm by using a small shaking culture apparatus [Bio Photo Recorder (trademark) TVS062CA, from Toyo Co., Ltd.] and OD660 of the broth was measured every hour. The multiplication test results are shown in FIG. 3.

In the M9−N medium (M9−N/Cm) not containing a nitrogen source, multiplication of *Escherichia coli* EPI-300 (Comparative Example 1) was significantly inhibited but the transformant 1 (Example 1) exhibited rapid multiplication. This result shows that nitrogen fixation ability can be provided by introducing the DNA fragment, obtained in this example and encoding the nitrogen fixation enzyme, into *Escherichia coli.*

The invention is not limited to the embodiments and Example and can be changed in various ways.

REFERENCE SIGNS LIST

1 GENOMIC DNA
2 DNA FRAGMENT
3 FOSMID VECTOR (RECOMBINANT VECTOR)

The invention claimed is:

1. A recombinant fosmid vector, comprising:

the base sequence of SEQ ID NO:1, or a base sequence having not less than 95% identity with the base sequence of SEQ ID NO:1.

2. A recombinant fosmid vector, comprising any one of SEQ ID NOs: 2-10, 14, 17, 18, 25, or 26, and encoding a nitrogen fixation enzyme.

3. The recombinant fosmid vector of claim 1, which comprises a base sequence having not less than 95% identity with the base sequence of SEQ ID NO:1 and encoding a nitrogen fixation enzyme.

4. A transformant transformed by the recombinant fosmid vector of claim 1.

5. The recombinant fosmid vector of claim 1, which comprises the base sequence of SEQ ID NO:1.

6. A transformant transformed by the recombinant fosmid vector of claim 5.

7. The recombinant fosmid vector of claim 1, which comprises a base sequence having not less than 98% identity with the base sequence of SEQ ID NO:1 and encoding a nitrogen fixation enzyme.

8. A transformant transformed by the recombinant fosmid vector of claim 2.

* * * * *

SEQUENCE LISTING

```
<160> NUMBER OF SEQ ID NOS: 68

<210> SEQ ID NO 1
<211> LENGTH: 31247
<212> TYPE: DNA
<213> ORGANISM: Cyanothece ATCC51142

<400> SEQUENCE: 1
```

-continued

```
acgaaagata atggtggcgg tcctcaaacc atctccattg attaagtcaa ttgactcgat     60
atatcaggag ataggagtta tacatttaac ctatctccta acaccgcagt tctctttccc    120
tgttactttc agactaaatt agggaatatt aaaactagat aaccaaagaa cggtaatctt    180
gaccccttt tgcatccgat tggtcaaaag tccataatgt gacatcggta agagtgaatg    240
agctactgtg taaacccatc ttgcgcccaa cccaaaaacc ccaataatgt ggcggtttgt    300
caatcttgcg gttctcaact gcgattaaat aatcgttatc aaccccttagg tattcttgga    360
aaaggggct ttggggccac ctttggggct gcagatattt cccttccagg gaatcccatt    420
tgtgttgtta agcagttacg accagcgaca gacgatcctc aagtctataa aatggctaaa    480
gaattgtttg aacgggaagc agaaacttta ggtaaagtgg gaaatcatcc ccaagtcccc    540
agattattag actattttga acaaaacaaa gaattttatc tggttcaaga atatgtcaaa    600
ggatacaatc ttcatcaaga ggtcaaaaaa aaggggccgt ttagcgaagc aggggttaaa    660
cagtttttga cagaactctt acctattcta gaatatatcc attctcagaa agtcattcac    720
cgtgatatca aaccagctaa cctaatccgt tctcaaaaag atagtaaact ggtcttaatt    780
gactttggag cggtcaaaaa tcaggttaac tctatggttg cgaataatac ccaaaccgct    840
tttactgctt ttgccgtggg aacagcaggt tttgcccctc ctgaacaaat ggccatgcgt    900
cctgtttacg cgagtgacat ctatgcagtg gggttacct gtgtctattt attaaccgct    960
aaaaccccca aagatattgg ttgtgacccc gaaacagggg aaattgcttg ggaaccctat   1020
gttaatatta gtgactcttt ggccaatgtt cttaaaaaga tgttggaagt atcggttaaa   1080
catcgctaca aatcagccga acaagtctta gatgctatgg ccatggcccc ttatgaacaa   1140
gggatgcaag atagcatgac tactatgatc acaggattta aaactcctag tagttcgtcg   1200
agtcccaact cttcactcag taccggttta gtcagttcat ccccatcgac cagaactatg   1260
ggaagagtca acacccatat ttctaaggga agtcccatgt cctcagtttc tccagaggat   1320
aaacactccg tcgctactaa gattcaaggt agggttgcag ggtgtggaaa tgctaactac   1380
aatatagctc atggacaaac ctctagccgt cgtcgtggta aaggacaagg aatctctaac   1440
tctgatacca tagcaactaa aaaaaaccag aaaaaatggc aagaaaaaac cttattaact   1500
gcttatgaaa atggtcgaag agactttact aatcaagaat taaatgaact caatttatct   1560
aaagcttttt taccaggaat taattgttat caagccaaat taagccgtat taatttacaa   1620
ggggcagaat taacccgtgc ggatctcgga agagcagatt taacccaagc agtgatgaaa   1680
aatgccaatc ttagtgaggc ttatttagga tacgctaact taaatggagc ggatttaaga   1740
ggggcgaatt tatgtggggc caatttaacc tatgctaatt tacaaggagc aaatctctgt   1800
ggggttgatt taagttctgc aagaattact gaggctcaat tatctgtagc taaaaccaat   1860
tggcgaacag taatgcccag tggtaagcga ggattttggt aatctaatac aaagaatata   1920
atttaagtct ctagtaactt ttgagacttg gtataactcc gaactcacgt tgattgagtc   1980
ctgggagtga acaaaaggta caaacaagga ataaccacta aagcaatgac tgtagccgcc   2040
actaaaccga agataatcgc actacataaa ggcatccaag tgggatcact caaagctaga   2100
ggaattaacc cgataatcgt ggtaatactg gtggttagca caggtcttaa acggtcagca   2160
accccttttgg ctgcggctaa acgtaatttt attccttctt gttgataact attcatggta   2220
tcaaccatga cgatcgcatc attgaccaca attcccacta aagcaataat cccaataaaa   2280
gcggtaaagg aaaaggcgat atctgccagg aaaaagcccc caacggttcc tatcaatgca   2340
```

-continued

```
aaggggatgg tcagtaaaat gataaagggt tgacgaaatg atcccagttg taacaccagc   2400
actgcaaaga cgagaaaaat agctaaagct aacgcttgac cggcagagcc aaaggtttcc   2460
gcttggtctt ccgtttctcc cccgaaagta taatcatagc cttggggcca agattcttgt   2520
atttcttgta atttgggctg taaatccgct aaaatttccc cagtagtgcg attttcattc   2580
tttgccaaga cggtaacagt gcgctgtcct ccgcgacggg taatagataa aggggcttcg   2640
gcttggactg cttcaatcac tgctcctgcg gaaatcactt cttcctctgg gtttgaggta   2700
aagaaacggg ccgataataa ctcatctcga cgggtgggtc cccccacttc gccgttacgg   2760
gacggccaag cagtgctaag gagaatttct aagtcttcct cattgccacc gatgacaaaa   2820
tcaccaatat ctaccgctcg catataatat tgagcttgag aagccagttc ttcttcactg   2880
agatcataaa atgacagttc ttctcgcttg ggaattaatc taaggtcagg ttgcaaggct   2940
cctaaattat ctcgcacatc ggtcgcccca ggtatttgtc tgagggtcat ttgcacttgt   3000
tgagaaattt ccctgagttg gcttaattca ctgccggtaa tttcaatttg aatagggtcc   3060
ccactttccc ctgcttgttg agcatttaag actaaagagg cgcccggata ttgattaacg   3120
gctttttgta attcgttgcg taaatcatct aaatattcaa aggatagccg ttcccgttgg   3180
ttttcaggaa ggaacgtacc tgaaaaaccc actagataac tgccttgagt gggttgtagt   3240
tcccctgatg ccactaaatt actgcgctgt cctgtatatt taatcacgct gtcaagatag   3300
tctttttctc gtaaaatttc tcctaggtcg tcggctactt cttgggaaac gtctagggtt   3360
gtggtggggg gtagttccac attgacacta aagttgcgtt gatcgcctct gggaaaaaat   3420
tccacggaaa tttgactaaa taaggtcatg aaacagaaaa agagggcaat ggttcctaat   3480
acccaagccc aagccgtttt tttatttcta acggtataat taagactcca attcatccaa   3540
cgagcagacg cggcttgact taaacggtca atggttgatt ttttttcaac gcttctcata   3600
ttgcctaaca agtaacgaga cagaggaata tcaattaaaa tggcaataac aaaactgagg   3660
actaaacaaa taattgcggt gtagggtaac aattcaataa actttcccaa agtaccgcta   3720
atggccagta agggaaatag ggctaaaatg gtggtcaatt gtcctgcaaa agcgggtggt   3780
gcgtaagttt taacggtttt taacgcagct tggttaaaag acagtccctc agcaaagata   3840
aactcgtgca tcccttccat caccaaaatg aaaacatcca ccaagatacc caaggccaag   3900
accataccaa tgagtaccat attattgagg gtttgtccgg ttaaccataa caccgctaac   3960
gctcccaaaa aggttaaggg aatggataac ccggcaatta aggcttcacg ccaagaaaga   4020
gcaataaaca gcaccacaaa cacggcggcc atagcttgca aggcattggt aaataaattg   4080
cccaactgtt cccaaataat atccgattca tcggcaataa tttgatattc catgcctctg   4140
ggccacagat tcggattttg ctcaatttgc tccatagcct ctaaaacccg ttcaataacc   4200
tcaatcgaat cttgtccagg tacttttttta atacctacac tcaccacagg ttgataagct   4260
tctccttggg tactaataaa ggcacgggtt tcttcttggt caagttctcg acgcacctct   4320
gccagttcac tgaggcgtac tactcgcccc tctaaacgag cgatgggtaa atcttgtaat   4380
gcttctacac tgcgaaaacg agcataaaag cgtacctgtg acccaattaa atcactttct   4440
atctctgaga gggggacatc tcggttagca ttacgaattt ctgtggcaac cgttgtggga   4500
gaaatgccca acgtggctaa acgaaagggg ttcatttgca cattaatgac ctcttctcgc   4560
gctcccccta ggttcacctc actgacccct gccacctgtt ctaaattgtc ttgaatgtcc   4620
tctgctgttt gagaaatcac cgtttgatca atgtccccaa acaaggctaa ggtaaggata   4680
ggggcatcat tgacggaaat ttgttctact acgggttgct ctgcctcttc aggtaattcg   4740
```

-continued

```
ggttcggctt gggcgacccc ttgccgtaat tcttcgatcg cttcatcggg gtcggcctgg   4800
gacgtaaatt cgacattaat caccgaaaac cctgcataag aagcactttg aacctctttg   4860
acattttcta ctgaagtaat ttctgtttca atttcagaag taacttgttg ttctatggtt   4920
tgggggtcgg ctcctggcca ggtggtagtg acggtggcaa cggcaatatc aatatcaggg   4980
ttagactgtt tggtcatgga aaaataaccc aaaagacccc ccaccaccat gagcaaggtt   5040
aataaaatag caaaaatagt gtttaaaaag aaaaatcgtt ctaatcggga ggtttttttg   5100
ccattgactg aggtattatg tccattatta ttgcttctga aatcttcttt taactcactc   5160
attatctacc ttggttaatc acttcaacac tcgccccgtc caccagtcgg ttgtgtcctt   5220
ccgtgaccac taactcccca ggtgttaccc ctgtgataat tccctgttgg gtaatgcctg   5280
taatgcctaa ttctacctct cgctgctcga caatattttc tgcttcgttc accacgaata   5340
cataaggaat gcgatcgcgt cgtacaatgg catcgatggg aacagtgaca gcgttggggt   5400
tttccgacac agcgatccaa gttaacacct gttctccatg tcgtagggtt tcggtggtgc   5460
ttggattaag acgaatggtg gcttctatgg ctcgtccccc cggactaatg gcagggttaa   5520
cggcaaagac ttcaccccta gcgcgagcgt tagtaattaa ggtctgttga gatgtagccg   5580
cagtattgac ttgggtttct gaggcaatca cagcgttttg accggcttcc acttgttccc   5640
ctgtaggccc ggctaaatct accatgacct cgtattgact cggatcaata ataaccatgg   5700
gaatacgttc taaaatccct tgataatctc ccccgagttg agaggtaacg atttgtggag   5760
agaaatattc tccttctgaa atattgagat aggcaataat gccattaaaa ggtgcataaa   5820
tactggctcc ttctaaagct acctctgctt gagataatcg ggcttcggct gtggtaatgg   5880
cggaggtttg ggcttctacc tgttgttggg ctgcttgtac ttgagcttgg gctgcttcta   5940
cttgttgctg ggctgactgc actcctgctt gagccgactg aacccctgct tgagcatctt   6000
ctaaggtgtt ttgacgttca tcaaattcga tttcagccac tgcaccctct tctacgaggg   6060
ttcgataccg ttctaaactg gttgctgcta atcttcgggc tgcttgagca ttttgtagtt   6120
gggcttgggc ttcttgtact tgcgatcgcg cttgagcaac ctgggcgcga gcttgagcta   6180
cgtctgcagt ggcggccgcc ctgttttgtc gggcttcggc gatcgcagct tgggcttggg   6240
tgacatctgc ggtgagttcg cgatcatcaa tgcgagctaa taattgtcct tttgttacgc   6300
gatcgccttc tcgcagtctt ctaccgtctt ggttagccag ataggtaaca tccccttctg   6360
tgtcaaaggt aagatgttga tagtctacgg ctctaacact gccttcactg gagatccaag   6420
cccggagggg ttcccgtgtc gcggtggcaa cctgtactga aagggaaact gtttcggtga   6480
cagtgacagg ctgatcattg tctcgaagac gaataactgt gactcccccct aggacgaata   6540
ataaaccaaa tactggcaat aaccaccata gtttttttaat atttcttttc tgctcttttt   6600
tatcagagct tttcggagtt tctttgtatt ctgagggtag atttttgtct agaaattgct   6660
cagtatcatt agatttttgg ggtcttgatg gagggatatt tgagggcaaa ggattgtgag   6720
tctgatgatt cataaaataa gctatataaa atgtctagct agtataaata aattagataa   6780
atataaggat ttagcaatta atttaattgt cataattttg tataagcttc aacatcccct   6840
attagacaga ctttgacact tttgctattc aaaaacaaca acgcaacgga attaaaaaat   6900
ctctaacaat tcatggtttc ccccagggtt ccaaaccagc aatatagcac tatgggttat   6960
ggttaacctg agttcgacgg aagagaatct agggaaaact gacacccaac aagaagtctc   7020
ataccaaatc cgcttatttt agtagagtaa ctttttttctc ccttctccct gctccctgct   7080
```

-continued tcgagacttg atactatact atctaaagcg gatctcttat caaaccctga ttccctcctt 7140
aaaaaaattc taactccgtt gcgtagcacg acgtagtcgc actccgaact cctaaaaccg 7200
aactcacgtt gttaataata gagaattagt ataattttg tactgctacg gtgtaggatg 7260
atatattttt gcttcgacaa aaattttgct tctttattat gattatggct gccaaaactg 7320
atgaaattgg ctaaagctga ccctaaaaag gttgtttttt tctacattga acacacctca 7380
accacatcaa tagattagag tcaggttgtg tttaaagagt ccctttaaag atgccttgag 7440
gacgaatcaa aagaattaaa atcataatta ataaagctac tcctaattta taatcaggtc 7500
ccaaccaagg tacactcagt tcttgagcaa ctccaataac taagcctcca gcgatcgcac 7560
cataagggtt gccaataccg cctaaaatca cagaggcaaa catgggtaaa attaaaaacc 7620
atcccatatt aggtcgtacg gtactggtaa ttaatcccaa catgacaccg cccaaggtgg 7680
ttaaaatggc tgtaattacc caagtccaga ggacaacttg ttcaacatta attcctgaaa 7740
ccctagctaa atcaatatta tcggctacag ctcgcatggc cttaccaatt tttgtgtttt 7800
gtaacactaa atgtaaaatg gcgatggcta caattgataa aataatcgcc caaattctgt 7860
cggtggctaa ctgtaaccca aaaagttttt gtgcttgaac caagggaata tcataccgtt 7920
gatttttcgc tccccaaatc attaaaatgc cgttacgcaa aaataaggct aagccaatag 7980
agataataat tagggtggtt gaagttgctc tgcgatcgcg catgggtttc cataataaat 8040
attctgaaac taacatagcc aaaacggttc ccatcgcacc gataatcacc gataagccta 8100
aatttaggcc ttgagtgttg gctaaccaag ttaaataggc tcccaaggtc ataaaatctc 8160
cgtgagcgaa gttagaaagc cgtaaaatac catacgtcaa ggttaacccc accgcagcga 8220
gagcaatgac actgccaatg gctaagccat caaataagtt ttgtgctgtc cttaaaatta 8280
gttctgaggt ttccatgctc caaaattgtt gtatcctgcc tgtctcaatg aagatacacc 8340
atcttgagaa agtttgctta cttaaatggg gtaaatgggg tgttgagata agttatctct 8400
aattccctct cgttgcactc acgacaactc atggaacaaa attaagcgat cgggatggca 8460
ggatttgaac ctacgacatc ctgctcccaa agcaggcgcg ctaccaagct gcgctacatc 8520
ccgtaacgtt gcttacccat tataactcaa actgtcccta atcaggatac caaaacatcc 8580
ctttaattcc ttctgggtct agtacaaacc ccaaacgacg gtaaaagtcc accacttggg 8640
gatcggcaaa gagggtaata ttactaatat cttcgcttct taattgacga atcatatact 8700
tcatcatccc ttttcccagt cctttacttt ggaacctcgg atgtataacc acatcccata 8760
tagtggcatt aaaggcgtga tccgacgtag cgcgagcaaa cccaattaaa cgcttccggt 8820
ttccttttac ttcccatgct gacactacca taaaactata ggtgagtgcg cgtttaactt 8880
tcctcagagg acgacgagcc catcctaccg catcgcataa ttcttcaagt tcatagagat 8940
cgatttctct ttctctggtg aaaaaaatac gcgtttgacc gtcagtgtgg ccttttaagt 9000
tgaccggctc ccctttaaac tgggactttt ggtctgtgtt tgatatatct gtattattaa 9060
acaatcgttt ccaaaaaacc attagattga aagagacaac ccctatttag ttaagtattg 9120
tcgcataaaa atgagcaaag agtagggagc atattatttt tgcacaacaa ttatctttta 9180
atattgacgg ggaggggga gacggggtta aattcatagg acaactatga taaataaagg 9240
acaattttaa aaagataaac aaatggcagt caatcgtatt agaattggta aagataaagg 9300
agaattagta cagtctttgg tggatttcaa tggaggagtt ggaccttttc aaacttatgc 9360
tgatgtgatc acctttgcag caacattagg ggcaaagtac aacaaacgca ttcctctgaa 9420
tataatttca aaagaaccgg cacccattag cttagaaatc tttgtttcta gggggtacga 9480

-continued

```
tgccgtgata aaattattgg caattactga aactaatgat cctcatattc tctctcttta   9540
tgacaccgaa gcagaaaacc aaagaattca aatctttgaa gaatacgcca atggtggcct   9600
tgaacaatta caagaagaat taaaaggcat tgtagattat tcagagcatt tattattatt   9660
gttgaattta gaaagattcc ccaataatac cacagaagag gaatttgatt taactcgatt   9720
tctttgaaaa atggacttta ttttttgatg attattcttc tattttgatg atcaataatc   9780
agagtatttg ttgtatttaa taattatttt aagaaaaata atgaatccca aagagaacaa   9840
aaaagaattg agacaaaaaa taataaaaaa acgagagaaa ttatcaaaaa tagattggat   9900
gaataagagc aataaactgt gtgaaaatct acaaaattat cctttattgc aaaaatctaa   9960
aacgattcta gcttactttt cagttcgcca agaacctaat ttaatttccc tattttcaac  10020
tgactataat tgggggtttc ctcgctgtgt aaaaaagtct ttaatctggc attcttggcg  10080
cagagaagat ccgcttatac ctgggaaata tggcatttta gaaccggctg cgaatgcgcc  10140
tattttaacc cctgaaaaag ttgatttaat ccttgttcct gctgtggctt gtgattacaa  10200
tggttatcgc ttaggctatg gtggaggttt ctatgatcgc ttcttaaatt ctcctcaatg  10260
gcattctatt cctacgattg gcattatctt tgaatttgcc ctattacctc aacttcctta  10320
cgaaccttgg gatcagaaat tacaagcaat ttgtacagaa aatgaaatca taagcatatc  10380
tacttaagct tatctattaa gatttatgaa gttgcttagc aactcagaat ggttttgtta  10440
atatgaatga taactattct taaactgtag attaacgggt aaaaaataga ttaatttata  10500
cagaaattag tagtaaatcg agggatctaa aaaaattatg aaacatttta gagatgaatg  10560
gatacaagaa tggtgtgaag aaaatggatg gacagattta tttagggaac gttacaatca  10620
ttattgggca tttcctccag gtgcagtgat gcctgaaccc attccctctg aagtattacg  10680
attcattaaa gcaacaaaag gcttttgcgc ggaagaaaga acctggttaa tttcagctat  10740
tttagtctca attatatccg ttgtgttgag ttatttcttc aaaaatccta tgcccattgt  10800
ctttgctttt gcttttgctg ctgttacttc ggctaagtta gaagtcgaag agatttaaaa  10860
ataattaatt atcttaaatt attctcaaaa ttcctaacta catactaagg tctatcagag  10920
tcaaaatatt gttgtagatt agacttattt tgttctctat cagactcaaa atatttctga  10980
atattctgtt tattctcctc ttctttaggc ggtttctctt cagcaggttt aggaggaata  11040
tgggggatca ctaaagaagg ttctgaaccc tcttggttag taggttcttt gggttctgac  11100
acttggggag gtggttcaac tggaatagga acaactttag tgggttctgg aataggggtt  11160
gaagtcggag aaggggaagc ttttggagta ggggaaggtt gtacggttga gttaggagaa  11220
ggttctagag ttggggtagg agttgcttct agtgtggggg aaggttctaa agttggggta  11280
ggagtcgctt ctaaagtagg agatgactgc gatcctggag aacgcctaac tggtcgccga  11340
agtgtcggtc tgggctggga aaactctggt tgagaatttt ctggaacttc tggagactca  11400
ggtgaaaccg aaggggaaga agtcggttgc gatcgctctt tcgtccctaa catgatccct  11460
aacattaacc ctccaatgat agcactggct gccaaaaatg aacctaaggc taacaaggcc  11520
caaggggtgt ctgtctctgt ttctgttgct tctgctggta agttggtagg gatgggagtg  11580
tgggtagaac ttctagatag agataaattt tgttgtccaa tggctatggt agctgccgtg  11640
ggaatagtat ggggaacctg caaagcctct aacatttctt tagcagtaga aaagcgatcg  11700
cgaggatgaa aacgaaccgc gcgatcaatg acgtttccca cattagactg aatatctggg  11760
gcttcttttc gccataacac ctccccagta ttgggatcag tggctaaata ttgggggtt   11820
```

-continued

```
tttcctgtga gtaaaaacac catggtcagt cccaaactat acaagtcact tgaatttaga  11880
ggacgaccgg ctgcttgttc ggaagccatg taaccagggg ttcccagtcc gacagaataa  11940
ggcgtattcc catccccatg aatcatggta gcgaccgttt ctttaacaat accaaaatca  12000
attaaaacag gtttttatc gtgactgcga ataataatgt tatctggttt aatatcacgg  12060
tgaataatac gacgactgtg gatatagtca agaacgggta aaatacctat taatatctct  12120
ctaacttgat taggtgacaa attgccttgt cgttgatgaa tttgggttaa ggtttctcct  12180
tcgatccatt cttgtactaa ataaaaatct cctccttcgg aaaaataagc gtataatgtg  12240
ggaatttgag gatgttttc ccctaattct tccaaaatag ctgcttcttt ggcaaatcgt  12300
tcctttaacc aatcaggaat aacaggagac tgaaccgccg gtttcagttg tttgatcaca  12360
cattttcttt ctgagggcat atgggtgtca atggcgagaa atgtctcccc aaaccccccct  12420
tttcccaagg tttcaatgac ttgataacga ttatttagta ataatgacac ggtacccccct  12480
ttattgccct agtcagacaa tcaagcttta ttgtagctaa tcctcatccg taacttgaga  12540
ctcattttct caatgtcagc gaactattgt ttgcggtagt cccattaaaa acagtgatcc  12600
tggttgaaaa tattagcatt ctcaacacaa gggacaattt caccgaataa acttgcccac  12660
aaatatatga ttattgtttt acagcgattt tcaattgagt ggaaaatcta gaaatctaac  12720
tcctgcctcc tgcctcaaag ctaaatagtt tatattttat gcaaatgaaa actggtgtta  12780
gttttgagac tcaactattt tttagcaatc acccaaacgg cgtgaacaat accaggaata  12840
taacccaata acgttaacaa aatattgatc cagaactggg gtccaatacc cacttgtaga  12900
aaaacaccca gtggaggaag gataatggca caaataatcc gaacgacatc catattttt  12960
cttaggtata tatacacttg tgattattca tgaaaccaat tagcttgtca agatcataat  13020
gttaactctt tactagggaa aaattgtaat ttcaataaca aatcatcagt gattttccta  13080
attgccacat aaaaaatgag tgtagataat tggattatct ccaataataa taataatatt  13140
gattatgtcc tattcactat ctcctcaaga aaagtccaat acaactttat tttctttatg  13200
taatcaacgg aaacatcaac ggtattataa tagtcaagga tcttcggttg aactactgat  13260
tgatgggcaa gagatcaaac aatctttaaa aggaatgatt attgatgatt cttttagtgg  13320
ttgtgggtta attattatcg gtgaggaaaa gttacatatt ggtcaattat gtcgtttaag  13380
aataaagggt attgattcca ttttatgtca aattatttgg ttaagaagat tagaaaaatc  13440
cattactagg ataggcgtta aatatttgat taaatccgag taattatgat taattaacta  13500
aacaatagaa aagataaatt tttgaatatt taaaataagc gaattgaaaa aacttgattc  13560
atccctaaag ttctataatt tagggatgaa tagcaacatg aggatcaatg taatctcaga  13620
aggagaagga gatatcccta tttactttaa cgattcttat cgtccaacaa tcctaataat  13680
ggacctaaga taaatccaaa cacaaatcct cctgcatggg cccaataagc cacaccaccg  13740
ccttccattc ctacattagt ttgaacattt aaactcgcaa aaccataaat agcttgttgc  13800
aaaaaccaaa atcctaaaaa gaagactgcc ggaattctaa tcgttgtaat aaaaattcct  13860
agaggaatta aggttaacac ttgcgcttgg ggaaaccgta aaatgtaagc ccccatcacc  13920
cctgcgatcg ccccactagc ccccaaagaa ggaacctcag aataaggggc aaaataccat  13980
tgacttaaac cagctaatac ccccacaagtg agatagaaaa tcaagtattt aacatgacct  14040
aatttatctt caacgttatt accaaaaatc cacaaaaaca acatattgcc tgcaatatgt  14100
aaaaaacctg cgtgaagaaa ttgagacgta aataaggtca tccattcagg aatgggatga  14160
taaaaatcga ctccactaaa ccctgcggtt aattgtttag ggacaatggc ataatattga  14220
```

-continued

```
aaaaattgcg atagttcctc cgaacttaaa ctcagttctt tgaaaaaaac taaaacgtta  14280
agaataatca atccataagt aacataagct gttctttgtg tgggattatt atcatttaaa  14340
ggaaccatat ttgagaattt agaatttaga atttagaagt caaaaataaa atgattaatt  14400
ttttgacccc aacttagctt aacatttcat ttgtgctagt ttctagggaa caaaaaaaat  14460
ctccctagac aagctagaga gaagattgtg aaagtgaact aaattgcctc taaggttgga  14520
tttagaagta gattgatcca ccccaataag aatctaattt tggtgccact aaaatataac  14580
cagacacatc ataaagatcg tcttcggtga agtctcttaa ttctggatag atatcagggc  14640
gactaacatt aacgtgtaat tctgtatagt cgtcttctcc gtcgtaactg gtgggatatt  14700
ttaaataatc aaccaaacct aatacattat cacggggagg ttcagccagg gataagtctt  14760
ctaatcccaa actaacatta ttattggtct tagtttttcc ttgtaagtga cattgggtac  14820
attcacgaat gaatagtctt tgaccatttg tgatctgttc actggttagg gtgattgttt  14880
ccccttcttc gtttaaagga actgtccgag tttcctcggt taattctaag gcattggcgt  14940
tatggatggg aaattgtaaa aagaaaaaga tagcagcgat cgccatcaga atgaatcgtt  15000
tcaccattgt tctcctgcaa attatgattt tgtgggtata ttaatctttg cacgcattac  15060
ggcaatatca acgataccat aattcctgat ccttaaactt cccttctctg gggggaatgg  15120
gggatttttt cagggataaa aatcgattct ctcccctaag caaacttcat aattcttaaa  15180
agaaacttct cataaatgtc ggctacttgt gtcattaatg gttgggaaag gccagaaaag  15240
acacccatgt taaaactcta tcatttgccg atttccttta attctcgtcg tgtttggatt  15300
gctttactgg aaaaaggatt atcgtttgag ttaattccca tgaaactcaa cggcgatcaa  15360
ctaactccag aatttttagc ccttaaccct tttcatcaca tccctgtcct ggtggatgaa  15420
gcgtttagcc tctttgaatc cctggctatc ttagattatc tcgaagcgaa atatcccacc  15480
ccttccctag ttcctagcga cccccaagga ttagggacag ttaagatgat taacttagtg  15540
accctgaatg aattattacc agcaacaacc ccattaattc agcatagtat gggatttatt  15600
accctagacg aacagaggat agccaacact aaagaaaaag ttgctgtcgt tctcaacttt  15660
tttgagacat ctctcggcga tcgctcctat atagttggca ataccttaac gttggctgac  15720
attgtagcag gaacaatggt ggggtttctg cctcagatgg gtgtttcttt atctgcctat  15780
cctcaattaa ccgcttggac aaagcaatta agtcaacggg aaagttggca acaaacggaa  15840
ccccaaccag aagaaattga caaatttcga gaaaccatga agaaattaat ggctcaacgt  15900
ggttcttaag ctagagagtg attatatact cttttccctg atcttcttac ctccttactg  15960
gtttttttgtt tctagtctcg gattaaagtt cttatgtatt gttaacgaat ttctgcaata  16020
atttaaggtg gactttgtag acgacttaac tctctcgatg gagggaaaag aaaattttag  16080
taatctgctt gtctaaaaca cggttgccat catattcttt taaaacgtac aacctgtaat  16140
tatcgctgag attgacttct caacctatca actaacctag atccatccat caatcgttat  16200
gacacaagta tctggttcat ccgatgtccc cgatatgggg cgtcgccaat ttatgaactt  16260
actcaccttt ggaaccatca ccggagtcgc tgctggtgct ttgtatcctg tggtgaagta  16320
ttttatcccc ccttcgagtg gtggtgccgg cggtggtatt actgctaaag atgccctcgg  16380
taatgacatt atggctagta actttctggc tactcataat ggaggcgatc gcgttttagc  16440
tcaagggtta aaaggtgatc ccacttacct cgtggtagaa ggagaaaatg ctatcgctga  16500
ctacggtatc aacgccgttt gtactcactt aggctgtgta gttccttgga acgccagcga  16560
```

-continued

```
agacaagttt atctgtccct gtcatggttc tcaatacaat gctcagggta aagtggtaag  16620
aggtcctgcc cctctgtctt tggctttagc ccatgttaat gtgagcgaag acgataaagt  16680
ggtgttcagc gaatggaccg aaactgactt tcgcaccgaa caagatccct ggtgggctta  16740
atttcagtga atagtgaaca gtaaccactc aattgaacgg gtcactggta accgataact  16800
gataacgaat taactcccct ttactgttta agaattacat aaatttgact gagcaatgag  16860
aatatccgat ttttcggcaa tttggtctaa gggtaagcaa attttactgc gatcgctctt  16920
gatcgttgca gcaacagttg ccttattcat aggtaacgta caaagtgcta atgcttatcc  16980
tttctgggcc caagaaactg ccccagaaac ccctagagaa gcgacagggc gaattgtttg  17040
cgctaactgt cacttagcag aaaaagctgc tgaagtagaa attcctcaat ctgttttacc  17100
tgatacagta tttaaggctg tagtaaaaat tccttacgat ctcgactccc aacaagttct  17160
aggagatgga tcaaaaggtg gcctcaatgt gggggctgtt ttaatgttac ctgaagggtt  17220
taaaattgct cccgatgagc gcattcctga agaaataaaa gaagagatgg gtagtgtcta  17280
cttccagtcc tacagcgaag gtcaagacaa tgtggttctc gtcggtcctt tacctggaga  17340
acaatatcaa gagattattt tccctatctt atctccagat ccctctaagg ataaaaatgt  17400
taacttcggt aagtatcaag ttcacttagg ggctaaccgt ggccggggtc aaatttatcc  17460
cacaggacaa cctagcaata ataacgtctt caaagcctct aacgctggta ctattagcaa  17520
aattaccgat caagaagatg gtagctacat tgtcactatt gcgacggcag aaggagatgt  17580
agacgaaacg atccccgcag gccctcaatt gatggtttct gaaggcatgg aagttgaagc  17640
aggacaagct ttaaccaata atcctaatgt gggtggtttt ggacaaaaag acacagaagt  17700
ggttctccaa agtcctggcc gcattaaagg attaattctc ttcttagctg gtatcatgtt  17760
agcccaaatt ctcttagtga ttaagaagaa acaagtggaa cgagtacagg ctgctgaaat  17820
gaacttttaa ttaagttggt ttaaccttag tgttactctt ctagttgtaa cagacaggtt  17880
tccccctgtc tgttcttttt atgctttaat agtgataatg attcttattg tcgttgtagc  17940
cttaatctat gaaatcttct cagaagtggt tatcaatgct ccttttgact acaatcctag  18000
ggatgaatag tatcacagga tgtagttcaa gcaatcctgt cgactctggg attaataaga  18060
gtgacaatca agaacaaagc aacagtcaag atcaattaga cattacggtg agtatcattc  18120
cccagaaata ttttgttaag aaaattgggg gcgatctcgt tagggtgaat gtcatggtag  18180
aacaaggggt actccctcat acctatgaac ccaaacctca acaattacaa gcgttaagtg  18240
aagcggaggc ttatattggt attgggattc cttttgaaac cgcatggatg gatcgcatta  18300
aggaagcaaa cccgaaaatg ttgatggttg actcaacaca aggaattgat cgattaacta  18360
tgatagccca tgatcaccat gaagaagaag atcatggtca ccatgaggaa gaaaccaccc  18420
ttgatcccca tgtttggtta tctccaagat tggtaaaaat tcaagcacaa aaaatttatg  18480
aaactttagt gaaacttgat ccgaaacatc aggaaacata tcaaactaat ctcaatagtt  18540
ttttacaaga aattgaggaa ttagaccatc aagttaggaa taacttagct aacttaaaac  18600
aacgtaaatt tattgttttt catccagctt ggggttattt tgccgaggaa tataacttaa  18660
cgcaagtacc cattgaagtg gggggacaag aacctagcgc atcagagtta ggagacttaa  18720
taaaagaagc taaaaaagag aatataaaag ttatatttgc tcaaccagaa ttaagtagtc  18780
aagctgccaa aaccattgct aaagaaatta acggagaagt cttattaatt agtcctactg  18840
ctgctgattg gtctaacaac ttactagaag tttctcaaac ctttgccaaa gtgttaaaag  18900
aagaaaataa tcaatagtat aaatttatga aaactgaagt cattaatctt agtcatgttt  18960
```

```
gggcaaaata taatcataga aatcctattt tagaagacat taacttgact atttatgaag  19020
gggattttgt cggattaatt ggtcccaatg gaggaggtaa aacaacttta tttaaagtgt  19080
tattaggact gataaaaccc tatcaaggaa ctgtaaaaat tttaggtaat actgttagta  19140
aaggaagacg ttatatcggt tatgttcctc aattggtaga attagatcga gagttccctg  19200
tgcgtgtcgc tgatgttgta cggatgggaa gactcggaaa acggcgatta ttgcagcgtt  19260
atacccctca agatgaaatt atcgtcaatc gtaccttaga acaggtagga atgatagaat  19320
tacgcaatcg ccctattgct gaattatccg gtggccaacg tcaacgagtc tatattgcgc  19380
gagcattggc atcagaaccc cgtatactat tattagacga accaacggct agtgttgatc  19440
cccaacgaca aaccagcatt tacgagttat tgaaagaatt aaatcaattg attactattg  19500
ttatgatttc tcatgatatt ggggcaattt cagcttatgt caaaaccgta ggatgtctta  19560
accatcgcct ctttttcat ggtgatcctc ctctgagtac cgaaacaata gaacaaactt  19620
atcaatgtcc tgtggatttg atcgcacatg gggttcctca tcgggtcctt tctaaccatg  19680
attgtccctt acattatcat gaataattga tatgttatag gaggtaatat aaaaatgaat  19740
ttgagtatta ttaatgttag aaacactttg ggaatcatta caatttgatt tcatgagaaa  19800
tgctcttttt gcagggatat tagttagtat tgcttgtgga attattggca cgtttgttgt  19860
cattaatcgc attgttttta ttagtggagg tattgctcac gctgcgtatg gtggtattgg  19920
cttaggatat ttttttaaga ttaatcctat ttttggagca attttttttg ctttactttc  19980
tgctttaggt atgggtttag tagtgagaaa aacagaacaa agggctgaca gtttgatagg  20040
ggtaatgtgg gctgtaggga tggcgatcgg tattatttta attgatttaa cgccaggata  20100
taaagcggat ttaatgagtt atttatttgg gagtatttta accgtttctc aagaaaattt  20160
aatgatcatg ttggttttag atgtcattat tgtgttggtt gttagtttat tttataaaga  20220
atttttagcc atttcttttg accccacctt tgctatgact cgtaatgttc ctgtggatag  20280
tttatattta ttattagtcg gtgcgatcgc tttaacggtg gtgatggtaa tgcaggttgt  20340
ggggttaata ttagtgattg cattgttgac tattccggct gcgatcgctg gtcaattttt  20400
gaaagacata aaatatatta tgttagtttc tattgtattg gggatgttat ttacaacggt  20460
aggattaatg atatcttatt tctttaacgt aacatctggg gcgactatta ttttagtttc  20520
tgggactgct tatttaatta gtttaggggt aaaaacctta caaatttagt tttatttacc  20580
ttgtgctata gttcaccaga aggtataaaa caaggaagac aagaaggtaa attagctgct  20640
aaaattgcct ctattcctcg gttagtcaca ttagaattaa gtgtagaaca aattgctcaa  20700
gcattatagt tagagattga acaagttaga aacattgtta aactaattaa taagcaatct  20760
tgaagagatc cgcacttact tcgtttctct cctagtccgc agtgcgccta ttataattga  20820
caaaatactg tgaaaactga cagcattttt tatcaactgt ttcaaacgtt tttacaaatt  20880
gccattaatt agtcgtcagg agatagaaaa aatgtttagt ttaagtgatc ttagagaaac  20940
caaagtgtat caagaagcat tagaagaagg aatagaaaaa gggatagaac agggaataga  21000
acaaggaaga caagagggag agttagcggc taaaattgcc tctattcctc gcttagtcgc  21060
attaggttta actatagaac aaattgctca agcattagaa ttagacattg aacaagttag  21120
taacattgtc gaatctaata aataagtgaa tgccgatttc ttgaatagtt aacaattaat  21180
attattctaa ttccgaactc cgaaccctga actcccgtta ataaacattc gttacaaatg  21240
ctataacacc ggccaccccc aatgatacgc taaacaatgc acgcttatta ctggggaagc  21300
```

-continued

```
cataatgaca ggagctaacg atacacccta tctccttcgt gctgcacgag gagaaatctt  21360
agatcgtcca ccagtttgga tgatgcgaca agctggacgc tacatgaaag tatatcggga  21420
tttacgggat aaataccccca gttttcgtga aagatccgaa aatcctgacc ttgccatcga  21480
aatttctctg caaccttggc gagcatttca accggatggg gtcattatgt tctctgatat  21540
tttaaccccg ttacctggga tgggtatacc tttcgatatt gtcgaaagca aagggcccgt  21600
tattgatcca cccattcgca ctaaagaaca agtggataac ttacgtcctt tagatccaga  21660
agaatcctta ccctttatca aaactatttt acaaagttta cggcaagaag tgggtaatca  21720
atctactgtg ttaggatttg tcggatcacc ctggactttg gccgcttatg ctattgaagg  21780
aaaaagttct aagaattatg ccatcatcaa gagtatggcg ttttctcaac ctgagatcct  21840
ccatagtttc ttgagcaaaa tagccgatgc gatcgctatt tatgttagat atcagatcga  21900
ctgtggggcg caagtagtac agttgtttga ctcctgggcc ggtcaactga gtccccaaga  21960
ctatgaaact tttgctctac cttatcaaca acaggtggtg cgtcaggtga aagaaactca  22020
tcccgatacc ccgttaattc tttatattag cggtagtgct ggtgttttag agagaatggg  22080
acagtctggg gtcgatattg ttagcgttga ctggactgtg gatatggccg aagccagaca  22140
gcgtttaggt agagacatga aggtacaggg gaatattgat ccaggtgttt tatttgggtc  22200
ccaagacttc attaaagcgc gtattcttga cacagtacgc aaagctggaa gaggtggcca  22260
tatattaaac ttaggtcacg gtgttttagt gggaactcct gaagataatg ttcgttgctt  22320
ctttgaaact gcgaagcagg tggatcaatt attagctgtt cctgtataac ttttaggggt  22380
caacggctgt tgaccccccac tggtgtctat ttaaactgtc tattcattgt tattaagcaa  22440
ttagtttttt taagatccat acattattaa tgacaaaaat agcaagcttt ttaacataaa  22500
ttgacaatgt gttgtaactc ttaataaaaa gaggggttac gaatggcatc caggctggta  22560
gactgtgatc caagcctcgt aaatgactgc taaaaaacgt aacaattttg ttaccgaaaa  22620
agtagaacga gtccttgatt gattcaaaaa aatcccttta aacaagctat ggtcaatacc  22680
cttcaaaaac ctgaatttga ggaactccgt ccaggaatta aagttccggc caaagaaact  22740
atcctaaccc ctcgctttta caccaccgat tttgaagcga tggcaaaaat ggatatttca  22800
gtcaacgaag aggaattaca agctattctc gaagagtttc gcactgatta taaccgtcat  22860
cattttatcc gtcgtgaaga atttgcccaa acctgggatc atattgatgg ggatacccgt  22920
cgcttgtttg tagaattttt agaacgttct tgtacggcgg aattttcagg gttccttctc  22980
tacaaggaat taggaagacg gttaaaggat aaaagtcctg ttttggcgga atgttttacc  23040
ctcatgtccc gtgatgaagc ccgtcacgcc ggtttcctca ataaagcctt atctgatttt  23100
aatatgtctt tggacttagg gtttttaacc aagagtcgga gttatacctt cttccaacct  23160
aagtttattt tctatgccac ctatttatct gaaaaaattg gttattggcg ttatatcact  23220
atttatcgtc acctagaaca acatcccgaa gacagaatct atccgatttt caacttcttt  23280
gaaaactggt gtcaagatga aaaccgtcat ggggactttt ttgatgccat catgaaagca  23340
actcctgaca ttttaaacga ttggaaagcc cgtttgtggt gtcgcttctt cctgttgtct  23400
gtgtttgcaa ccatgtatct caatgatatt caacggtctg atttttatgc gtctattgga  23460
cttgatgcac gggactatga taaatatgtc attgagaaga ccaacgaaac agccggccga  23520
gtgttcccca tcgttttaga tgtagataat cctgagtttt acgacagttt agaagtttgc  23580
gtcaagaaca acgaaaagtt acgagaaatt gacgcttcta atagtccgac tcctgtgaag  23640
ttcttgagaa aattacctgc ttttatttct aatggagttc agttcttaaa actttatttc  23700
```

```
atgaaaccca ttcgggttga tcatttagaa ggaactgtcc gttaaaagtt ttgagttagt  23760
ttacgttttg agtacccgct atagcgggtt ttttgtttta atcgggttga caataagcat  23820
tcatttctgt acctaaatct tgttcttttt tacccaattg ttgaacctgt tgctgcatta  23880
atttagcggt atcaatatct ttatccttca atgcagcaac gaattgacgg gttgtatcgg  23940
catttccttg ataaatatca gcgaacccca tttgatattc ttgtaattgt tcatcttcta  24000
tttttaattg tttcatttgt tgggatgttt cttcaaataa atcggctact tgtaagactt  24060
ttttaatatc agttgtttga cgataacttt cactttcttc tgccattttc tgagttaaaa  24120
ggatgatttt ttgacattga gagactttag tttcagcgca acttattaac aataagttta  24180
tcaaaattgt gaatagagat agggttgaag acaggcactt actatttgaa agttttatca  24240
tcgaatgttc ctcacgttta aaagagttct ttgattagaa aaattatgct attcttcctg  24300
gtttgttaaa ctatgtacta aagtatgaat taaataagtt aactgggtga gttgttctct  24360
agactcggtt tgtgcatcga ctagggtttg aatagactca cttaaagcaa aaatctgata  24420
accttgttgt tgaatttgtt gttcttgttg ttgaatttgt tcaactagat tttccatttt  24480
ctccgctaaa ctttctacgg tttcagtggt agcaataacc gtctctccca tacgttctaa  24540
aatcgtttct attttttgag tattttgaac catttttata ttttatattg attatctaaa  24600
tttttaggaa ttgaaataga aaatttaagc attaccgtga cgtttttgat gccattgcca  24660
agcatgatta acaatggttt gaagatcaga atattgaggt tgccaaccta aaactgattg  24720
tgctttttga ctacttccca ctaatattgg gacatctccg ggacggcgat cgctttcttt  24780
cactagaaaa tctattcctg ttactttttt agccatatca atcacctctt taactgaaaa  24840
tccattaccg ttccctaaat taaacatttc actttcaccc ccatttaaaa gatattctaa  24900
tcctaaaata tgagcagatg ctaaatcatt gacatgaata taatctctaa tagctgtgcc  24960
atcatgagta tcataatctg tgccaaaaat aaagagatga tctcgttttt ttagtgcagt  25020
taataaagct aggggaatca aatgcgtttc gggggtgtga tcttctccta aattcccaga  25080
aggatcagcc cctgacgcat taaaatagcg gaagataacg gattttaatc cataagcttg  25140
atcaaaatct ttgagaattt tttctaccat atacttacta gaagcatagg gacttaatgg  25200
gtgattggga tgctgttctg tcatgggaat ttcttgaggc attccataaa tcgcacaggt  25260
agaagaaaag acaaacttgt taatattagc agccatcatc gcttctaata aggttaaggt  25320
tcctactaca ttattttgat aataaatggc aggagcttga accgattctc ctacagcaat  25380
aaaagcagca aagtgcataa cagcagcaat atttcttgta gaaaatagct catctaacag  25440
agtacgattc tgagtatcac ccacaatcaa ttcaacttgt aaaacatctt taataatctc  25500
aggatggcca taggaaagat tatcaaagac aatgacatga tagccagctt tttgtaagga  25560
tagaacagca tgagaaccga tatatccggc ccctcctgtg actaaaatag tgggtttggt  25620
gtctgacaca agcactcctc agcataagtc aagaacgatc ctcttagcga tcgcacttcg  25680
tgggttttac ttacttagga tagggcattt ttacccttaa gaaaagccaa aatcaaggat  25740
cattttggtc tattccctct atactgaaaa atctattcat gtcttctata atacttatta  25800
ttacttaacc atgttagata ccctggatct caaattaact ttagataaag agacttataa  25860
aaccgaaata gaagccttaa tgcgacagtt gcgatcgcta caaaaagact gttgggataa  25920
tcagctacca gtgattattg tcttagaagg gtgggccgca gcagggaagg gaaaattatt  25980
acagaaaacc attggctata tggacccccg tggctttaac gtttatccta ttttagcagc  26040
```

cacagaacaa gagaaaaaat atccttttct ttggcgattt tggcacaatt tacccccaaa 26100
aggaagtatt ggcatttttt atcacagttg gtacacccat gtcttagaag atcgtttatt 26160
tggaatagaa accgatggca gtattccttt gttaatgaga gatattaacg cttttgagag 26220
acaattggtg gatgatggcg tggctatagc taaattttgg atacatttaa gtcaaaaaga 26280
actcaaaaag cgactcaaaa catatgcctc tgatgagttg gaatcatggc gtgttcgtcc 26340
ggaagattgg caacaagcca aagaatatga tcgctatggc acctttgctg aggaaatgtt 26400
aacctatact agtaccggtc atgcgccttg gacattagta gaaggggact gtaaacgttg 26460
ggcaagggtt aaggtattat ctcagattgt agcggttatt acccaagcct tagaccgtct 26520
cagactgcca aaaactgata ttccatcttt accccctcaa acggagttac aacccacaga 26580
accagatttt ttaggaaaaa tagacttagg gttacattta tttaaagatg attataaaca 26640
aaggttacgg gaagcacagg ttaaattaag agagttacag ttacaaattt tcaaaaaaaa 26700
ggttcctgtt ttagtcttat ttgaaggatg ggacgcagcc ggaaaaggag gagcgattaa 26760
acggttaact gataccttag atccaagaag ttataaagtt catgcttttt ctgcccccac 26820
gtctgaagaa ttaaactatc attatttatg gcgattttgg cgacaaattc cagcacaagg 26880
aagcatcgga atttttgatc gaagttggta tggaagagta ttagtcgaaa gggtagaagg 26940
gtttgcatcg gaattggaat ggcgacgctc ttataaagaa attaatgagt ttgaatcgca 27000
gttaacggca tcaggatatg tcatcgttaa gttctggtta catattagtt ttgaagaaca 27060
attaaaacgg tttgaagata gaaaaaataa cccgtttaaa agctataaat taaccgatga 27120
agactggaga aatcgggaaa aatggccatt atattacgtc gcagtcaatc aaatgattgc 27180
ccgtaccagt accccctatg ctccctggac cattgtacct ggaaacgata aatattatgc 27240
ccgtgttcat gtgttagaaa cagtgattca tgccattgaa acggagttga aacaacgaga 27300
ttaattctta caactcatga ttgatgatta aataattcat aagtaaaaca tacagtttta 27360
ataggtaaac agcgatcaat aattgatact tggtcactgc ttactgataa gatgaaattg 27420
cgttatattt gctacaaaag actgcaaacc tgagttcgat ataaggaaat tgatagataa 27480
cgtgtcaaaa taggaagtct caaactctga ttccctcgtt aaacaaatcc gaactcctaa 27540
caccgaactc aggttgcaag ggagtgggga gagagataat ttgtagcatt cttaatttct 27600
attcaatata acgtctcact gataacgact agccagtctg agcataaaag agttatagct 27660
attctcgatg acagtacaaa agacaattca gaagttctta gggacattaa cgaactttta 27720
tcttcataag cttgactttc atagaatttt acgtttacat aaaatctgta atcttactga 27780
tgataccaaa tccgctttag aaagtagaca aataattagg agtatttaag ccagtgataa 27840
ttggtcaagt ttttgatttc ttcagtcata ttttggagca gacaacaacg tatggctagg 27900
atatcttcta tctcctcaat tgtttcaaaa tactcattaa ccaaaggctc atctaccaaa 27960
gtccataatc tttcggctgg ttgtagctct ggagaataag ctggtaaaaa ttctactatt 28020
attccattag gaattttaag tttttggctt cgatgccacc ccgcattatc ttcaactaaa 28080
aaaattattt tatctttatt aagtcctacg tcttcagcaa aagcttcata gactaaactt 28140
aaccatttat tgttgactct cggtattaag taccataagg tttttcctgt tttgggttcc 28200
acaaatccat aaacatataa ccattcgtaa cgatgttgta ctatagcttt tggtctttct 28260
cctgttggac tccaaacttt tctaataatc ggctttaatc ctactcgatg ctcatcgaaa 28320
aaccagactt ctacagtagc ttttttagac ttttcttgta actttttgac ttttaaaggt 28380
agatttttct tgaagaattc ttgctctata ctatccaggg taagctcatc taaaatccgc 28440
ttgacagaag gaattgagaa cagtcatcat atagttgttg ttcatagcag cttgcttcat 28500
tttctggcga agactacgtt taaatgtttt ttcttgatgg agaacattaa gagccaatcg 28560
tcttagaaga gcaaagttct gtggactata ttctgaccga atacggcatt gatcttcaga 28620
aaaagtgaca tcgagtgtcc aatgaaggtt attctcaatg ctccaatggg tgcggatcgc 28680
atggcaaagg aattgggcat tgggaggtaa agaggtcaga taaaactgaa tatcgtgggt 28740
agtcttgttc cacaagtgac ggatgcgttc gactacgaca atagtttgca gtccatgcca 28800
ttgttgttgc tggtaaagct ctcccatagc tgctactggt atagcccaaa cgtatcgttt 28860
ctcggtgcgg tggtggccct tggttacact tttgtagtaa tcatgttcaa tgccatccca 28920
gccattgttt tgggtatcag taaaccattg cttgacttga gaaaataaag taggatggtt 28980
agctttgaga gtaacaatgt agtcagcttt ttgccgacaa atttgttgga taatgctggt 29040
ttgagttccc attgcatcaa tggtaatgat cgagcctgta atgtctaata gttcgagtaa 29100
ggcaggaatg gccgtaattt cattggagta gttttcaact ttgacttgtc ctaacaccag 29160
actctgctgg gatgcccacg ctgtgaccgt atgtaaagcg cactgtccgg cgttgcgatc 29220
gtaagaaccc cttaatgttt tgccatcgat ggggataatt tctccttgaa ttgaattcat 29280
tatagattga acccattttt gtaggcattt ttgcagcgat tctggatcaa ttctctcaaa 29340
aactcttcta aatgtgtcat cactcgggat tccgtgaggg agttctagaa actctgataa 29400
ccactcctgt tttgcgatac catagttctc catatcttcc caaccttggg agcctgcaat 29460
gactgccaat atagcgatcg ccaatacatc tttaaggagg tgtttttgc ttctttgtac 29520
tctaggatct tctatttctt tgacatagcc taataaattg ttttggattt catcaataga 29580
tgctatattt cccttttcct tttttttctt actagattgt ttttggtctg caaacccctt 29640
ggccatgttc tgattccata attacgaaag tcctaattgt actttgtttt tttattttaa 29700
gtccctttttt gcctcaccta gactttactt tcttagtcaa gtacatttta taccatttta 29760
gatgagctta ccctgcaaaa gagtttaaaa ataatgagca aaaaagaaat ttaaaacgca 29820
gacatagccg aaataatcct aatctgaaaa ttagaacata cgatgcacta attaatcaaa 29880
ttaaagatgc tggacaaatt aattacaaat taccttggtt acaaaagcta aaaataaatt 29940
tattaacaac acaatcaaga gatttaagtg gctacaatag taaagtaagc ctaagcccat 30000
atgtcaaatt agaaaaaatg ttcgagtggg acgactcgaa agctaagata aatgaaacca 30060
aacattcagt ttctttccct tttgcaacca gggtttttga tgaccaaaat aggttaacag 30120
tcattgataa acggtttaac tatggtgaag tgcgatatat tactctcgga aaaatagagc 30180
agcgtgttta tgtcgtagct tacaccatca gaggttcagt ggttcgtttg atttcagcaa 30240
gaaaagctaa cagtagagag gtaaaacgtt atgacaacca ttaactacac acctgatcct 30300
gaaaaaaaag ctcaactgag tcaagaacaa ttatcccgtt tggaagaact ttctgatgag 30360
gatatagact attcagatat ccctgaatta gatgacaact tctgggaaaa tgctgagata 30420
gtcaatactg atgttactca aaacacggta tcatctaccc taggaaattt ttaggcgaaa 30480
cacaccccaa tgggtactat tcaaacacta ccaggaacga gagatattct gccagaagag 30540
ataggatact ggcaatatgt agaaactgtg gcgacacaaa tactcagtcg tgccatgtac 30600
tatgaaatac gtccccctat ttttgagcaa acttctttat ttgagagagg gataggcgaa 30660
gcaacggatg ttgttggcaa agaaatgtat actttcagcg atagaggcga tcgctcttta 30720
actctacgtc cggaaggaac tgccggcgtt gtccgtgcct atttacaaaa taatctttat 30780

```
gcagccggtg gagtgcaacg tttgtggtat tgtggcccga tgtttcgcta cgaaagaccc  30840

caagccggtc gtcaacgaca gtttcatcaa attgggttag aattaatcgg tacagccgat  30900

cctagggcag atgtagaggt cattgcttta gctacagata tcttgaagac gttaggatta  30960

caaagtttaa aattagatat taattccgtc ggcgatcgca acgatagaca aaactacaga  31020

gaagcgttag ttaattactt tctcccctac aaagccgaac ttgataccga ctcccaagat  31080

cgtctacaac gcaacccctt acgcattctc gatagtaaag ataaacggac taaagaaatt  31140

aatcaaaatg cgcctagtat tttagaacat cttggagatg cttctaaaaa acactttgat  31200

caagtgcaac aactgttaac ggatcttggc attgaatata acatcaa                31247


<210> SEQ ID NO 2
<211> LENGTH: 1665
<212> TYPE: DNA
<213> ORGANISM: Cyanothece ATCC51142

<400> SEQUENCE: 2

atgagctact gtgtaaaccc atcttgcgcc caacccaaaa accccaataa tgtggcggtt     60

tgtcaatctt gcggttctca actgcgatta aataatcgtt atcaaccctt aggtattctt    120

ggaaaagggg gctttggggc cacctttggg gctgcagata tttcccttcc agggaatccc    180

atttgtgttg ttaagcagtt acgaccagcg acagacgatc ctcaagtcta taaaatggct    240

aaagaattgt ttgaacggga agcagaaact ttaggtaaag tgggaaatca tccccaagtc    300

cccagattat tagactattt tgaacaaaac aaagaatttt atctggttca agaatatgtc    360

aaaggataca atcttcatca agaggtcaaa aaaaaggggc cgtttagcga agcaggggtt    420

aaacagtttt tgacagaact cttacctatt ctagaatata tccattctca gaaagtcatt    480

caccgtgata tcaaaccagc taacctaatc cgttctcaaa aagatagtaa actggtctta    540

attgactttg gagcggtcaa aaatcaggtt aactctatgg ttgcgaataa tacccaaacc    600

gcttttactg cttttgccgt gggaacagca ggttttgccc ctcctgaaca aatggccatg    660

cgtcctgttt acgcgagtga catctatgca gtgggggtta cctgtgtcta tttattaacc    720

gctaaaaccc ccaaagatat tggttgtgac cccgaaacag gggaaattgc ttgggaaccc    780

tatgttaata ttagtgactc tttggccaat gttcttaaaa agatgttgga agtatcggtt    840

aaacatcgct acaaatcagc cgaacaagtc ttagatgcta tggccatggc cccttatgaa    900

caagggatgc aagatagcat gactactatg atcacaggat ttaaaactcc tagtagttcg    960

tcgagtccca actcttcact cagtaccggt ttagtcagtt catccccatc gaccagaact   1020

atgggaagag tcaacaccca tatttctaag ggaagtccca tgtcctcagt ttctccagag   1080

gataaacact ccgtcgctac taagattcaa ggtagggttg cagggtgtgg aaatgctaac   1140

tacaatatag ctcatggaca aacctctagc cgtcgtcgtg gtaaaggaca aggaatctct   1200

aactctgata ccatagcaac taaaaaaaac cagaaaaaat ggcaagaaaa aaccttatta   1260

actgcttatg aaaatggtcg aagagacttt actaatcaag aattaaatga actcaattta   1320

tctaaagctt ttttaccagg aattaattgt tatcaagcca aattaagccg tattaattta   1380

caaggggcag aattaacccg tgcggatctc ggaagagcag atttaaccca agcagtgatg   1440

aaaaatgcca atcttagtga ggcttattta ggatacgcta acttaaatgg agcggattta   1500

agaggggcga atttatgtgg ggccaattta acctatgcta atttacaagg agcaaatctc   1560

tgtggggttg atttaagttc tgcaagaatt actgaggctc aattatctgt agctaaaacc   1620

aattggcgaa cagtaatgcc cagtggtaag cgaggatttt ggtaa                  1665
```

<210> SEQ ID NO 3
<211> LENGTH: 3198
<212> TYPE: DNA
<213> ORGANISM: Cyanothece ATCC51142

<400> SEQUENCE: 3

```
atgagtgagt taaaagaaga tttcagaagc aataataatg gacataatac ctcagtcaat     60
ggcaaaaaaa cctcccgatt agaacgattt ttctttttaa acactatttt tgctatttta    120
ttaaccttgc tcatggtggt ggggggtctt ttgggttatt tttccatgac caaacagtct    180
aaccctgata ttgatattgc cgttgccacc gtcactacca cctggccagg agccgacccc    240
caaaccatag aacaacaagt tacttctgaa attgaaacag aaattacttc agtagaaaat    300
gtcaaagagg ttcaaagtgc ttcttatgca gggttttcgg tgattaatgt cgaatttacg    360
tcccaggccg accccgatga agcgatcgaa gaattacggc aaggggtcgc ccaagccgaa    420
cccgaattac ctgaagaggc agagcaaccc gtagtagaac aaatttccgt caatgatgcc    480
cctatcctta ccttagcctt gtttggggac attgatcaaa cggtgatttc tcaaacagca    540
gaggacattc aagacaattt agaacaggtg gcaggggtca gtgaggtgaa cctaggggga    600
gcgcgagaag aggtcattaa tgtgcaaatg aaccccttc gtttagccac gttgggcatt     660
tctcccacaa cggttgccac agaaattcgt aatgctaacc gagatgtccc cctctcagag    720
atagaaagtg atttaattgg gtcacaggta cgcttttatg ctcgttttcg cagtgtagaa    780
gcattacaag atttacccat cgctcgttta gaggggcgag tagtacgcct cagtgaactg    840
gcagaggtgc gtcgagaact tgaccaagaa gaaacccgtg cctttattag tacccaagga    900
gaagcttatc aacctgtggt gagtgtaggt attaaaaaag tacctggaca agattcgatt    960
gaggttattg aacgggtttt agaggctatg gagcaaattg agcaaaatcc gaatctgtgg   1020
cccagaggca tggaatatca aattattgcc gatgaatcgg atattatttg ggaacagttg   1080
ggcaatttat ttaccaatgc cttgcaagct atggccgccg tgtttgtggt gctgtttatt   1140
gctctttctt ggcgtgaagc cttaattgcc gggttatcca ttcccttaac ctttttggga   1200
gcgttagcgg tgttatggtt aaccggacaa accctcaata atatggtact cattggtatg   1260
gtcttggcct tgggtatctt ggtggatgtt ttcattttgg tgatggaagg gatgcacgag   1320
tttatctttg ctgagggact gtcttttaac caagctgcgt taaaaaccgt taaaacttac   1380
gcaccacccg cttttgcagg acaattgacc accattttag ccctatttcc cttactggcc   1440
attagcggta ctttgggaaa gtttattgaa ttgttaccct acaccgcaat tatttgttta   1500
gtcctcagtt ttgttattgc cattttaatt gatattcctc tgtctcgtta cttgttaggc   1560
aatatgagaa gcgttgaaaa aaaatcaacc attgaccgtt taagtcaagc cgcgtctgct   1620
cgttggatga attggagtct taattatacc gttagaaata aaaaaacggc ttgggcttgg   1680
gtattaggaa ccattgccct ctttttctgt ttcatgacct tatttagtca aatttccgtg   1740
gaatttttc ccagaggcga tcaacgcaac tttagtgtca atgtggaact accccccacc    1800
acaaccctag acgtttccca agaagtagcc gacgacctag gagaaatttt acgagaaaaa   1860
gactatcttg acagcgtgat taaatataca ggacagcgca gtaatttagt ggcatcaggg   1920
gaactacaac ccactcaagg cagttatcta gtgggttttt caggtacgtt ccttcctgaa   1980
aaccaacggg aacggctatc ctttgaatat ttagatgatt tacgcaacga attacaaaaa   2040
gccgttaatc aatatccggg cgcctcttta gtcttaaatg ctcaacaagc aggggaaagt   2100
```

-continued ggggacccta ttcaaattga aattaccggc agtgaattaa gccaactcag ggaaatttct 2160
caacaagtgc aaatgaccct cagacaaata cctggggcga ccgatgtgcg agataattta 2220
ggagccttgc aacctgacct tagattaatt cccaagcgag aagaactgtc attttatgat 2280
ctcagtgaag aagaactggc ttctcaagct caatattata tgcgagcggt agatattggt 2340
gattttgtca tcggtggcaa tgaggaagac ttagaaattc tccttagcac tgcttggccg 2400
tcccgtaacg gcgaagtggg gggacccacc cgtcgagatg agttattatc ggcccgtttc 2460
tttacctcaa acccagagga agaagtgatt tccgcaggag cagtgattga agcagtccaa 2520
gccgaagccc ctttatctat tacccgtcgc ggaggacagc gcactgttac cgtcttggca 2580
aagaatgaaa atcgcactac tggggaaatt ttagcggatt tacagcccaa attacaagaa 2640
atacaagaat cttggcccca aggctatgat tatactttcg gggagagaaac ggaagaccaa 2700 gcggaaacct ttggctctgc cggtcaagcg ttagctttag ctatttttct cgtctttgca 2760
gtgctggtgt tacaactggg atcatttcgt caacccttta tcattttact gaccatcccc 2820
tttgcattga taggaaccgt tgggggcttt ttcctggcag atatcgcctt ttcctttacc 2880
gcttttattg ggattattgc tttagtggga attgtggtca atgatgcgat cgtcatggtt 2940
gataccatga atagttatca acaagaagga ataaaattac gtttagccgc agccaaaggg 3000
gttgctgacc gtttaagacc tgtgctaacc accagtatta ccacgattat cgggttaatt 3060
cctctagctt tgagtgatcc cacttggatg cctttatgta gtgcgattat cttcggttta 3120
gtggcggcta cagtcattgc tttagtggtt attccttgtt tgtacctttt gttcactccc 3180
aggactcaat caacgtga 3198

<210> SEQ ID NO 4
<211> LENGTH: 1572
<212> TYPE: DNA
<213> ORGANISM: Cyanothece ATCC51142

<400> SEQUENCE: 4
atgaatcatc agactcacaa tcctttgccc tcaaatatcc ctccatcaag accccaaaaa 60
tctaatgata ctgagcaatt tctagacaaa aatctaccct cagaatacaa agaaactccg 120
aaaagctctg ataaaaaaga gcagaaaaga aatattaaaa aactatggtg gttattgcca 180
gtatttggtt tattattcgt cctaggggga gtcacagtta ttcgtcttcg agacaatgat 240
cagcctgtca ctgtcaccga aacagtttcc ctttcagtac aggttgccac cgcgacacgg 300
gaacccctcc gggcttggat ctccagtgaa ggcagtgtta gagccgtaga ctatcaacat 360
cttacctttg acacagaagg ggatgttacc tatctggcta accaagacgg tagaagactg 420
cgagaaggcg atcgcgtaac aaaaggacaa ttattagctc gcattgatga tcgcgaactc 480
accgcagatg tcacccaagc ccaagctgcg atcgccgaag cccgacaaaa cagggcggcc 540
gccactgcag acgtagctca agctcgcgcc caggttgctc aagcgcgatc gcaagtacaa 600
gaagcccaag cccaactaca aaatgctcaa gcagcccgaa gattagcagc aaccagttta 660
gaacggtatc gaaccctcgt agaagagggt gcagtggctg aaatcgaatt tgatgaacgt 720
caaaacacct tagaagatgc tcaagcaggg gttcagtcgg ctcaagcagg agtgcagtca 780
gcccagcaac aagtagaagc agcccaagct caagtacaag cagcccaaca acaggtagaa 840
gcccaaacct ccgccattac cacagccgaa gcccgattat ctcaagcaga ggtagcttta 900
gaaggagcca gtatttatgc accttttaat ggcattattg cctatctcaa tatttcagaa 960
ggagaatatt tctctccaca aatcgttacc tctcaactcg ggggagatta tcaagggatt 1020

```
ttagaacgta ttcccatggt tattattgat ccgagtcaat acgaggtcat ggtagattta   1080

gccgggccta caggggaaca agtggaagcc ggtcaaaacg ctgtgattgc ctcagaaacc   1140

caagtcaata ctgcggctac atctcaacag accttaatta ctaacgctcg cgctaggggt   1200

gaagtctttg ccgttaaccc tgccattagt ccggggggac gagccataga agccaccatt   1260

cgtcttaatc caagcaccac cgaaacccta cgacatggag aacaggtgtt aacttggatc   1320

gctgtgtcgg aaaaccccaa cgctgtcact gttcccatcg atgccattgt acgacgcgat   1380

cgcattcctt atgtattcgt ggtgaacgaa gcagaaaata ttgtcgagca gcgagaggta   1440

gaattaggca ttacaggcat tacccaacag ggaattatca caggggtaac acctggggag   1500

ttagtggtca cggaaggaca caaccgactg gtggacgggg cgagtgttga agtgattaac   1560

caaggtagat aa                                                       1572
```

<210> SEQ ID NO 5
<211> LENGTH: 885
<212> TYPE: DNA
<213> ORGANISM: Cyanothece ATCC51142

<400> SEQUENCE: 5

```
atggaaacct cagaactaat tttaaggaca gcacaaaact tatttgatgg cttagccatt     60

ggcagtgtca ttgctctcgc tgcggtgggg ttaaccttga cgtatggtat tttacggctt    120

tctaacttcg ctcacggaga ttttatgacc ttgggagcct atttaacttg gttagccaac    180

actcaaggcc taaatttagg cttatcggtg attatcggtg cgatgggaac cgttttggct    240

atgttagttt cagaatattt attatggaaa cccatgcgcg atcgcagagc aacttcaacc    300

accctaatta ttatctctat tggcttagcc ttatttttgc gtaacggcat tttaatgatt    360

tggggagcga aaaatcaacg gtatgatatt cccttggttc aagcacaaaa actttttggg    420

ttacagttag ccaccgacag aatttgggcg attattttat caattgtagc catcgccatt    480

ttacatttag tgttacaaaa cacaaaaatt ggtaaggcca tgcgagctgt agccgataat    540

attgatttag ctagggtttc aggaattaat gttgaacaag ttgtcctctg gacttgggta    600

attacagcca ttttaaccac cttgggcggt gtcatgttgg gattaattac cagtaccgta    660

cgacctaata tgggatggtt tttaatttta cccatgtttg cctctgtgat tttaggcggt    720

attggcaacc cttatggtgc gatcgctgga ggcttagtta ttggagttgc tcaagaactg    780

agtgtacctt ggttgggacc tgattataaa ttaggagtag ctttattaat tatgatttta    840

attcttttga ttcgtcctca aggcatcttt aaagggactc tttaa                    885
```

<210> SEQ ID NO 6
<211> LENGTH: 525
<212> TYPE: DNA
<213> ORGANISM: Cyanothece ATCC51142

<400> SEQUENCE: 6

```
atggtttttt ggaaacgatt gtttaataat acagatatat caaacacaga ccaaaagtcc     60

cagtttaaag gggagccggt caacttaaaa ggccacactg acggtcaaac gcgtattttt    120

ttcaccagag aaagagaaat cgatctctat gaacttgaag aattatgcga tgcggtagga    180

tgggctcgtc gtcctctgag gaaagttaaa cgcgcactca cctatagttt tatggtagtg    240

tcagcatggg aagtaaaagg aaaccggaag cgtttaattg ggtttgctcg cgctacgtcg    300

gatcacgcct ttaatgccac tatatgggat gtggttatac atccgaggtt ccaaagtaaa    360
```

-continued

```
ggactgggaa aagggatgat gaagtatatg attcgtcaat taagaagcga agatattagt    420

aatattaccc tctttgccga tccccaagtg gtggactttt accgtcgttt ggggtttgta    480

ctagacccag aaggaattaa agggatgttt tggtatcctg attag                    525


<210> SEQ ID NO 7
<211> LENGTH: 465
<212> TYPE: DNA
<213> ORGANISM: Cyanothece ATCC51142

<400> SEQUENCE: 7

atggcagtca atcgtattag aattggtaaa gataaaggag aattagtaca gtctttggtg     60

gatttcaatg gaggagttgg accttttcaa acttatgctg atgtgatcac ctttgcagca    120

acattagggg caaagtacaa caaacgcatt cctctgaata taatttcaaa agaaccggca    180

cccattagct tagaaatctt tgtttctagg gggtacgatg ccgtgataaa attattggca    240

attactgaaa ctaatgatcc tcatattctc tctctttatg acaccgaagc agaaaaccaa    300

agaattcaaa tctttgaaga atacgccaat ggtggccttg aacaattaca agaagaatta    360

aaaggcattg tagattattc agagcattta ttattattgt tgaatttaga aagattcccc    420

aataatacca cagaagagga atttgattta actcgatttc tttga                    465


<210> SEQ ID NO 8
<211> LENGTH: 600
<212> TYPE: DNA
<213> ORGANISM: Cyanothece ATCC51142

<400> SEQUENCE: 8

ttgttgtatt taataattat tttaagaaaa ataatgaatc ccaaagagaa caaaaaaagaa     60

ttgagacaaa aaataataaa aaaacgagag aaattatcaa aaatagattg gatgaataag    120

agcaataaac tgtgtgaaaa tctacaaaat tatcctttat tgcaaaaatc taaaacgatt    180

ctagcttact tttcagttcg ccaagaacct aatttaattt ccctattttc aactgactat    240

aattgggggt ttcctcgctg tgtaaaaaag tctttaatct ggcattcttg gcgcagagaa    300

gatccgctta tacctgggaa atatggcatt ttagaaccgg ctgcgaatgc gcctatttta    360

acccctgaaa aagttgattt aatccttgtt cctgctgtgg cttgtgatta caatggttat    420

cgcttaggct atggtggagg tttctatgat cgcttcttaa attctcctca atggcattct    480

attcctacga ttggcattat ctttgaattt gccctattac ctcaacttcc ttacgaacct    540

tgggatcaga aattacaagc aatttgtaca gaaaatgaaa tcataagcat atctacttaa    600


<210> SEQ ID NO 9
<211> LENGTH: 321
<212> TYPE: DNA
<213> ORGANISM: Cyanothece ATCC51142

<400> SEQUENCE: 9

atgaaacatt ttagagatga atggatacaa gaatggtgtg aagaaaatgg atggacagat     60

ttatttaggg aacgttacaa tcattattgg gcatttcctc caggtgcagt gatgcctgaa    120

cccattccct ctgaagtatt acgattcatt aaagcaacaa aaggcttttg cgcggaagaa    180

agaacctggt taatttcagc tattttagtc tcaattatat ccgttgtgtt gagttatttc    240

ttcaaaaatc ctatgcccat tgtctttgct tttgcttttg ctgctgttac ttcggctaag    300

ttagaagtcg aagagattta a                                              321
```

<210> SEQ ID NO 10
<211> LENGTH: 1566
<212> TYPE: DNA
<213> ORGANISM: Cyanothece ATCC51142

<400> SEQUENCE: 10
gtgtcattat tactaaataa tcgttatcaa gtcattgaaa ccttgggaaa aggggggttt 60
ggggagacat ttctcgccat tgacacccat atgccctcag aaagaaaatg tgtgatcaaa 120
caactgaaac cggcggttca gtctcctgtt attcctgatt ggttaaagga acgatttgcc 180
aaagaagcag ctattttgga agaattaggg gaaaaacatc ctcaaattcc cacattatac 240
gcttattttt ccgaaggagg agatttttat ttagtacaag aatggatcga aggagaaacc 300
ttaacccaaa ttcatcaacg acaaggcaat ttgtcaccta atcaagttag agagatatta 360
ataggtattt tacccgttct tgactatatc cacagtcgtc gtattattca ccgtgatatt 420
aaaccagata acattattat tcgcagtcac gataaaaaac ctgttttaat tgattttggt 480
attgttaaag aaacggtcgc taccatgatt catggggatg ggaatacgcc ttattctgtc 540
ggactgggaa cccctggtta catggcttcc gaacaagcag ccggtcgtcc tctaaattca 600
agtgacttgt atagtttggg actgaccatg gtgtttttac tcacaggaaa aaccccccaa 660
tatttagcca ctgatcccaa tactggggag gtgttatggc gaaaagaagc cccagatatt 720
cagtctaatg tgggaaacgt cattgatcgc gcggttcgtt ttcatcctcg cgatcgcttt 780
tctactgcta aagaaatgtt agaggctttg caggttcccc atactattcc cacggcagct 840
accatagcca ttggacaaca aaatttatct ctatctagaa gttctaccca cactcccatc 900
cctaccaact taccagcaga agcaacagaa acagagacag acaccccttg ggccttgtta 960
gccttaggtt catttttggc agccagtgct atcattggag ggttaatgtt agggatcatg 1020
ttagggacga aagagcgatc gcaaccgact tcttcccctt cggtttcacc tgagtctcca 1080
gaagttccag aaaattctca accagagttt tcccagccca gaccgacact tcggcgacca 1140
gttaggcgtt ctccaggatc gcagtcatct cctactttag aagcgactcc taccccaact 1200
ttagaacctt cccccacact agaagcaact cctaccccaa ctctagaacc ttctcctaac 1260
tcaaccgtac aaccttcccc tactccaaaa gcttcccctt ctccgacttc aacccctatt 1320
ccagaaccca ctaaagttgt tcctattcca gttgaaccac ctccccaagt gtcagaaccc 1380
aaagaaccta ctaaccaaga gggttcagaa ccttctttag tgatccccca tattcctcct 1440
aaacctgctg aagagaaacc gcctaaagaa gaggagaata aacagaatat tcagaaatat 1500
tttgagtctg atagagaaca aaataagtct aatctacaac aatattttga ctctgataga 1560
ccttag 1566

<210> SEQ ID NO 11
<211> LENGTH: 183
<212> TYPE: DNA
<213> ORGANISM: Cyanothece ATCC51142

<400> SEQUENCE: 11
gtgtatatat acctaagaaa aaatatggat gtcgttcgga ttatttgtgc cattatcctt 60
cctccactgg gtgtttttct acaagtgggt attggacccc agttctggat caatattttg 120
ttaacgttat tgggttatat tcctggtatt gttcacgccg tttgggtgat tgctaaaaaa 180
tag 183

<210> SEQ ID NO 12

<211> LENGTH: 345
<212> TYPE: DNA
<213> ORGANISM: Cyanothece ATCC51142

<400> SEQUENCE: 12

```
ttgattatgt cctattcact atctcctcaa gaaaagtcca atacaacttt attttcttta     60
tgtaatcaac ggaaacatca acggtattat aatagtcaag gatcttcggt tgaactactg    120
attgatgggc aagagatcaa acaatcttta aaaggaatga ttattgatga ttcttttagt    180
ggttgtgggt taattattat cggtgaggaa aagttacata ttggtcaatt atgtcgttta    240
agaataaagg gtattgattc cattttatgt caaattattt ggttaagaag attagaaaaa    300
tccattacta ggataggcgt taaatatttg attaaatccg agtaa                    345
```

<210> SEQ ID NO 13
<211> LENGTH: 702
<212> TYPE: DNA
<213> ORGANISM: Cyanothece ATCC51142

<400> SEQUENCE: 13

```
atggttcctt taaatgataa taatcccaca caaagaacag cttatgttac ttatggattg     60
attattctta acgttttagt ttttttcaaa gaactgagtt taagttcgga ggaactatcg    120
caatttttc aatattatgc cattgtccct aaacaattaa ccgcagggtt tagtggagtc     180
gatttttatc atcccattcc tgaatggatg accttattta cgtctcaatt tcttcacgca    240
ggttttttac atattgcagg caatatgttg tttttgtgga tttttggtaa taacgttgaa    300
gataaattag gtcatgttaa atacttgatt ttctatctca cttgtggggt attagctggt    360
ttaagtcaat ggtattttgc cccttattct gaggttcctt ctttgggggc tagtggggcg    420
atcgcagggg tgatgggggc ttacatttta cggtttcccc aagcgcaagt gttaacctta    480
attcctctag gaatttttat tacaacgatt agaattccgg cagtcttctt tttaggattt    540
tggtttttgc aacaagctat ttatggtttt gcgagtttaa atgttcaaac taatgtagga    600
atggaaggcg gtggtgtggc ttattgggcc catgcaggag gatttgtgtt tggatttatc    660
ttaggtccat tattaggatt gttggacgat aagaatcgtt aa                       702
```

<210> SEQ ID NO 14
<211> LENGTH: 486
<212> TYPE: DNA
<213> ORGANISM: Cyanothece ATCC51142

<400> SEQUENCE: 14

```
atggtgaaac gattcattct gatggcgatc gctgctatct ttttcttttt acaatttccc     60
atccataacg ccaatgcctt agaattaacc gaggaaactc ggacagttcc tttaaacgaa    120
gaaggggaaa caatcaccct aaccagtgaa cagatcacaa atggtcaaag actattcatt    180
cgtgaatgta cccaatgtca cttacaagga aaaactaaga ccaataataa tgttagtttg    240
ggattagaag acttatccct ggctgaacct ccccgtgata atgtattagg tttggttgat    300
tatttaaaat atcccaccag ttacgacgga gaagacgact atacagaatt acacgttaat    360
gttagtcgcc ctgatatcta tccagaatta agagacttca ccgaagacga tctttatgat    420
gtgtctggtt atattttagt ggcaccaaaa ttagattctt attggggtgg atcaatctac    480
ttctaa                                                               486
```

<210> SEQ ID NO 15
<211> LENGTH: 96

<212> TYPE: DNA
<213> ORGANISM: Cyanothece ATCC51142

<400> SEQUENCE: 15
ttgcttaggg gagagaatcg atttttatcc ctgaaaaaat cccccattcc ccccagagaa 60
gggaagttta aggatcagga attatggtat cgttga 96

<210> SEQ ID NO 16
<211> LENGTH: 714
<212> TYPE: DNA
<213> ORGANISM: Cyanothece ATCC51142

<400> SEQUENCE: 16
atgtcggcta cttgtgtcat taatggttgg gaaaggccag aaaagacacc catgttaaaa 60
ctctatcatt tgccgatttc ctttaattct cgtcgtgttt ggattgcttt actggaaaaa 120
ggattatcgt ttgagttaat tcccatgaaa ctcaacggcg atcaactaac tccagaattt 180
ttagccctta accctttca tcacatccct gtcctggtgg atgaagcgtt tagcctcttt 240
gaatccctgg ctatcttaga ttatctcgaa gcgaaatatc ccacccccttc cctagttcct 300 agcgaccccc aaggattagg gacagttaag atgattaact tagtgaccct gaatgaatta 360
ttaccagcaa caaccccatt aattcagcat agtatgggat ttattaccct agacgaacag 420
aggatagcca acactaaaga aaaagttgct gtcgttctca actttttga gacatctctc 480 ggcgatcgct cctatatagt tggcaatacc ttaacgttgg ctgacattgt agcaggaaca 540
atggtggggt ttctgcctca gatgggtgtt tctttatctg cctatcctca attaaccgct 600
tggacaaagc aattaagtca acgggaaagt tggcaacaaa cggaaccccca accagaagaa 660 attgacaaat ttcgagaaac catgaagaaa ttaatggctc aacgtggttc ttaa 714

<210> SEQ ID NO 17
<211> LENGTH: 543
<212> TYPE: DNA
<213> ORGANISM: Cyanothece ATCC51142

<400> SEQUENCE: 17
atgacacaag tatctggttc atccgatgtc cccgatatgg ggcgtcgcca atttatgaac 60
ttactcacct ttggaaccat caccggagtc gctgctggtg ctttgtatcc tgtggtgaag 120
tattttatcc ccccttcgag tggtggtgcc ggcggtggta ttactgctaa agatgccctc 180
ggtaatgaca ttatggctag taactttctg gctactcata atggaggcga tcgcgtttta 240
gctcaagggt taaaaggtga tcccacttac ctcgtggtag aaggagaaaa tgctatcgct 300
gactacggta tcaacgccgt ttgtactcac ttaggctgtg tagttccttg gaacgccagc 360
gaagacaagt ttatctgtcc ctgtcatggt tctcaataca atgctcaggg taaagtggta 420
agaggtcctg cccctctgtc tttggcttta gcccatgtta atgtgagcga agacgataaa 480
gtggtgttca gcgaatggac cgaaactgac tttcgcaccg aacaagatcc ctggtgggct 540
taa 543

<210> SEQ ID NO 18
<211> LENGTH: 912
<212> TYPE: DNA
<213> ORGANISM: Cyanothece ATCC51142

<400> SEQUENCE: 18
ttgatcgttg cagcaacagt tgccttattc ataggtaacg tacaaagtgc taatgcttat 60
cctttctggg cccaagaaac tgccccagaa acccctagag aagcgacagg gcgaattgtt 120
tgcgctaact gtcacttagc agaaaaagct gctgaagtag aaattcctca atctgtttta 180
cctgatacag tatttaaggc tgtagtaaaa attccttacg atctcgactc ccaacaagtt 240
ctaggagatg gatcaaaagg tggcctcaat gtgggggctg ttttaatgtt acctgaaggg 300
tttaaaattg ctcccgatga gcgcattcct gaagaaataa aagaagagat gggtagtgtc 360
tacttccagt cctacagcga aggtcaagac aatgtggttc tcgtcggtcc tttacctgga 420
gaacaatatc aagagattat tttccctatc ttatctccag atccctctaa ggataaaaat 480
gttaacttcg gtaagtatca agttcactta ggggctaacc gtggccgggg tcaaatttat 540
cccacaggac aacctagcaa taataacgtc ttcaaagcct ctaacgctgg tactattagc 600
aaaattaccg atcaagaaga tggtagctac attgtcacta ttgcgacggc agaaggagat 660
gtagacgaaa cgatccccgc aggccctcaa ttgatggttt ctgaaggcat ggaagttgaa 720
gcaggacaag ctttaaccaa taatcctaat gtgggtggtt ttggacaaaa agacacagaa 780
gtggttctcc aaagtcctgg ccgcattaaa ggattaattc tcttcttagc tggtatcatg 840
ttagcccaaa ttctcttagt gattaagaag aaacaagtgg aacgagtaca ggctgctgaa 900
atgaactttt aa 912

<210> SEQ ID NO 19
<211> LENGTH: 99
<212> TYPE: DNA
<213> ORGANISM: Cyanothece ATCC51142

<400> SEQUENCE: 19
gtgataatga ttcttattgt cgttgtagcc ttaatctatg aaatcttctc agaagtggtt 60
atcaatgctc cttttgacta caatcctagg gatgaatag 99

<210> SEQ ID NO 20
<211> LENGTH: 933
<212> TYPE: DNA
<213> ORGANISM: Cyanothece ATCC51142

<400> SEQUENCE: 20
ttgactacaa tcctagggat gaatagtatc acaggatgta gttcaagcaa tcctgtcgac 60
tctgggatta ataagagtga caatcaagaa caaagcaaca gtcaagatca attagacatt 120
acggtgagta tcattcccca gaaatatttt gttaagaaaa ttgggggcga tctcgttagg 180
gtgaatgtca tggtagaaca aggggtactc cctcatacct atgaacccaa acctcaacaa 240
ttacaagcgt taagtgaagc ggaggcttat attggtattg ggattccttt tgaaaccgca 300
tggatggatc gcattaagga agcaaacccg aaaatgttga tggttgactc aacacaagga 360
attgatcgat taactatgat agcccatgat caccatgaag aagaagatca tggtcaccat 420
gaggaagaaa ccacccttga tccccatgtt tggttatctc caagattggt aaaaattcaa 480
gcacaaaaaa tttatgaaac tttagtgaaa cttgatccga aacatcagga aacatatcaa 540
actaatctca atagtttttt acaagaaatt gaggaattag accatcaagt taggaataac 600
ttagctaact taaaacaacg taaatttatt gtttttcatc cagcttgggg ttattttgcc 660
gaggaatata acttaacgca agtacccatt gaagtggggg gacaagaacc tagcgcatca 720
gagttaggag acttaataaa agaagctaaa aaagagaata taaaagttat atttgctcaa 780
ccagaattaa gtagtcaagc tgccaaaacc attgctaaag aaattaacgg agaagtctta 840
ttaattagtc ctactgctgc tgattggtct aacaacttac tagaagtttc tcaaaccttt 900
gccaaagtgt taaaagaaga aaataatcaa tag 933

<210> SEQ ID NO 21
<211> LENGTH: 780
<212> TYPE: DNA
<213> ORGANISM: Cyanothece ATCC51142

<400> SEQUENCE: 21
atgaaaactg aagtcattaa tcttagtcat gtttgggcaa aatataatca tagaaatcct 60
attttagaag acattaactt gactatttat gaaggggatt ttgtcggatt aattggtccc 120
aatggaggag gtaaaacaac tttatttaaa gtgttattag gactgataaa accctatcaa 180
ggaactgtaa aaattttagg taatactgtt agtaaaggaa gacgttatat cggttatgtt 240
cctcaattgg tagaattaga tcgagagttc cctgtgcgtg tcgctgatgt tgtacggatg 300
ggaagactcg gaaaacggcg attattgcag cgttataccc ctcaagatga aattatcgtc 360
aatcgtacct tagaacaggt aggaatgata gaattacgca atcgccctat tgctgaatta 420
tccggtggcc aacgtcaacg agtctatatt gcgcgagcat tggcatcaga accccgtata 480
ctattattag acgaaccaac ggctagtgtt gatccccaac gacaaaccag catttacgag 540
ttattgaaag aattaaatca attgattact attgttatga tttctcatga tattggggca 600
atttcagctt atgtcaaaac cgtaggatgt cttaaccatc gcctcttttt tcatggtgat 660
cctcctctga gtaccgaaac aatagaacaa acttatcaat gtcctgtgga tttgatcgca 720
catggggttc ctcatcgggt cctttctaac catgattgtc ccttacatta tcatgaataa 780

<210> SEQ ID NO 22
<211> LENGTH: 816
<212> TYPE: DNA
<213> ORGANISM: Cyanothece ATCC51142

<400> SEQUENCE: 22
atgttagaaa cactttggga atcattacaa tttgatttca tgagaaatgc tctttttgca 60
gggatattag ttagtattgc ttgtggaatt attggcacgt ttgttgtcat taatcgcatt 120
gtttttatta gtggaggtat tgctcacgct gcgtatggtg gtattggctt aggatatttt 180
tttaagatta atcctatttt tggagcaatt ttttttgctt tactttctgc tttaggtatg 240
ggtttagtag tgagaaaaac agaacaaagg gctgacagtt tgataggggt aatgtgggct 300
gtagggatgg cgatcggtat tattttaatt gatttaacgc caggatataa agcggattta 360
atgagttatt tatttgggag tattttaacc gtttctcaag aaaatttaat gatcatgttg 420
gttttagatg tcattattgt gttggttgtt agtttatttt ataaagaatt tttagccatt 480
tcttttgacc ccacctttgc tatgactcgt aatgttcctg tggatagttt atatttatta 540
ttagtcggtg cgatcgcttt aacggtggtg atggtaatgc aggttgtggg gttaatatta 600
gtgattgcat tgttgactat tccggctgcg atcgctggtc aatttttgaa agacataaaa 660
tatattatgt tagtttctat tgtattgggg atgttattta caacggtagg attaatgata 720
tcttatttct ttaacgtaac atctggggcg actattattt tagtttctgg gactgcttat 780
ttaattagtt taggggtaaa aaccttacaa atttag 816

<210> SEQ ID NO 23
<211> LENGTH: 129
<212> TYPE: DNA
<213> ORGANISM: Cyanothece ATCC51142

-continued

<400> SEQUENCE: 23
ttgtgctata gttcaccaga aggtataaaa caaggaagac aagaaggtaa attagctgct 60
aaaattgcct ctattcctcg gttagtcaca ttagaattaa gtgtagaaca aattgctcaa 120
gcattatag 129

<210> SEQ ID NO 24
<211> LENGTH: 267
<212> TYPE: DNA
<213> ORGANISM: Cyanothece ATCC51142

<400> SEQUENCE: 24
ttgccattaa ttagtcgtca ggagatagaa aaaatgttta gtttaagtga tcttagagaa 60
accaaagtgt atcaagaagc attagaagaa ggaatagaaa aagggataga acagggaata 120
gaacaaggaa gacaagaggg agagttagcg gctaaaattg cctctattcc tcgcttagtc 180
gcattaggtt taactataga acaaattgct caagcattag aattagacat tgaacaagtt 240
agtaacattg tcgaatctaa taaataa 267

<210> SEQ ID NO 25
<211> LENGTH: 1065
<212> TYPE: DNA
<213> ORGANISM: Cyanothece ATCC51142

<400> SEQUENCE: 25
atgacaggag ctaacgatac accctatctc cttcgtgctg cacgaggaga aatcttagat 60
cgtccaccag tttggatgat gcgacaagct ggacgctaca tgaaagtata tcgggattta 120
cgggataaat accccagttt tcgtgaaaga tccgaaaatc ctgaccttgc catcgaaatt 180
tctctgcaac cttggcgagc atttcaaccg gatggggtca ttatgttctc tgatatttta 240
accccgttac ctgggatggg tataccttc gatattgtcg aaagcaaagg gcccgttatt 300
gatccaccca ttcgcactaa agaacaagtg gataacttac gtcctttaga tccagaagaa 360
tccttaccct ttatcaaaac tattttacaa agtttacggc aagaagtggg taatcaatct 420
actgtgttag gatttgtcgg atcaccctgg actttggccg cttatgctat tgaaggaaaa 480
agttctaaga attatgccat catcaagagt atggcgtttt ctcaacctga gatcctccat 540
agtttcttga gcaaaatagc cgatgcgatc gctatttatg ttagatatca gatcgactgt 600
ggggcgcaag tagtacagtt gtttgactcc tgggccggtc aactgagtcc ccaagactat 660
gaaacttttg ctctacctta tcaacaacag gtggtgcgtc aggtgaaaga aactcatccc 720
gataccccgt taattcttta tattagcggt agtgctggtg ttttagagag aatgggacag 780
tctggggtcg atattgttag cgttgactgg actgtggata tggccgaagc cagacagcgt 840
ttaggtagag acatgaaggt acaggggaat attgatccag gtgttttatt tgggtcccaa 900
gacttcatta aagcgcgtat tcttgacaca gtacgcaaag ctggaagagg tggccatata 960
ttaaacttag gtcacggtgt tttagtggga actcctgaag ataatgttcg ttgcttcttt 1020
gaaactgcga agcaggtgga tcaattatta gctgttcctg tataa 1065

<210> SEQ ID NO 26
<211> LENGTH: 1107
<212> TYPE: DNA
<213> ORGANISM: Cyanothece ATCC51142

<400> SEQUENCE: 26
ttgattcaaa aaaatccctt taaacaagct atggtcaata cccttcaaaa acctgaattt 60

```
gaggaactcc gtccaggaat taaagttccg gccaaagaaa ctatcctaac ccctcgcttt    120

tacaccaccg attttgaagc gatggcaaaa atggatattt cagtcaacga agaggaatta    180

caagctattc tcgaagagtt tcgcactgat tataaccgtc atcattttat ccgtcgtgaa    240

gaatttgccc aaacctggga tcatattgat ggggataccc gtcgcttgtt tgtagaattt    300

ttagaacgtt cttgtacggc ggaattttca gggttccttc tctacaagga attaggaaga    360

cggttaaagg ataaaagtcc tgttttggcg gaatgtttta ccctcatgtc ccgtgatgaa    420

gcccgtcacg ccggtttcct caataaagcc ttatctgatt ttaatatgtc tttggactta    480

gggtttttaa ccaagagtcg gagttatacc ttcttccaac ctaagtttat tttctatgcc    540

acctatttat ctgaaaaaat tggttattgg cgttatatca ctatttatcg tcacctagaa    600

caacatcccg aagacagaat ctatccgatt ttcaacttct ttgaaaactg gtgtcaagat    660

gaaaaccgtc atggggactt ttttgatgcc atcatgaaag caactcctga cattttaaac    720

gattggaaag cccgtttgtg gtgtcgcttc ttcctgttgt ctgtgtttgc aaccatgtat    780

ctcaatgata ttcaacggtc tgatttttat gcgtctattg gacttgatgc acgggactat    840

gataaatatg tcattgagaa gaccaacgaa acagccggcc gagtgttccc catcgtttta    900

gatgtagata atcctgagtt ttacgacagt ttagaagttt gcgtcaagaa caacgaaaag    960

ttacgagaaa ttgacgcttc taatagtccg actcctgtga agttcttgag aaaattacct   1020

gcttttattt ctaatggagt tcagttctta aaactttatt tcatgaaacc cattcgggtt   1080

gatcatttag aaggaactgt ccgttaa                                       1107
```

<210> SEQ ID NO 27
<211> LENGTH: 444
<212> TYPE: DNA
<213> ORGANISM: Cyanothece ATCC51142

<400> SEQUENCE: 27

```
atgataaaac tttcaaatag taagtgcctg tcttcaaccc tatctctatt cacaattttg     60

ataaacttat tgttaataag ttgcgctgaa actaaagtct ctcaatgtca aaaaatcatc    120

cttttaactc agaaaatggc agaagaaagt gaaagttatc gtcaaacaac tgatattaaa    180

aaagtcttac aagtagccga tttatttgaa gaaacatccc aacaaatgaa acaattaaaa    240

atagaagatg aacaattaca agaatatcaa atggggttcg ctgatattta tcaaggaaat    300

gccgatacaa cccgtcaatt cgttgctgca ttgaaggata aagatattga taccgctaaa    360

ttaatgcagc aacaggttca acaattgggt aaaaaagaac aagatttagg tacagaaatg    420

aatgcttatt gtcaacccga ttaa                                           444
```

<210> SEQ ID NO 28
<211> LENGTH: 285
<212> TYPE: DNA
<213> ORGANISM: Cyanothece ATCC51142

<400> SEQUENCE: 28

```
atggttcaaa atactcaaaa aatagaaacg attttagaac gtatgggaga gacggttatt     60

gctaccactg aaaccgtaga aagtttagcg gagaaaatgg aaaatctagt tgaacaaatt    120

caacaacaag aacaacaaat tcaacaacaa ggttatcaga tttttgcttt aagtgagtct    180

attcaaaccc tagtcgatgc acaaaccgag tctagagaac aactcaccca gttaacttat    240

ttaattcata ctttagtaca tagtttaaca aaccaggaag aatag                    285
```

<210> SEQ ID NO 29
<211> LENGTH: 1011
<212> TYPE: DNA
<213> ORGANISM: Cyanothece ATCC51142

<400> SEQUENCE: 29
gtgcttgtgt cagacaccaa acccactatt ttagtcacag gaggggccgg atatatcggt 60
tctcatgctg ttctatcctt acaaaaagct ggctatcatg tcattgtctt tgataatctt 120
tcctatggcc atcctgagat tattaaagat gttttacaag ttgaattgat tgtgggtgat 180
actcagaatc gtactctgtt agatgagcta ttttctacaa gaaatattgc tgctgttatg 240
cactttgctg cttttattgc tgtaggagaa tcggttcaag ctcctgccat ttattatcaa 300
aataatgtag taggaacctt aaccttatta gaagcgatga tggctgctaa tattaacaag 360
tttgtctttt cttctacctg tgcgatttat ggaatgcctc aagaaattcc catgacagaa 420
cagcatccca atcacccatt aagtccctat gcttctagta agtatatggt agaaaaaatt 480
ctcaaagatt ttgatcaagc ttatggatta aaatccgtta tcttccgcta ttttaatgcg 540
tcaggggctg atccttctgg gaatttagga gaagatcaca cccccgaaac gcatttgatt 600
cccctagctt tattaactgc actaaaaaaa cgagatcatc tctttatttt tggcacagat 660
tatgatactc atgatggcac agctattaga gattatattc atgtcaatga tttagcatct 720
gctcatattt taggattaga atatctttta aatgggggtg aaagtgaaat gtttaattta 780
gggaacggta atggattttc agttaaagag gtgattgata tggctaaaaa agtaacagga 840
atagattttc tagtgaaaga aagcgatcgc cgtcccggag atgtcccaat attagtggga 900
agtagtcaaa aagcacaatc agttttaggt tggcaacctc aatattctga tcttcaaacc 960
attgttaatc atgcttggca atggcatcaa aaacgtcacg gtaatgctta a 1011

<210> SEQ ID NO 30
<211> LENGTH: 1560
<212> TYPE: DNA
<213> ORGANISM: Cyanothece ATCC51142

<400> SEQUENCE: 30
ttggtctatt ccctctatac tgaaaaatct attcatgtct tctataatac ttattattac 60
ttaaccatgt tagataccct ggatctcaaa ttaactttag ataaagagac ttataaaacc 120
gaaatagaag ccttaatgcg acagttgcga tcgctacaaa aagactgttg ggataatcag 180
ctaccagtga ttattgtctt agaagggtgg gccgcagcag ggaagggaaa attattacag 240
aaaaccattg gctatatgga cccccgtggc tttaacgttt atcctatttt agcagccaca 300
gaacaagaga aaaaatatcc ttttctttgg cgattttggc acaatttacc cccaaaagga 360
agtattggca ttttttatca cagttggtac acccatgtct tagaagatcg tttatttgga 420
atagaaaccg atggcagtat tcctttgtta atgagagata ttaacgcttt tgagagacaa 480
ttggtggatg atggcgtggc tatagctaaa ttttggatac atttaagtca aaaagaactc 540
aaaaagcgac tcaaaacata tgcctctgat gagttggaat catggcgtgt tcgtccggaa 600
gattggcaac aagccaaaga atatgatcgc tatggcacct ttgctgagga aatgttaacc 660
tatactagta ccggtcatgc gccttggaca ttagtagaag gggactgtaa acgttgggca 720
agggttaagg tattatctca gattgtagcg gttattaccc aagccttaga ccgtctcaga 780
ctgccaaaaa ctgatattcc atctttaccc cctcaaacgg agttacaacc cacagaacca 840 gatttttag gaaaaataga cttagggtta catttattta aagatgatta taaacaaagg 900
ttacgggaag cacaggttaa attaagagag ttacagttac aaattttcaa aaaaaaggtt 960
cctgttttag tcttatttga aggatgggac gcagccggaa aaggaggagc gattaaacgg 1020
ttaactgata ccttagatcc aagaagttat aaagttcatg ctttttctgc ccccacgtct 1080
gaagaattaa actatcatta tttatggcga ttttggcgac aaattccagc acaaggaagc 1140
atcggaattt ttgatcgaag ttggtatgga agagtattag tcgaaagggt agaagggttt 1200
gcatcggaat tggaatggcg acgctcttat aaagaaatta atgagtttga atcgcagtta 1260
acggcatcag gatatgtcat cgttaagttc tggttacata ttagttttga agaacaatta 1320
aaacggtttg aagatagaaa aaataacccg tttaaaagct ataaattaac cgatgaagac 1380
tggagaaatc gggaaaaatg gccattatat tacgtcgcag tcaatcaaat gattgcccgt 1440
accagtaccc cctatgctcc ctggaccatt gtacctggaa acgataaata ttatgcccgt 1500
gttcatgtgt tagaaacagt gattcatgcc attgaaacgg agttgaaaca acgagattaa 1560

<210> SEQ ID NO 31
<211> LENGTH: 387
<212> TYPE: DNA
<213> ORGANISM: Cyanothece ATCC51142

<400> SEQUENCE: 31
gtggaaccca aaacaggaaa aaccttatgg tacttaatac cgagagtcaa caataaatgg 60
ttaagtttag tctatgaagc ttttgctgaa gacgtaggac ttaataaaga taaaataatt 120
tttttagttg aagataatgc ggggtggcat cgaagccaaa aacttaaaat tcctaatgga 180
ataatagtag aatttttacc agcttattct ccagagctac aaccagccga aagattatgg 240
actttggtag atgagccttt ggttaatgag tattttgaaa caattgagga gatagaagat 300
atcctagcca tacgttgttg tctgctccaa aatatgactg aagaaatcaa aaacttgacc 360
aattatcact ggcttaaata ctcctaa 387

<210> SEQ ID NO 32
<211> LENGTH: 1221
<212> TYPE: DNA
<213> ORGANISM: Cyanothece ATCC51142

<400> SEQUENCE: 32
atggccaagg ggtttgcaga ccaaaaacaa tctagtaaga aaaaaaagga aaagggaaat 60
atagcatcta ttgatgaaat ccaaaacaat ttattaggct atgtcaaaga aatagaagat 120
cctagagtac aaagaagcaa aaaacacctc cttaaagatg tattggcgat cgctatattg 180
gcagtcattg caggctccca aggttgggaa gatatggaga actatggtat cgcaaaacag 240
gagtggttat cagagtttct agaactccct cacggaatcc cgagtgatga cacatttaga 300
agagtttttg agagaattga tccagaatcg ctgcaaaaat gcctacaaaa atgggttcaa 360
tctataatga attcaattca aggagaaatt atccccatcg atggcaaaac attaaggggt 420
tcttacgatc gcaacgccgg acagtgcgct ttacatacgg tcacagcgtg ggcatcccag 480
cagagtctgg tgttaggaca agtcaaagtt gaaaactact ccaatgaaat tacggccatt 540
cctgccttac tcgaactatt agacattaca ggctcgatca ttaccattga tgcaatggga 600
actcaaacca gcattatcca acaaatttgt cggcaaaaag ctgactacat tgttactctc 660
aaagctaacc atcctacttt attttctcaa gtcaagcaat ggtttactga tacccaaaac 720
aatggctggg atggcattga acatgattac tacaaaagtg taaccaaggg ccaccaccgc 780

-continued

```
accgagaaac gatacgtttg ggctatacca gtagcagcta tgggagagct ttaccagcaa    840

caacaatggc atggactgca aactattgtc gtagtcgaac gcatccgtca cttgtggaac    900

aagactaccc acgatattca gttttatctg acctctttac ctcccaatgc ccaattcctt    960

tgccatgcga tccgcaccca ttggagcatt gagaataacc ttcattggac actcgatgtc   1020

actttttctg aagatcaatg ccgtattcgg tcagaatata gtccacagaa ctttgctctt   1080

ctaagacgat tggctcttaa tgttctccat caagaaaaaa catttaaacg tagtcttcgc   1140

cagaaaatga agcaagctgc tatgaacaac aactatatga tgactgttct caattccttc   1200

tgtcaagcgg attttagatg a                                             1221


<210> SEQ ID NO 33
<211> LENGTH: 204
<212> TYPE: DNA
<213> ORGANISM: Cyanothece ATCC51142

<400> SEQUENCE: 33

atgacaacca ttaactacac acctgatcct gaaaaaaaag ctcaactgag tcaagaacaa     60

ttatcccgtt tggaagaact ttctgatgag gatatagact attcagatat ccctgaatta    120

gatgacaact tctgggaaaa tgctgagata gtcaatactg atgttactca aaacacggta    180

tcatctaccc taggaaattt ttag                                           204


<210> SEQ ID NO 34
<211> LENGTH: 554
<212> TYPE: PRT
<213> ORGANISM: Cyanothece ATCC51142

<400> SEQUENCE: 34

Met Ser Tyr Cys Val Asn Pro Ser Cys Ala Gln Pro Lys Asn Pro Asn
1               5                   10                  15

Asn Val Ala Val Cys Gln Ser Cys Gly Ser Gln Leu Arg Leu Asn Asn
            20                  25                  30

Arg Tyr Gln Pro Leu Gly Ile Leu Gly Lys Gly Gly Phe Gly Ala Thr
        35                  40                  45

Phe Gly Ala Ala Asp Ile Ser Leu Pro Gly Asn Pro Ile Cys Val Val
    50                  55                  60

Lys Gln Leu Arg Pro Ala Thr Asp Asp Pro Gln Val Tyr Lys Met Ala
65                  70                  75                  80

Lys Glu Leu Phe Glu Arg Glu Ala Glu Thr Leu Gly Lys Val Gly Asn
                85                  90                  95

His Pro Gln Val Pro Arg Leu Leu Asp Tyr Phe Glu Gln Asn Lys Glu
            100                 105                 110

Phe Tyr Leu Val Gln Glu Tyr Val Lys Gly Tyr Asn Leu His Gln Glu
        115                 120                 125

Val Lys Lys Lys Gly Pro Phe Ser Glu Ala Gly Val Lys Gln Phe Leu
    130                 135                 140

Thr Glu Leu Leu Pro Ile Leu Glu Tyr Ile His Ser Gln Lys Val Ile
145                 150                 155                 160

His Arg Asp Ile Lys Pro Ala Asn Leu Ile Arg Ser Gln Lys Asp Ser
                165                 170                 175

Lys Leu Val Leu Ile Asp Phe Gly Ala Val Lys Asn Gln Val Asn Ser
            180                 185                 190

Met Val Ala Asn Asn Thr Gln Thr Ala Phe Thr Ala Phe Ala Val Gly
        195                 200                 205
```

-continued

Thr Ala Gly Phe Ala Pro Pro Glu Gln Met Ala Met Arg Pro Val Tyr
    210                 215                 220

Ala Ser Asp Ile Tyr Ala Val Gly Val Thr Cys Val Tyr Leu Leu Thr
225                 230                 235                 240

Ala Lys Thr Pro Lys Asp Ile Gly Cys Asp Pro Glu Thr Gly Glu Ile
                245                 250                 255

Ala Trp Glu Pro Tyr Val Asn Ile Ser Asp Ser Leu Ala Asn Val Leu
            260                 265                 270

Lys Lys Met Leu Glu Val Ser Val Lys His Arg Tyr Lys Ser Ala Glu
        275                 280                 285

Gln Val Leu Asp Ala Met Ala Met Ala Pro Tyr Glu Gln Gly Met Gln
    290                 295                 300

Asp Ser Met Thr Thr Met Ile Thr Gly Phe Lys Thr Pro Ser Ser Ser
305                 310                 315                 320

Ser Ser Pro Asn Ser Ser Leu Ser Thr Gly Leu Val Ser Ser Ser Pro
                325                 330                 335

Ser Thr Arg Thr Met Gly Arg Val Asn Thr His Ile Ser Lys Gly Ser
            340                 345                 350

Pro Met Ser Ser Val Ser Pro Glu Asp Lys His Ser Val Ala Thr Lys
        355                 360                 365

Ile Gln Gly Arg Val Ala Gly Cys Gly Asn Ala Asn Tyr Asn Ile Ala
    370                 375                 380

His Gly Gln Thr Ser Ser Arg Arg Arg Gly Lys Gly Gln Gly Ile Ser
385                 390                 395                 400

Asn Ser Asp Thr Ile Ala Thr Lys Lys Asn Gln Lys Lys Trp Gln Glu
                405                 410                 415

Lys Thr Leu Leu Thr Ala Tyr Glu Asn Gly Arg Arg Asp Phe Thr Asn
            420                 425                 430

Gln Glu Leu Asn Glu Leu Asn Leu Ser Lys Ala Phe Leu Pro Gly Ile
        435                 440                 445

Asn Cys Tyr Gln Ala Lys Leu Ser Arg Ile Asn Leu Gln Gly Ala Glu
    450                 455                 460

Leu Thr Arg Ala Asp Leu Gly Arg Ala Asp Leu Thr Gln Ala Val Met
465                 470                 475                 480

Lys Asn Ala Asn Leu Ser Glu Ala Tyr Leu Gly Tyr Ala Asn Leu Asn
                485                 490                 495

Gly Ala Asp Leu Arg Gly Ala Asn Leu Cys Gly Ala Asn Leu Thr Tyr
            500                 505                 510

Ala Asn Leu Gln Gly Ala Asn Leu Cys Gly Val Asp Leu Ser Ser Ala
        515                 520                 525

Arg Ile Thr Glu Ala Gln Leu Ser Val Ala Lys Thr Asn Trp Arg Thr
    530                 535                 540

Val Met Pro Ser Gly Lys Arg Gly Phe Trp
545                 550

<210> SEQ ID NO 35
<211> LENGTH: 1065
<212> TYPE: PRT
<213> ORGANISM: Cyanothece ATCC51142

<400> SEQUENCE: 35

Met Ser Glu Leu Lys Glu Asp Phe Arg Ser Asn Asn Asn Gly His Asn
1               5                   10                  15

Thr Ser Val Asn Gly Lys Lys Thr Ser Arg Leu Glu Arg Phe Phe Phe
            20                  25                  30

-continued

```
Leu Asn Thr Ile Phe Ala Ile Leu Leu Thr Leu Leu Met Val Val Gly
        35                  40                  45

Gly Leu Leu Gly Tyr Phe Ser Met Thr Lys Gln Ser Asn Pro Asp Ile
    50                  55                  60

Asp Ile Ala Val Ala Thr Val Thr Thr Thr Trp Pro Gly Ala Asp Pro
65                  70                  75                  80

Gln Thr Ile Glu Gln Gln Val Thr Ser Glu Ile Glu Thr Glu Ile Thr
                85                  90                  95

Ser Val Glu Asn Val Lys Glu Val Gln Ser Ala Ser Tyr Ala Gly Phe
            100                 105                 110

Ser Val Ile Asn Val Glu Phe Thr Ser Gln Ala Asp Pro Asp Glu Ala
        115                 120                 125

Ile Glu Glu Leu Arg Gln Gly Val Ala Gln Ala Glu Pro Glu Leu Pro
    130                 135                 140

Glu Glu Ala Glu Gln Pro Val Val Glu Gln Ile Ser Val Asn Asp Ala
145                 150                 155                 160

Pro Ile Leu Thr Leu Ala Leu Phe Gly Asp Ile Asp Gln Thr Val Ile
                165                 170                 175

Ser Gln Thr Ala Glu Asp Ile Gln Asp Asn Leu Glu Gln Val Ala Gly
            180                 185                 190

Val Ser Glu Val Asn Leu Gly Gly Ala Arg Glu Glu Val Ile Asn Val
        195                 200                 205

Gln Met Asn Pro Phe Arg Leu Ala Thr Leu Gly Ile Ser Pro Thr Thr
    210                 215                 220

Val Ala Thr Glu Ile Arg Asn Ala Asn Arg Asp Val Pro Leu Ser Glu
225                 230                 235                 240

Ile Glu Ser Asp Leu Ile Gly Ser Gln Val Arg Phe Tyr Ala Arg Phe
                245                 250                 255

Arg Ser Val Glu Ala Leu Gln Asp Leu Pro Ile Ala Arg Leu Glu Gly
            260                 265                 270

Arg Val Val Arg Leu Ser Glu Leu Ala Glu Val Arg Arg Glu Leu Asp
        275                 280                 285

Gln Glu Glu Thr Arg Ala Phe Ile Ser Thr Gln Gly Glu Ala Tyr Gln
    290                 295                 300

Pro Val Val Ser Val Gly Ile Lys Lys Val Pro Gly Gln Asp Ser Ile
305                 310                 315                 320

Glu Val Ile Glu Arg Val Leu Glu Ala Met Glu Gln Ile Glu Gln Asn
                325                 330                 335

Pro Asn Leu Trp Pro Arg Gly Met Glu Tyr Gln Ile Ile Ala Asp Glu
            340                 345                 350

Ser Asp Ile Ile Trp Glu Gln Leu Gly Asn Leu Phe Thr Asn Ala Leu
        355                 360                 365

Gln Ala Met Ala Ala Val Phe Val Val Leu Phe Ile Ala Leu Ser Trp
    370                 375                 380

Arg Glu Ala Leu Ile Ala Gly Leu Ser Ile Pro Leu Thr Phe Leu Gly
385                 390                 395                 400

Ala Leu Ala Val Leu Trp Leu Thr Gly Gln Thr Leu Asn Asn Met Val
                405                 410                 415

Leu Ile Gly Met Val Leu Ala Leu Gly Ile Leu Val Asp Val Phe Ile
            420                 425                 430

Leu Val Met Glu Gly Met His Glu Phe Ile Phe Ala Glu Gly Leu Ser
        435                 440                 445
```

-continued

```
Phe Asn Gln Ala Ala Leu Lys Thr Val Lys Thr Tyr Ala Pro Pro Ala
    450                 455                 460

Phe Ala Gly Gln Leu Thr Thr Ile Leu Ala Leu Phe Pro Leu Leu Ala
465                 470                 475                 480

Ile Ser Gly Thr Leu Gly Lys Phe Ile Glu Leu Leu Pro Tyr Thr Ala
                485                 490                 495

Ile Ile Cys Leu Val Leu Ser Phe Val Ile Ala Ile Leu Ile Asp Ile
            500                 505                 510

Pro Leu Ser Arg Tyr Leu Leu Gly Asn Met Arg Ser Val Glu Lys Lys
        515                 520                 525

Ser Thr Ile Asp Arg Leu Ser Gln Ala Ala Ser Ala Arg Trp Met Asn
    530                 535                 540

Trp Ser Leu Asn Tyr Thr Val Arg Asn Lys Lys Thr Ala Trp Ala Trp
545                 550                 555                 560

Val Leu Gly Thr Ile Ala Leu Phe Phe Cys Phe Met Thr Leu Phe Ser
                565                 570                 575

Gln Ile Ser Val Glu Phe Phe Pro Arg Gly Asp Gln Arg Asn Phe Ser
            580                 585                 590

Val Asn Val Glu Leu Pro Pro Thr Thr Thr Leu Asp Val Ser Gln Glu
        595                 600                 605

Val Ala Asp Asp Leu Gly Glu Ile Leu Arg Glu Lys Asp Tyr Leu Asp
    610                 615                 620

Ser Val Ile Lys Tyr Thr Gly Gln Arg Ser Asn Leu Val Ala Ser Gly
625                 630                 635                 640

Glu Leu Gln Pro Thr Gln Gly Ser Tyr Leu Val Gly Phe Ser Gly Thr
                645                 650                 655

Phe Leu Pro Glu Asn Gln Arg Glu Arg Leu Ser Phe Glu Tyr Leu Asp
            660                 665                 670

Asp Leu Arg Asn Glu Leu Gln Lys Ala Val Asn Gln Tyr Pro Gly Ala
        675                 680                 685

Ser Leu Val Leu Asn Ala Gln Gln Ala Gly Glu Ser Gly Asp Pro Ile
    690                 695                 700

Gln Ile Glu Ile Thr Gly Ser Glu Leu Ser Gln Leu Arg Glu Ile Ser
705                 710                 715                 720

Gln Gln Val Gln Met Thr Leu Arg Gln Ile Pro Gly Ala Thr Asp Val
                725                 730                 735

Arg Asp Asn Leu Gly Ala Leu Gln Pro Asp Leu Arg Leu Ile Pro Lys
            740                 745                 750

Arg Glu Glu Leu Ser Phe Tyr Asp Leu Ser Glu Glu Glu Leu Ala Ser
        755                 760                 765

Gln Ala Gln Tyr Tyr Met Arg Ala Val Asp Ile Gly Asp Phe Val Ile
    770                 775                 780

Gly Gly Asn Glu Glu Asp Leu Glu Ile Leu Leu Ser Thr Ala Trp Pro
785                 790                 795                 800

Ser Arg Asn Gly Glu Val Gly Gly Pro Thr Arg Arg Asp Glu Leu Leu
                805                 810                 815

Ser Ala Arg Phe Phe Thr Ser Asn Pro Glu Glu Glu Val Ile Ser Ala
            820                 825                 830

Gly Ala Val Ile Glu Ala Val Gln Ala Glu Ala Pro Leu Ser Ile Thr
        835                 840                 845

Arg Arg Gly Gly Gln Arg Thr Val Thr Val Leu Ala Lys Asn Glu Asn
    850                 855                 860

Arg Thr Thr Gly Glu Ile Leu Ala Asp Leu Gln Pro Lys Leu Gln Glu
```

```
865                 870                 875                 880

Ile Gln Glu Ser Trp Pro Gln Gly Tyr Asp Tyr Thr Phe Gly Gly Glu
                885                 890                 895

Thr Glu Asp Gln Ala Glu Thr Phe Gly Ser Ala Gly Gln Ala Leu Ala
            900                 905                 910

Leu Ala Ile Phe Leu Val Phe Ala Val Leu Val Leu Gln Leu Gly Ser
        915                 920                 925

Phe Arg Gln Pro Phe Ile Ile Leu Leu Thr Ile Pro Phe Ala Leu Ile
    930                 935                 940

Gly Thr Val Gly Gly Phe Phe Leu Ala Asp Ile Ala Phe Ser Phe Thr
945                 950                 955                 960

Ala Phe Ile Gly Ile Ile Ala Leu Val Gly Ile Val Val Asn Asp Ala
                965                 970                 975

Ile Val Met Val Asp Thr Met Asn Ser Tyr Gln Gln Glu Gly Ile Lys
            980                 985                 990

Leu Arg Leu Ala Ala Ala Lys Gly  Val Ala Asp Arg Leu  Arg Pro Val
        995                 1000                1005

Leu Thr  Thr Ser Ile Thr Thr  Ile Ile Gly Leu Ile  Pro Leu Ala
    1010                1015                1020

Leu Ser  Asp Pro Thr Trp Met  Pro Leu Cys Ser Ala  Ile Ile Phe
    1025                1030                1035

Gly Leu  Val Ala Ala Thr Val  Ile Ala Leu Val Val  Ile Pro Cys
    1040                1045                1050

Leu Tyr  Leu Leu Phe Thr Pro  Arg Thr Gln Ser Thr
    1055                1060                1065


<210> SEQ ID NO 36
<211> LENGTH: 523
<212> TYPE: PRT
<213> ORGANISM: Cyanothece ATCC51142

<400> SEQUENCE: 36

Met Asn His Gln Thr His Asn Pro Leu Pro Ser Asn Ile Pro Pro Ser
1               5                   10                  15

Arg Pro Gln Lys Ser Asn Asp Thr Glu Gln Phe Leu Asp Lys Asn Leu
            20                  25                  30

Pro Ser Glu Tyr Lys Glu Thr Pro Lys Ser Ser Asp Lys Lys Glu Gln
        35                  40                  45

Lys Arg Asn Ile Lys Lys Leu Trp Trp Leu Leu Pro Val Phe Gly Leu
    50                  55                  60

Leu Phe Val Leu Gly Gly Val Thr Val Ile Arg Leu Arg Asp Asn Asp
65                  70                  75                  80

Gln Pro Val Thr Val Thr Glu Thr Val Ser Leu Ser Val Gln Val Ala
                85                  90                  95

Thr Ala Thr Arg Glu Pro Leu Arg Ala Trp Ile Ser Ser Glu Gly Ser
            100                 105                 110

Val Arg Ala Val Asp Tyr Gln His Leu Thr Phe Asp Thr Glu Gly Asp
        115                 120                 125

Val Thr Tyr Leu Ala Asn Gln Asp Gly Arg Arg Leu Arg Glu Gly Asp
    130                 135                 140

Arg Val Thr Lys Gly Gln Leu Leu Ala Arg Ile Asp Asp Arg Glu Leu
145                 150                 155                 160

Thr Ala Asp Val Thr Gln Ala Gln Ala Ala Ile Ala Glu Ala Arg Gln
                165                 170                 175
```

```
Asn Arg Ala Ala Ala Thr Ala Asp Val Ala Gln Ala Arg Ala Gln Val
            180                 185                 190

Ala Gln Ala Arg Ser Gln Val Gln Glu Ala Gln Ala Gln Leu Gln Asn
        195                 200                 205

Ala Gln Ala Ala Arg Arg Leu Ala Ala Thr Ser Leu Glu Arg Tyr Arg
    210                 215                 220

Thr Leu Val Glu Glu Gly Ala Val Ala Glu Ile Glu Phe Asp Glu Arg
225                 230                 235                 240

Gln Asn Thr Leu Glu Asp Ala Gln Ala Gly Val Gln Ser Ala Gln Ala
                245                 250                 255

Gly Val Gln Ser Ala Gln Gln Gln Val Glu Ala Ala Gln Ala Gln Val
            260                 265                 270

Gln Ala Ala Gln Gln Gln Val Glu Ala Gln Thr Ser Ala Ile Thr Thr
        275                 280                 285

Ala Glu Ala Arg Leu Ser Gln Ala Glu Val Ala Leu Glu Gly Ala Ser
    290                 295                 300

Ile Tyr Ala Pro Phe Asn Gly Ile Ile Ala Tyr Leu Asn Ile Ser Glu
305                 310                 315                 320

Gly Glu Tyr Phe Ser Pro Gln Ile Val Thr Ser Gln Leu Gly Gly Asp
                325                 330                 335

Tyr Gln Gly Ile Leu Glu Arg Ile Pro Met Val Ile Ile Asp Pro Ser
            340                 345                 350

Gln Tyr Glu Val Met Val Asp Leu Ala Gly Pro Thr Gly Glu Gln Val
        355                 360                 365

Glu Ala Gly Gln Asn Ala Val Ile Ala Ser Glu Thr Gln Val Asn Thr
    370                 375                 380

Ala Ala Thr Ser Gln Gln Thr Leu Ile Thr Asn Ala Arg Ala Arg Gly
385                 390                 395                 400

Glu Val Phe Ala Val Asn Pro Ala Ile Ser Pro Gly Gly Arg Ala Ile
                405                 410                 415

Glu Ala Thr Ile Arg Leu Asn Pro Ser Thr Thr Glu Thr Leu Arg His
            420                 425                 430

Gly Glu Gln Val Leu Thr Trp Ile Ala Val Ser Glu Asn Pro Asn Ala
        435                 440                 445

Val Thr Val Pro Ile Asp Ala Ile Val Arg Arg Asp Arg Ile Pro Tyr
    450                 455                 460

Val Phe Val Val Asn Glu Ala Glu Asn Ile Val Glu Gln Arg Glu Val
465                 470                 475                 480

Glu Leu Gly Ile Thr Gly Ile Thr Gln Gln Gly Ile Ile Thr Gly Val
                485                 490                 495

Thr Pro Gly Glu Leu Val Val Thr Glu Gly His Asn Arg Leu Val Asp
            500                 505                 510

Gly Ala Ser Val Glu Val Ile Asn Gln Gly Arg
        515                 520
```

<210> SEQ ID NO 37
<211> LENGTH: 294
<212> TYPE: PRT
<213> ORGANISM: Cyanothece ATCC51142

<400> SEQUENCE: 37

```
Met Glu Thr Ser Glu Leu Ile Leu Arg Thr Ala Gln Asn Leu Phe Asp
1               5                   10                  15

Gly Leu Ala Ile Gly Ser Val Ile Ala Leu Ala Ala Val Gly Leu Thr
            20                  25                  30
```

```
Leu Thr Tyr Gly Ile Leu Arg Leu Ser Asn Phe Ala His Gly Asp Phe
        35                  40                  45

Met Thr Leu Gly Ala Tyr Leu Thr Trp Leu Ala Asn Thr Gln Gly Leu
    50                  55                  60

Asn Leu Gly Leu Ser Val Ile Ile Gly Ala Met Gly Thr Val Leu Ala
65                  70                  75                  80

Met Leu Val Ser Glu Tyr Leu Leu Trp Lys Pro Met Arg Asp Arg Arg
                85                  90                  95

Ala Thr Ser Thr Thr Leu Ile Ile Ile Ser Ile Gly Leu Ala Leu Phe
            100                 105                 110

Leu Arg Asn Gly Ile Leu Met Ile Trp Gly Ala Lys Asn Gln Arg Tyr
        115                 120                 125

Asp Ile Pro Leu Val Gln Ala Gln Lys Leu Phe Gly Leu Gln Leu Ala
    130                 135                 140

Thr Asp Arg Ile Trp Ala Ile Ile Leu Ser Ile Val Ala Ile Ala Ile
145                 150                 155                 160

Leu His Leu Val Leu Gln Asn Thr Lys Ile Gly Lys Ala Met Arg Ala
                165                 170                 175

Val Ala Asp Asn Ile Asp Leu Ala Arg Val Ser Gly Ile Asn Val Glu
            180                 185                 190

Gln Val Val Leu Trp Thr Trp Val Ile Thr Ala Ile Leu Thr Thr Leu
        195                 200                 205

Gly Gly Val Met Leu Gly Leu Ile Thr Ser Thr Val Arg Pro Asn Met
    210                 215                 220

Gly Trp Phe Leu Ile Leu Pro Met Phe Ala Ser Val Ile Leu Gly Gly
225                 230                 235                 240

Ile Gly Asn Pro Tyr Gly Ala Ile Ala Gly Gly Leu Val Ile Gly Val
                245                 250                 255

Ala Gln Glu Leu Ser Val Pro Trp Leu Gly Pro Asp Tyr Lys Leu Gly
            260                 265                 270

Val Ala Leu Leu Ile Met Ile Leu Ile Leu Leu Ile Arg Pro Gln Gly
        275                 280                 285

Ile Phe Lys Gly Thr Leu
    290
```

<210> SEQ ID NO 38
<211> LENGTH: 174
<212> TYPE: PRT
<213> ORGANISM: Cyanothece ATCC51142

<400> SEQUENCE: 38

```
Met Val Phe Trp Lys Arg Leu Phe Asn Asn Thr Asp Ile Ser Asn Thr
1               5                   10                  15

Asp Gln Lys Ser Gln Phe Lys Gly Glu Pro Val Asn Leu Lys Gly His
            20                  25                  30

Thr Asp Gly Gln Thr Arg Ile Phe Phe Thr Arg Glu Arg Glu Ile Asp
        35                  40                  45

Leu Tyr Glu Leu Glu Glu Leu Cys Asp Ala Val Gly Trp Ala Arg Arg
    50                  55                  60

Pro Leu Arg Lys Val Lys Arg Ala Leu Thr Tyr Ser Phe Met Val Val
65                  70                  75                  80

Ser Ala Trp Glu Val Lys Gly Asn Arg Lys Arg Leu Ile Gly Phe Ala
                85                  90                  95

Arg Ala Thr Ser Asp His Ala Phe Asn Ala Thr Ile Trp Asp Val Val
```

```
            100                 105                 110

Ile His Pro Arg Phe Gln Ser Lys Gly Leu Gly Lys Gly Met Met Lys
        115                 120                 125

Tyr Met Ile Arg Gln Leu Arg Ser Glu Asp Ile Ser Asn Ile Thr Leu
    130                 135                 140

Phe Ala Asp Pro Gln Val Val Asp Phe Tyr Arg Arg Leu Gly Phe Val
145                 150                 155                 160

Leu Asp Pro Glu Gly Ile Lys Gly Met Phe Trp Tyr Pro Asp
                165                 170


<210> SEQ ID NO 39
<211> LENGTH: 154
<212> TYPE: PRT
<213> ORGANISM: Cyanothece ATCC51142

<400> SEQUENCE: 39

Met Ala Val Asn Arg Ile Arg Ile Gly Lys Asp Lys Gly Glu Leu Val
1               5                   10                  15

Gln Ser Leu Val Asp Phe Asn Gly Gly Val Gly Pro Phe Gln Thr Tyr
            20                  25                  30

Ala Asp Val Ile Thr Phe Ala Ala Thr Leu Gly Ala Lys Tyr Asn Lys
        35                  40                  45

Arg Ile Pro Leu Asn Ile Ile Ser Lys Glu Pro Ala Pro Ile Ser Leu
    50                  55                  60

Glu Ile Phe Val Ser Arg Gly Tyr Asp Ala Val Ile Lys Leu Leu Ala
65                  70                  75                  80

Ile Thr Glu Thr Asn Asp Pro His Ile Leu Ser Leu Tyr Asp Thr Glu
                85                  90                  95

Ala Glu Asn Gln Arg Ile Gln Ile Phe Glu Glu Tyr Ala Asn Gly Gly
            100                 105                 110

Leu Glu Gln Leu Gln Glu Glu Leu Lys Gly Ile Val Asp Tyr Ser Glu
        115                 120                 125

His Leu Leu Leu Leu Leu Asn Leu Glu Arg Phe Pro Asn Asn Thr Thr
    130                 135                 140

Glu Glu Glu Phe Asp Leu Thr Arg Phe Leu
145                 150


<210> SEQ ID NO 40
<211> LENGTH: 199
<212> TYPE: PRT
<213> ORGANISM: Cyanothece ATCC51142

<400> SEQUENCE: 40

Leu Leu Tyr Leu Ile Ile Ile Leu Arg Lys Ile Met Asn Pro Lys Glu
1               5                   10                  15

Asn Lys Lys Glu Leu Arg Gln Lys Ile Ile Lys Lys Arg Glu Lys Leu
            20                  25                  30

Ser Lys Ile Asp Trp Met Asn Lys Ser Asn Lys Leu Cys Glu Asn Leu
        35                  40                  45

Gln Asn Tyr Pro Leu Leu Gln Lys Ser Lys Thr Ile Leu Ala Tyr Phe
    50                  55                  60

Ser Val Arg Gln Glu Pro Asn Leu Ile Ser Leu Phe Ser Thr Asp Tyr
65                  70                  75                  80

Asn Trp Gly Phe Pro Arg Cys Val Lys Lys Ser Leu Ile Trp His Ser
                85                  90                  95

Trp Arg Arg Glu Asp Pro Leu Ile Pro Gly Lys Tyr Gly Ile Leu Glu
```

```
            100                 105                 110

Pro Ala Ala Asn Ala Pro Ile Leu Thr Pro Glu Lys Val Asp Leu Ile
        115                 120                 125

Leu Val Pro Ala Val Ala Cys Asp Tyr Asn Gly Tyr Arg Leu Gly Tyr
    130                 135                 140

Gly Gly Gly Phe Tyr Asp Arg Phe Leu Asn Ser Pro Gln Trp His Ser
145                 150                 155                 160

Ile Pro Thr Ile Gly Ile Ile Phe Glu Phe Ala Leu Leu Pro Gln Leu
                165                 170                 175

Pro Tyr Glu Pro Trp Asp Gln Lys Leu Gln Ala Ile Cys Thr Glu Asn
            180                 185                 190

Glu Ile Ile Ser Ile Ser Thr
        195


<210> SEQ ID NO 41
<211> LENGTH: 106
<212> TYPE: PRT
<213> ORGANISM: Cyanothece ATCC51142

<400> SEQUENCE: 41

Met Lys His Phe Arg Asp Glu Trp Ile Gln Glu Trp Cys Glu Glu Asn
1               5                   10                  15

Gly Trp Thr Asp Leu Phe Arg Glu Arg Tyr Asn His Tyr Trp Ala Phe
            20                  25                  30

Pro Pro Gly Ala Val Met Pro Glu Pro Ile Pro Ser Glu Val Leu Arg
        35                  40                  45

Phe Ile Lys Ala Thr Lys Gly Phe Cys Ala Glu Glu Arg Thr Trp Leu
    50                  55                  60

Ile Ser Ala Ile Leu Val Ser Ile Ile Ser Val Val Leu Ser Tyr Phe
65                  70                  75                  80

Phe Lys Asn Pro Met Pro Ile Val Phe Ala Phe Ala Phe Ala Ala Val
                85                  90                  95

Thr Ser Ala Lys Leu Glu Val Glu Glu Ile
            100                 105


<210> SEQ ID NO 42
<211> LENGTH: 521
<212> TYPE: PRT
<213> ORGANISM: Cyanothece ATCC51142

<400> SEQUENCE: 42

Val Ser Leu Leu Leu Asn Asn Arg Tyr Gln Val Ile Glu Thr Leu Gly
1               5                   10                  15

Lys Gly Gly Phe Gly Glu Thr Phe Leu Ala Ile Asp Thr His Met Pro
            20                  25                  30

Ser Glu Arg Lys Cys Val Ile Lys Gln Leu Lys Pro Ala Val Gln Ser
        35                  40                  45

Pro Val Ile Pro Asp Trp Leu Lys Glu Arg Phe Ala Lys Glu Ala Ala
    50                  55                  60

Ile Leu Glu Glu Leu Gly Glu Lys His Pro Gln Ile Pro Thr Leu Tyr
65                  70                  75                  80

Ala Tyr Phe Ser Glu Gly Gly Asp Phe Tyr Leu Val Gln Glu Trp Ile
                85                  90                  95

Glu Gly Glu Thr Leu Thr Gln Ile His Gln Arg Gln Gly Asn Leu Ser
            100                 105                 110

Pro Asn Gln Val Arg Glu Ile Leu Ile Gly Ile Leu Pro Val Leu Asp
```

```
        115                 120                 125

Tyr Ile His Ser Arg Arg Ile Ile His Arg Asp Ile Lys Pro Asp Asn
    130                 135                 140

Ile Ile Ile Arg Ser His Asp Lys Lys Pro Val Leu Ile Asp Phe Gly
145                 150                 155                 160

Ile Val Lys Glu Thr Val Ala Thr Met Ile His Gly Asp Gly Asn Thr
                165                 170                 175

Pro Tyr Ser Val Gly Leu Gly Thr Pro Gly Tyr Met Ala Ser Glu Gln
            180                 185                 190

Ala Ala Gly Arg Pro Leu Asn Ser Ser Asp Leu Tyr Ser Leu Gly Leu
        195                 200                 205

Thr Met Val Phe Leu Leu Thr Gly Lys Thr Pro Gln Tyr Leu Ala Thr
    210                 215                 220

Asp Pro Asn Thr Gly Glu Val Leu Trp Arg Lys Glu Ala Pro Asp Ile
225                 230                 235                 240

Gln Ser Asn Val Gly Asn Val Ile Asp Arg Ala Val Arg Phe His Pro
                245                 250                 255

Arg Asp Arg Phe Ser Thr Ala Lys Glu Met Leu Glu Ala Leu Gln Val
            260                 265                 270

Pro His Thr Ile Pro Thr Ala Ala Thr Ile Ala Ile Gly Gln Gln Asn
        275                 280                 285

Leu Ser Leu Ser Arg Ser Ser Thr His Thr Pro Ile Pro Thr Asn Leu
    290                 295                 300

Pro Ala Glu Ala Thr Glu Thr Glu Thr Asp Thr Pro Trp Ala Leu Leu
305                 310                 315                 320

Ala Leu Gly Ser Phe Leu Ala Ala Ser Ala Ile Ile Gly Gly Leu Met
                325                 330                 335

Leu Gly Ile Met Leu Gly Thr Lys Glu Arg Ser Gln Pro Thr Ser Ser
            340                 345                 350

Pro Ser Val Ser Pro Glu Ser Pro Glu Val Pro Glu Asn Ser Gln Pro
        355                 360                 365

Glu Phe Ser Gln Pro Arg Pro Thr Leu Arg Arg Pro Val Arg Arg Ser
    370                 375                 380

Pro Gly Ser Gln Ser Ser Pro Thr Leu Glu Ala Thr Pro Thr Pro Thr
385                 390                 395                 400

Leu Glu Pro Ser Pro Thr Leu Glu Ala Thr Pro Thr Pro Thr Leu Glu
                405                 410                 415

Pro Ser Pro Asn Ser Thr Val Gln Pro Ser Pro Thr Pro Lys Ala Ser
            420                 425                 430

Pro Ser Pro Thr Ser Thr Pro Ile Pro Glu Pro Thr Lys Val Val Pro
        435                 440                 445

Ile Pro Val Glu Pro Pro Pro Gln Val Ser Glu Pro Lys Glu Pro Thr
    450                 455                 460

Asn Gln Glu Gly Ser Glu Pro Ser Leu Val Ile Pro His Ile Pro Pro
465                 470                 475                 480

Lys Pro Ala Glu Glu Lys Pro Pro Lys Glu Glu Glu Asn Lys Gln Asn
                485                 490                 495

Ile Gln Lys Tyr Phe Glu Ser Asp Arg Glu Gln Asn Lys Ser Asn Leu
            500                 505                 510

Gln Gln Tyr Phe Asp Ser Asp Arg Pro
        515                 520
```

<210> SEQ ID NO 43

<211> LENGTH: 60
<212> TYPE: PRT
<213> ORGANISM: Cyanothece ATCC51142

<400> SEQUENCE: 43

Val Tyr Ile Tyr Leu Arg Lys Asn Met Asp Val Val Arg Ile Ile Cys
1 5 10 15

Ala Ile Ile Leu Pro Pro Leu Gly Val Phe Leu Gln Val Gly Ile Gly
20 25 30

Pro Gln Phe Trp Ile Asn Ile Leu Leu Thr Leu Leu Gly Tyr Ile Pro
35 40 45

Gly Ile Val His Ala Val Trp Val Ile Ala Lys Lys
50 55 60

<210> SEQ ID NO 44
<211> LENGTH: 114
<212> TYPE: PRT
<213> ORGANISM: Cyanothece ATCC51142

<400> SEQUENCE: 44

Leu Ile Met Ser Tyr Ser Leu Ser Pro Gln Glu Lys Ser Asn Thr Thr
1 5 10 15

Leu Phe Ser Leu Cys Asn Gln Arg Lys His Gln Arg Tyr Tyr Asn Ser
20 25 30

Gln Gly Ser Ser Val Glu Leu Leu Ile Asp Gly Gln Glu Ile Lys Gln
35 40 45

Ser Leu Lys Gly Met Ile Ile Asp Asp Ser Phe Ser Gly Cys Gly Leu
50 55 60

Ile Ile Ile Gly Glu Glu Lys Leu His Ile Gly Gln Leu Cys Arg Leu
65 70 75 80

Arg Ile Lys Gly Ile Asp Ser Ile Leu Cys Gln Ile Ile Trp Leu Arg
85 90 95

Arg Leu Glu Lys Ser Ile Thr Arg Ile Gly Val Lys Tyr Leu Ile Lys
100 105 110

Ser Glu

<210> SEQ ID NO 45
<211> LENGTH: 233
<212> TYPE: PRT
<213> ORGANISM: Cyanothece ATCC51142

<400> SEQUENCE: 45

Met Val Pro Leu Asn Asp Asn Asn Pro Thr Gln Arg Thr Ala Tyr Val
1 5 10 15

Thr Tyr Gly Leu Ile Ile Leu Asn Val Leu Val Phe Phe Lys Glu Leu
20 25 30

Ser Leu Ser Ser Glu Glu Leu Ser Gln Phe Phe Gln Tyr Tyr Ala Ile
35 40 45

Val Pro Lys Gln Leu Thr Ala Gly Phe Ser Gly Val Asp Phe Tyr His
50 55 60

Pro Ile Pro Glu Trp Met Thr Leu Phe Thr Ser Gln Phe Leu His Ala
65 70 75 80

Gly Phe Leu His Ile Ala Gly Asn Met Leu Phe Leu Trp Ile Phe Gly
85 90 95

Asn Asn Val Glu Asp Lys Leu Gly His Val Lys Tyr Leu Ile Phe Tyr
100 105 110

Leu Thr Cys Gly Val Leu Ala Gly Leu Ser Gln Trp Tyr Phe Ala Pro

```
        115                 120                 125

Tyr Ser Glu Val Pro Ser Leu Gly Ala Ser Gly Ala Ile Ala Gly Val
    130                 135                 140

Met Gly Ala Tyr Ile Leu Arg Phe Pro Gln Ala Gln Val Leu Thr Leu
145                 150                 155                 160

Ile Pro Leu Gly Ile Phe Ile Thr Thr Ile Arg Ile Pro Ala Val Phe
                165                 170                 175

Phe Leu Gly Phe Trp Phe Leu Gln Gln Ala Ile Tyr Gly Phe Ala Ser
            180                 185                 190

Leu Asn Val Gln Thr Asn Val Gly Met Glu Gly Gly Gly Val Ala Tyr
        195                 200                 205

Trp Ala His Ala Gly Gly Phe Val Phe Gly Phe Ile Leu Gly Pro Leu
    210                 215                 220

Leu Gly Leu Leu Asp Asp Lys Asn Arg
225                 230


<210> SEQ ID NO 46
<211> LENGTH: 161
<212> TYPE: PRT
<213> ORGANISM: Cyanothece ATCC51142

<400> SEQUENCE: 46

Met Val Lys Arg Phe Ile Leu Met Ala Ile Ala Ala Ile Phe Phe Phe
1               5                   10                  15

Leu Gln Phe Pro Ile His Asn Ala Asn Ala Leu Glu Leu Thr Glu Glu
            20                  25                  30

Thr Arg Thr Val Pro Leu Asn Glu Glu Gly Glu Thr Ile Thr Leu Thr
        35                  40                  45

Ser Glu Gln Ile Thr Asn Gly Gln Arg Leu Phe Ile Arg Glu Cys Thr
    50                  55                  60

Gln Cys His Leu Gln Gly Lys Thr Lys Thr Asn Asn Asn Val Ser Leu
65                  70                  75                  80

Gly Leu Glu Asp Leu Ser Leu Ala Glu Pro Pro Arg Asp Asn Val Leu
                85                  90                  95

Gly Leu Val Asp Tyr Leu Lys Tyr Pro Thr Ser Tyr Asp Gly Glu Asp
            100                 105                 110

Asp Tyr Thr Glu Leu His Val Asn Val Ser Arg Pro Asp Ile Tyr Pro
        115                 120                 125

Glu Leu Arg Asp Phe Thr Glu Asp Asp Leu Tyr Asp Val Ser Gly Tyr
    130                 135                 140

Ile Leu Val Ala Pro Lys Leu Asp Ser Tyr Trp Gly Gly Ser Ile Tyr
145                 150                 155                 160

Phe


<210> SEQ ID NO 47
<211> LENGTH: 31
<212> TYPE: PRT
<213> ORGANISM: Cyanothece ATCC51142

<400> SEQUENCE: 47

Leu Leu Arg Gly Glu Asn Arg Phe Leu Ser Leu Lys Lys Ser Pro Ile
1               5                   10                  15

Pro Pro Arg Glu Gly Lys Phe Lys Asp Gln Glu Leu Trp Tyr Arg
            20                  25                  30


<210> SEQ ID NO 48
```

```
<211> LENGTH: 237
<212> TYPE: PRT
<213> ORGANISM: Cyanothece ATCC51142

<400> SEQUENCE: 48

Met Ser Ala Thr Cys Val Ile Asn Gly Trp Glu Arg Pro Glu Lys Thr
1               5                   10                  15

Pro Met Leu Lys Leu Tyr His Leu Pro Ile Ser Phe Asn Ser Arg Arg
            20                  25                  30

Val Trp Ile Ala Leu Leu Glu Lys Gly Leu Ser Phe Glu Leu Ile Pro
        35                  40                  45

Met Lys Leu Asn Gly Asp Gln Leu Thr Pro Glu Phe Leu Ala Leu Asn
    50                  55                  60

Pro Phe His His Ile Pro Val Leu Val Asp Glu Ala Phe Ser Leu Phe
65                  70                  75                  80

Glu Ser Leu Ala Ile Leu Asp Tyr Leu Glu Ala Lys Tyr Pro Thr Pro
                85                  90                  95

Ser Leu Val Pro Ser Asp Pro Gln Gly Leu Gly Thr Val Lys Met Ile
            100                 105                 110

Asn Leu Val Thr Leu Asn Glu Leu Leu Pro Ala Thr Thr Pro Leu Ile
        115                 120                 125

Gln His Ser Met Gly Phe Ile Thr Leu Asp Glu Gln Arg Ile Ala Asn
    130                 135                 140

Thr Lys Glu Lys Val Ala Val Val Leu Asn Phe Phe Glu Thr Ser Leu
145                 150                 155                 160

Gly Asp Arg Ser Tyr Ile Val Gly Asn Thr Leu Thr Leu Ala Asp Ile
                165                 170                 175

Val Ala Gly Thr Met Val Gly Phe Leu Pro Gln Met Gly Val Ser Leu
            180                 185                 190

Ser Ala Tyr Pro Gln Leu Thr Ala Trp Thr Lys Gln Leu Ser Gln Arg
        195                 200                 205

Glu Ser Trp Gln Gln Thr Glu Pro Gln Pro Glu Glu Ile Asp Lys Phe
    210                 215                 220

Arg Glu Thr Met Lys Lys Leu Met Ala Gln Arg Gly Ser
225                 230                 235


<210> SEQ ID NO 49
<211> LENGTH: 180
<212> TYPE: PRT
<213> ORGANISM: Cyanothece ATCC51142

<400> SEQUENCE: 49

Met Thr Gln Val Ser Gly Ser Ser Asp Val Pro Asp Met Gly Arg Arg
1               5                   10                  15

Gln Phe Met Asn Leu Leu Thr Phe Gly Thr Ile Thr Gly Val Ala Ala
            20                  25                  30

Gly Ala Leu Tyr Pro Val Val Lys Tyr Phe Ile Pro Pro Ser Ser Gly
        35                  40                  45

Gly Ala Gly Gly Gly Ile Thr Ala Lys Asp Ala Leu Gly Asn Asp Ile
    50                  55                  60

Met Ala Ser Asn Phe Leu Ala Thr His Asn Gly Gly Asp Arg Val Leu
65                  70                  75                  80

Ala Gln Gly Leu Lys Gly Asp Pro Thr Tyr Leu Val Val Glu Gly Glu
                85                  90                  95

Asn Ala Ile Ala Asp Tyr Gly Ile Asn Ala Val Cys Thr His Leu Gly
            100                 105                 110
```

```
Cys Val Val Pro Trp Asn Ala Ser Glu Asp Lys Phe Ile Cys Pro Cys
        115                 120                 125

His Gly Ser Gln Tyr Asn Ala Gln Gly Lys Val Val Arg Gly Pro Ala
    130                 135                 140

Pro Leu Ser Leu Ala Leu Ala His Val Asn Val Ser Glu Asp Asp Lys
145                 150                 155                 160

Val Val Phe Ser Glu Trp Thr Glu Thr Asp Phe Arg Thr Glu Gln Asp
                165                 170                 175

Pro Trp Trp Ala
            180


<210> SEQ ID NO 50
<211> LENGTH: 303
<212> TYPE: PRT
<213> ORGANISM: Cyanothece ATCC51142

<400> SEQUENCE: 50

Leu Ile Val Ala Ala Thr Val Ala Leu Phe Ile Gly Asn Val Gln Ser
1               5                   10                  15

Ala Asn Ala Tyr Pro Phe Trp Ala Gln Glu Thr Ala Pro Glu Thr Pro
            20                  25                  30

Arg Glu Ala Thr Gly Arg Ile Val Cys Ala Asn Cys His Leu Ala Glu
        35                  40                  45

Lys Ala Ala Glu Val Glu Ile Pro Gln Ser Val Leu Pro Asp Thr Val
    50                  55                  60

Phe Lys Ala Val Val Lys Ile Pro Tyr Asp Leu Asp Ser Gln Gln Val
65                  70                  75                  80

Leu Gly Asp Gly Ser Lys Gly Gly Leu Asn Val Gly Ala Val Leu Met
                85                  90                  95

Leu Pro Glu Gly Phe Lys Ile Ala Pro Asp Glu Arg Ile Pro Glu Glu
            100                 105                 110

Ile Lys Glu Glu Met Gly Ser Val Tyr Phe Gln Ser Tyr Ser Glu Gly
        115                 120                 125

Gln Asp Asn Val Val Leu Val Gly Pro Leu Pro Gly Glu Gln Tyr Gln
    130                 135                 140

Glu Ile Ile Phe Pro Ile Leu Ser Pro Asp Pro Ser Lys Asp Lys Asn
145                 150                 155                 160

Val Asn Phe Gly Lys Tyr Gln Val His Leu Gly Ala Asn Arg Gly Arg
                165                 170                 175

Gly Gln Ile Tyr Pro Thr Gly Gln Pro Ser Asn Asn Asn Val Phe Lys
            180                 185                 190

Ala Ser Asn Ala Gly Thr Ile Ser Lys Ile Thr Asp Gln Glu Asp Gly
        195                 200                 205

Ser Tyr Ile Val Thr Ile Ala Thr Ala Glu Gly Asp Val Asp Glu Thr
    210                 215                 220

Ile Pro Ala Gly Pro Gln Leu Met Val Ser Glu Gly Met Glu Val Glu
225                 230                 235                 240

Ala Gly Gln Ala Leu Thr Asn Asn Pro Asn Val Gly Gly Phe Gly Gln
                245                 250                 255

Lys Asp Thr Glu Val Val Leu Gln Ser Pro Gly Arg Ile Lys Gly Leu
            260                 265                 270

Ile Leu Phe Leu Ala Gly Ile Met Leu Ala Gln Ile Leu Leu Val Ile
        275                 280                 285

Lys Lys Lys Gln Val Glu Arg Val Gln Ala Ala Glu Met Asn Phe
```

290 295 300

<210> SEQ ID NO 51
<211> LENGTH: 32
<212> TYPE: PRT
<213> ORGANISM: Cyanothece ATCC51142

<400> SEQUENCE: 51

Val Ile Met Ile Leu Ile Val Val Val Ala Leu Ile Tyr Glu Ile Phe
1 5 10 15

Ser Glu Val Val Ile Asn Ala Pro Phe Asp Tyr Asn Pro Arg Asp Glu
20 25 30

<210> SEQ ID NO 52
<211> LENGTH: 310
<212> TYPE: PRT
<213> ORGANISM: Cyanothece ATCC51142

<400> SEQUENCE: 52

Leu Thr Thr Ile Leu Gly Met Asn Ser Ile Thr Gly Cys Ser Ser Ser
1 5 10 15

Asn Pro Val Asp Ser Gly Ile Asn Lys Ser Asp Asn Gln Glu Gln Ser
20 25 30

Asn Ser Gln Asp Gln Leu Asp Ile Thr Val Ser Ile Ile Pro Gln Lys
35 40 45

Tyr Phe Val Lys Lys Ile Gly Gly Asp Leu Val Arg Val Asn Val Met
50 55 60

Val Glu Gln Gly Val Leu Pro His Thr Tyr Glu Pro Lys Pro Gln Gln
65 70 75 80

Leu Gln Ala Leu Ser Glu Ala Glu Ala Tyr Ile Gly Ile Gly Ile Pro
85 90 95

Phe Glu Thr Ala Trp Met Asp Arg Ile Lys Glu Ala Asn Pro Lys Met
100 105 110

Leu Met Val Asp Ser Thr Gln Gly Ile Asp Arg Leu Thr Met Ile Ala
115 120 125

His Asp His His Glu Glu Glu Asp His Gly His His Glu Glu Glu Thr
130 135 140

Thr Leu Asp Pro His Val Trp Leu Ser Pro Arg Leu Val Lys Ile Gln
145 150 155 160

Ala Gln Lys Ile Tyr Glu Thr Leu Val Lys Leu Asp Pro Lys His Gln
165 170 175

Glu Thr Tyr Gln Thr Asn Leu Asn Ser Phe Leu Gln Glu Ile Glu Glu
180 185 190

Leu Asp His Gln Val Arg Asn Asn Leu Ala Asn Leu Lys Gln Arg Lys
195 200 205

Phe Ile Val Phe His Pro Ala Trp Gly Tyr Phe Ala Glu Glu Tyr Asn
210 215 220

Leu Thr Gln Val Pro Ile Glu Val Gly Gly Gln Glu Pro Ser Ala Ser
225 230 235 240

Glu Leu Gly Asp Leu Ile Lys Glu Ala Lys Lys Glu Asn Ile Lys Val
245 250 255

Ile Phe Ala Gln Pro Glu Leu Ser Ser Gln Ala Ala Lys Thr Ile Ala
260 265 270

Lys Glu Ile Asn Gly Glu Val Leu Leu Ile Ser Pro Thr Ala Ala Asp
275 280 285

Trp Ser Asn Asn Leu Leu Glu Val Ser Gln Thr Phe Ala Lys Val Leu

```
    290                 295                 300

Lys Glu Glu Asn Asn Gln
305                 310


<210> SEQ ID NO 53
<211> LENGTH: 259
<212> TYPE: PRT
<213> ORGANISM: Cyanothece ATCC51142

<400> SEQUENCE: 53

Met Lys Thr Glu Val Ile Asn Leu Ser His Val Trp Ala Lys Tyr Asn
1               5                   10                  15

His Arg Asn Pro Ile Leu Glu Asp Ile Asn Leu Thr Ile Tyr Glu Gly
            20                  25                  30

Asp Phe Val Gly Leu Ile Gly Pro Asn Gly Gly Gly Lys Thr Thr Leu
        35                  40                  45

Phe Lys Val Leu Leu Gly Leu Ile Lys Pro Tyr Gln Gly Thr Val Lys
    50                  55                  60

Ile Leu Gly Asn Thr Val Ser Lys Gly Arg Arg Tyr Ile Gly Tyr Val
65                  70                  75                  80

Pro Gln Leu Val Glu Leu Asp Arg Glu Phe Pro Val Arg Val Ala Asp
                85                  90                  95

Val Val Arg Met Gly Arg Leu Gly Lys Arg Arg Leu Leu Gln Arg Tyr
            100                 105                 110

Thr Pro Gln Asp Glu Ile Ile Val Asn Arg Thr Leu Glu Gln Val Gly
        115                 120                 125

Met Ile Glu Leu Arg Asn Arg Pro Ile Ala Glu Leu Ser Gly Gly Gln
    130                 135                 140

Arg Gln Arg Val Tyr Ile Ala Arg Ala Leu Ala Ser Glu Pro Arg Ile
145                 150                 155                 160

Leu Leu Leu Asp Glu Pro Thr Ala Ser Val Asp Pro Gln Arg Gln Thr
                165                 170                 175

Ser Ile Tyr Glu Leu Leu Lys Glu Leu Asn Gln Leu Ile Thr Ile Val
            180                 185                 190

Met Ile Ser His Asp Ile Gly Ala Ile Ser Ala Tyr Val Lys Thr Val
        195                 200                 205

Gly Cys Leu Asn His Arg Leu Phe Phe His Gly Asp Pro Pro Leu Ser
    210                 215                 220

Thr Glu Thr Ile Glu Gln Thr Tyr Gln Cys Pro Val Asp Leu Ile Ala
225                 230                 235                 240

His Gly Val Pro His Arg Val Leu Ser Asn His Asp Cys Pro Leu His
                245                 250                 255

Tyr His Glu


<210> SEQ ID NO 54
<211> LENGTH: 271
<212> TYPE: PRT
<213> ORGANISM: Cyanothece ATCC51142

<400> SEQUENCE: 54

Met Leu Glu Thr Leu Trp Glu Ser Leu Gln Phe Asp Phe Met Arg Asn
1               5                   10                  15

Ala Leu Phe Ala Gly Ile Leu Val Ser Ile Ala Cys Gly Ile Ile Gly
            20                  25                  30

Thr Phe Val Val Ile Asn Arg Ile Val Phe Ile Ser Gly Gly Ile Ala
        35                  40                  45
```

```
His Ala Ala Tyr Gly Gly Ile Gly Leu Gly Tyr Phe Phe Lys Ile Asn
    50                  55                  60

Pro Ile Phe Gly Ala Ile Phe Phe Ala Leu Leu Ser Ala Leu Gly Met
65                  70                  75                  80

Gly Leu Val Val Arg Lys Thr Glu Gln Arg Ala Asp Ser Leu Ile Gly
                85                  90                  95

Val Met Trp Ala Val Gly Met Ala Ile Gly Ile Ile Leu Ile Asp Leu
            100                 105                 110

Thr Pro Gly Tyr Lys Ala Asp Leu Met Ser Tyr Leu Phe Gly Ser Ile
        115                 120                 125

Leu Thr Val Ser Gln Glu Asn Leu Met Ile Met Leu Val Leu Asp Val
    130                 135                 140

Ile Ile Val Leu Val Val Ser Leu Phe Tyr Lys Glu Phe Leu Ala Ile
145                 150                 155                 160

Ser Phe Asp Pro Thr Phe Ala Met Thr Arg Asn Val Pro Val Asp Ser
                165                 170                 175

Leu Tyr Leu Leu Leu Val Gly Ala Ile Ala Leu Thr Val Val Met Val
            180                 185                 190

Met Gln Val Val Gly Leu Ile Leu Val Ile Ala Leu Leu Thr Ile Pro
        195                 200                 205

Ala Ala Ile Ala Gly Gln Phe Leu Lys Asp Ile Lys Tyr Ile Met Leu
    210                 215                 220

Val Ser Ile Val Leu Gly Met Leu Phe Thr Thr Val Gly Leu Met Ile
225                 230                 235                 240

Ser Tyr Phe Phe Asn Val Thr Ser Gly Ala Thr Ile Ile Leu Val Ser
                245                 250                 255

Gly Thr Ala Tyr Leu Ile Ser Leu Gly Val Lys Thr Leu Gln Ile
            260                 265                 270


<210> SEQ ID NO 55
<211> LENGTH: 42
<212> TYPE: PRT
<213> ORGANISM: Cyanothece ATCC51142

<400> SEQUENCE: 55

Leu Cys Tyr Ser Ser Pro Glu Gly Ile Lys Gln Gly Arg Gln Glu Gly
1               5                   10                  15

Lys Leu Ala Ala Lys Ile Ala Ser Ile Pro Arg Leu Val Thr Leu Glu
            20                  25                  30

Leu Ser Val Glu Gln Ile Ala Gln Ala Leu
        35                  40


<210> SEQ ID NO 56
<211> LENGTH: 88
<212> TYPE: PRT
<213> ORGANISM: Cyanothece ATCC51142

<400> SEQUENCE: 56

Leu Pro Leu Ile Ser Arg Gln Glu Ile Glu Lys Met Phe Ser Leu Ser
1               5                   10                  15

Asp Leu Arg Glu Thr Lys Val Tyr Gln Glu Ala Leu Glu Glu Gly Ile
            20                  25                  30

Glu Lys Gly Ile Glu Gln Gly Ile Glu Gln Gly Arg Gln Glu Gly Glu
        35                  40                  45

Leu Ala Ala Lys Ile Ala Ser Ile Pro Arg Leu Val Ala Leu Gly Leu
    50                  55                  60
```

Thr Ile Glu Gln Ile Ala Gln Ala Leu Glu Leu Asp Ile Glu Gln Val
65 70 75 80

Ser Asn Ile Val Glu Ser Asn Lys
85

<210> SEQ ID NO 57
<211> LENGTH: 354
<212> TYPE: PRT
<213> ORGANISM: Cyanothece ATCC51142

<400> SEQUENCE: 57

Met Thr Gly Ala Asn Asp Thr Pro Tyr Leu Leu Arg Ala Ala Arg Gly
1 5 10 15

Glu Ile Leu Asp Arg Pro Pro Val Trp Met Met Arg Gln Ala Gly Arg
20 25 30

Tyr Met Lys Val Tyr Arg Asp Leu Arg Asp Lys Tyr Pro Ser Phe Arg
35 40 45

Glu Arg Ser Glu Asn Pro Asp Leu Ala Ile Glu Ile Ser Leu Gln Pro
50 55 60

Trp Arg Ala Phe Gln Pro Asp Gly Val Ile Met Phe Ser Asp Ile Leu
65 70 75 80

Thr Pro Leu Pro Gly Met Gly Ile Pro Phe Asp Ile Val Glu Ser Lys
85 90 95

Gly Pro Val Ile Asp Pro Pro Ile Arg Thr Lys Glu Gln Val Asp Asn
100 105 110

Leu Arg Pro Leu Asp Pro Glu Glu Ser Leu Pro Phe Ile Lys Thr Ile
115 120 125

Leu Gln Ser Leu Arg Gln Glu Val Gly Asn Gln Ser Thr Val Leu Gly
130 135 140

Phe Val Gly Ser Pro Trp Thr Leu Ala Ala Tyr Ala Ile Glu Gly Lys
145 150 155 160

Ser Ser Lys Asn Tyr Ala Ile Ile Lys Ser Met Ala Phe Ser Gln Pro
165 170 175

Glu Ile Leu His Ser Phe Leu Ser Lys Ile Ala Asp Ala Ile Ala Ile
180 185 190

Tyr Val Arg Tyr Gln Ile Asp Cys Gly Ala Gln Val Val Gln Leu Phe
195 200 205

Asp Ser Trp Ala Gly Gln Leu Ser Pro Gln Asp Tyr Glu Thr Phe Ala
210 215 220

Leu Pro Tyr Gln Gln Gln Val Val Arg Gln Val Lys Glu Thr His Pro
225 230 235 240

Asp Thr Pro Leu Ile Leu Tyr Ile Ser Gly Ser Ala Gly Val Leu Glu
245 250 255

Arg Met Gly Gln Ser Gly Val Asp Ile Val Ser Val Asp Trp Thr Val
260 265 270

Asp Met Ala Glu Ala Arg Gln Arg Leu Gly Arg Asp Met Lys Val Gln
275 280 285

Gly Asn Ile Asp Pro Gly Val Leu Phe Gly Ser Gln Asp Phe Ile Lys
290 295 300

Ala Arg Ile Leu Asp Thr Val Arg Lys Ala Gly Arg Gly Gly His Ile
305 310 315 320

Leu Asn Leu Gly His Gly Val Leu Val Gly Thr Pro Glu Asp Asn Val
325 330 335

Arg Cys Phe Phe Glu Thr Ala Lys Gln Val Asp Gln Leu Leu Ala Val

```
            340                 345                 350

Pro Val


<210> SEQ ID NO 58
<211> LENGTH: 368
<212> TYPE: PRT
<213> ORGANISM: Cyanothece ATCC51142

<400> SEQUENCE: 58

Leu Ile Gln Lys Asn Pro Phe Lys Gln Ala Met Val Asn Thr Leu Gln
1               5                   10                  15

Lys Pro Glu Phe Glu Glu Leu Arg Pro Gly Ile Lys Val Pro Ala Lys
            20                  25                  30

Glu Thr Ile Leu Thr Pro Arg Phe Tyr Thr Thr Asp Phe Glu Ala Met
        35                  40                  45

Ala Lys Met Asp Ile Ser Val Asn Glu Glu Glu Leu Gln Ala Ile Leu
    50                  55                  60

Glu Glu Phe Arg Thr Asp Tyr Asn Arg His His Phe Ile Arg Arg Glu
65                  70                  75                  80

Glu Phe Ala Gln Thr Trp Asp His Ile Asp Gly Asp Thr Arg Arg Leu
                85                  90                  95

Phe Val Glu Phe Leu Glu Arg Ser Cys Thr Ala Glu Phe Ser Gly Phe
            100                 105                 110

Leu Leu Tyr Lys Glu Leu Gly Arg Arg Leu Lys Asp Lys Ser Pro Val
        115                 120                 125

Leu Ala Glu Cys Phe Thr Leu Met Ser Arg Asp Glu Ala Arg His Ala
    130                 135                 140

Gly Phe Leu Asn Lys Ala Leu Ser Asp Phe Asn Met Ser Leu Asp Leu
145                 150                 155                 160

Gly Phe Leu Thr Lys Ser Arg Ser Tyr Thr Phe Phe Gln Pro Lys Phe
                165                 170                 175

Ile Phe Tyr Ala Thr Tyr Leu Ser Glu Lys Ile Gly Tyr Trp Arg Tyr
            180                 185                 190

Ile Thr Ile Tyr Arg His Leu Glu Gln His Pro Glu Asp Arg Ile Tyr
        195                 200                 205

Pro Ile Phe Asn Phe Phe Glu Asn Trp Cys Gln Asp Glu Asn Arg His
    210                 215                 220

Gly Asp Phe Phe Asp Ala Ile Met Lys Ala Thr Pro Asp Ile Leu Asn
225                 230                 235                 240

Asp Trp Lys Ala Arg Leu Trp Cys Arg Phe Phe Leu Leu Ser Val Phe
                245                 250                 255

Ala Thr Met Tyr Leu Asn Asp Ile Gln Arg Ser Asp Phe Tyr Ala Ser
            260                 265                 270

Ile Gly Leu Asp Ala Arg Asp Tyr Asp Lys Tyr Val Ile Glu Lys Thr
        275                 280                 285

Asn Glu Thr Ala Gly Arg Val Phe Pro Ile Val Leu Asp Val Asp Asn
    290                 295                 300

Pro Glu Phe Tyr Asp Ser Leu Glu Val Cys Val Lys Asn Asn Glu Lys
305                 310                 315                 320

Leu Arg Glu Ile Asp Ala Ser Asn Ser Pro Thr Pro Val Lys Phe Leu
                325                 330                 335

Arg Lys Leu Pro Ala Phe Ile Ser Asn Gly Val Gln Phe Leu Lys Leu
            340                 345                 350

Tyr Phe Met Lys Pro Ile Arg Val Asp His Leu Glu Gly Thr Val Arg
```

355 360 365

<210> SEQ ID NO 59
<211> LENGTH: 147
<212> TYPE: PRT
<213> ORGANISM: Cyanothece ATCC51142

<400> SEQUENCE: 59

Met Ile Lys Leu Ser Asn Ser Lys Cys Leu Ser Ser Thr Leu Ser Leu
1 5 10 15

Phe Thr Ile Leu Ile Asn Leu Leu Leu Ile Ser Cys Ala Glu Thr Lys
20 25 30

Val Ser Gln Cys Gln Lys Ile Ile Leu Leu Thr Gln Lys Met Ala Glu
35 40 45

Glu Ser Glu Ser Tyr Arg Gln Thr Thr Asp Ile Lys Lys Val Leu Gln
50 55 60

Val Ala Asp Leu Phe Glu Glu Thr Ser Gln Gln Met Lys Gln Leu Lys
65 70 75 80

Ile Glu Asp Glu Gln Leu Gln Glu Tyr Gln Met Gly Phe Ala Asp Ile
85 90 95

Tyr Gln Gly Asn Ala Asp Thr Thr Arg Gln Phe Val Ala Ala Leu Lys
100 105 110

Asp Lys Asp Ile Asp Thr Ala Lys Leu Met Gln Gln Gln Val Gln Gln
115 120 125

Leu Gly Lys Lys Glu Gln Asp Leu Gly Thr Glu Met Asn Ala Tyr Cys
130 135 140

Gln Pro Asp
145

<210> SEQ ID NO 60
<211> LENGTH: 94
<212> TYPE: PRT
<213> ORGANISM: Cyanothece ATCC51142

<400> SEQUENCE: 60

Met Val Gln Asn Thr Gln Lys Ile Glu Thr Ile Leu Glu Arg Met Gly
1 5 10 15

Glu Thr Val Ile Ala Thr Thr Glu Thr Val Glu Ser Leu Ala Glu Lys
20 25 30

Met Glu Asn Leu Val Glu Gln Ile Gln Gln Gln Glu Gln Gln Ile Gln
35 40 45

Gln Gln Gly Tyr Gln Ile Phe Ala Leu Ser Glu Ser Ile Gln Thr Leu
50 55 60

Val Asp Ala Gln Thr Glu Ser Arg Glu Gln Leu Thr Gln Leu Thr Tyr
65 70 75 80

Leu Ile His Thr Leu Val His Ser Leu Thr Asn Gln Glu Glu
85 90

<210> SEQ ID NO 61
<211> LENGTH: 336
<212> TYPE: PRT
<213> ORGANISM: Cyanothece ATCC51142

<400> SEQUENCE: 61

Val Leu Val Ser Asp Thr Lys Pro Thr Ile Leu Val Thr Gly Gly Ala
1 5 10 15

Gly Tyr Ile Gly Ser His Ala Val Leu Ser Leu Gln Lys Ala Gly Tyr
20 25 30

His Val Ile Val Phe Asp Asn Leu Ser Tyr Gly His Pro Glu Ile Ile
35 40 45

Lys Asp Val Leu Gln Val Glu Leu Ile Val Gly Asp Thr Gln Asn Arg
50 55 60

Thr Leu Leu Asp Glu Leu Phe Ser Thr Arg Asn Ile Ala Ala Val Met
65 70 75 80

His Phe Ala Ala Phe Ile Ala Val Gly Glu Ser Val Gln Ala Pro Ala
85 90 95

Ile Tyr Tyr Gln Asn Asn Val Val Gly Thr Leu Thr Leu Leu Glu Ala
100 105 110

Met Met Ala Ala Asn Ile Asn Lys Phe Val Phe Ser Ser Thr Cys Ala
115 120 125

Ile Tyr Gly Met Pro Gln Glu Ile Pro Met Thr Glu Gln His Pro Asn
130 135 140

His Pro Leu Ser Pro Tyr Ala Ser Ser Lys Tyr Met Val Glu Lys Ile
145 150 155 160

Leu Lys Asp Phe Asp Gln Ala Tyr Gly Leu Lys Ser Val Ile Phe Arg
165 170 175

Tyr Phe Asn Ala Ser Gly Ala Asp Pro Ser Gly Asn Leu Gly Glu Asp
180 185 190

His Thr Pro Glu Thr His Leu Ile Pro Leu Ala Leu Leu Thr Ala Leu
195 200 205

Lys Lys Arg Asp His Leu Phe Ile Phe Gly Thr Asp Tyr Asp Thr His
210 215 220

Asp Gly Thr Ala Ile Arg Asp Tyr Ile His Val Asn Asp Leu Ala Ser
225 230 235 240

Ala His Ile Leu Gly Leu Glu Tyr Leu Leu Asn Gly Gly Glu Ser Glu
245 250 255

Met Phe Asn Leu Gly Asn Gly Asn Gly Phe Ser Val Lys Glu Val Ile
260 265 270

Asp Met Ala Lys Lys Val Thr Gly Ile Asp Phe Leu Val Lys Glu Ser
275 280 285

Asp Arg Arg Pro Gly Asp Val Pro Ile Leu Val Gly Ser Ser Gln Lys
290 295 300

Ala Gln Ser Val Leu Gly Trp Gln Pro Gln Tyr Ser Asp Leu Gln Thr
305 310 315 320

Ile Val Asn His Ala Trp Gln Trp His Gln Lys Arg His Gly Asn Ala
325 330 335

<210> SEQ ID NO 62
<211> LENGTH: 519
<212> TYPE: PRT
<213> ORGANISM: Cyanothece ATCC51142

<400> SEQUENCE: 62

Leu Val Tyr Ser Leu Tyr Thr Glu Lys Ser Ile His Val Phe Tyr Asn
1 5 10 15

Thr Tyr Tyr Tyr Leu Thr Met Leu Asp Thr Leu Asp Leu Lys Leu Thr
20 25 30

Leu Asp Lys Glu Thr Tyr Lys Thr Glu Ile Glu Ala Leu Met Arg Gln
35 40 45

Leu Arg Ser Leu Gln Lys Asp Cys Trp Asp Asn Gln Leu Pro Val Ile
50 55 60

Ile Val Leu Glu Gly Trp Ala Ala Ala Gly Lys Gly Lys Leu Leu Gln

```
65                  70                  75                  80

Lys Thr Ile Gly Tyr Met Asp Pro Arg Gly Phe Asn Val Tyr Pro Ile
                85                  90                  95

Leu Ala Ala Thr Glu Gln Glu Lys Lys Tyr Pro Phe Leu Trp Arg Phe
            100                 105                 110

Trp His Asn Leu Pro Pro Lys Gly Ser Ile Gly Ile Phe Tyr His Ser
        115                 120                 125

Trp Tyr Thr His Val Leu Glu Asp Arg Leu Phe Gly Ile Glu Thr Asp
    130                 135                 140

Gly Ser Ile Pro Leu Leu Met Arg Asp Ile Asn Ala Phe Glu Arg Gln
145                 150                 155                 160

Leu Val Asp Asp Gly Val Ala Ile Ala Lys Phe Trp Ile His Leu Ser
                165                 170                 175

Gln Lys Glu Leu Lys Lys Arg Leu Lys Thr Tyr Ala Ser Asp Glu Leu
            180                 185                 190

Glu Ser Trp Arg Val Arg Pro Glu Asp Trp Gln Gln Ala Lys Glu Tyr
        195                 200                 205

Asp Arg Tyr Gly Thr Phe Ala Glu Glu Met Leu Thr Tyr Thr Ser Thr
    210                 215                 220

Gly His Ala Pro Trp Thr Leu Val Glu Gly Asp Cys Lys Arg Trp Ala
225                 230                 235                 240

Arg Val Lys Val Leu Ser Gln Ile Val Ala Val Ile Thr Gln Ala Leu
                245                 250                 255

Asp Arg Leu Arg Leu Pro Lys Thr Asp Ile Pro Ser Leu Pro Pro Gln
            260                 265                 270

Thr Glu Leu Gln Pro Thr Glu Pro Asp Phe Leu Gly Lys Ile Asp Leu
        275                 280                 285

Gly Leu His Leu Phe Lys Asp Asp Tyr Lys Gln Arg Leu Arg Glu Ala
    290                 295                 300

Gln Val Lys Leu Arg Glu Leu Gln Leu Gln Ile Phe Lys Lys Lys Val
305                 310                 315                 320

Pro Val Leu Val Leu Phe Glu Gly Trp Asp Ala Ala Gly Lys Gly Gly
                325                 330                 335

Ala Ile Lys Arg Leu Thr Asp Thr Leu Asp Pro Arg Ser Tyr Lys Val
            340                 345                 350

His Ala Phe Ser Ala Pro Thr Ser Glu Glu Leu Asn Tyr His Tyr Leu
        355                 360                 365

Trp Arg Phe Trp Arg Gln Ile Pro Ala Gln Gly Ser Ile Gly Ile Phe
    370                 375                 380

Asp Arg Ser Trp Tyr Gly Arg Val Leu Val Glu Arg Val Glu Gly Phe
385                 390                 395                 400

Ala Ser Glu Leu Glu Trp Arg Arg Ser Tyr Lys Glu Ile Asn Glu Phe
                405                 410                 415

Glu Ser Gln Leu Thr Ala Ser Gly Tyr Val Ile Val Lys Phe Trp Leu
            420                 425                 430

His Ile Ser Phe Glu Glu Gln Leu Lys Arg Phe Glu Asp Arg Lys Asn
        435                 440                 445

Asn Pro Phe Lys Ser Tyr Lys Leu Thr Asp Glu Asp Trp Arg Asn Arg
    450                 455                 460

Glu Lys Trp Pro Leu Tyr Tyr Val Ala Val Asn Gln Met Ile Ala Arg
465                 470                 475                 480

Thr Ser Thr Pro Tyr Ala Pro Trp Thr Ile Val Pro Gly Asn Asp Lys
                485                 490                 495
```

```
Tyr Tyr Ala Arg Val His Val Leu Glu Thr Val Ile His Ala Ile Glu
            500                 505                 510

Thr Glu Leu Lys Gln Arg Asp
        515
```

<210> SEQ ID NO 63
<211> LENGTH: 128
<212> TYPE: PRT
<213> ORGANISM: Cyanothece ATCC51142

<400> SEQUENCE: 63

```
Val Glu Pro Lys Thr Gly Lys Thr Leu Trp Tyr Leu Ile Pro Arg Val
1               5                   10                  15

Asn Asn Lys Trp Leu Ser Leu Val Tyr Glu Ala Phe Ala Glu Asp Val
            20                  25                  30

Gly Leu Asn Lys Asp Lys Ile Ile Phe Leu Val Glu Asp Asn Ala Gly
        35                  40                  45

Trp His Arg Ser Gln Lys Leu Lys Ile Pro Asn Gly Ile Ile Val Glu
    50                  55                  60

Phe Leu Pro Ala Tyr Ser Pro Glu Leu Gln Pro Ala Glu Arg Leu Trp
65                  70                  75                  80

Thr Leu Val Asp Glu Pro Leu Val Asn Glu Tyr Phe Glu Thr Ile Glu
                85                  90                  95

Glu Ile Glu Asp Ile Leu Ala Ile Arg Cys Cys Leu Leu Gln Asn Met
            100                 105                 110

Thr Glu Glu Ile Lys Asn Leu Thr Asn Tyr His Trp Leu Lys Tyr Ser
        115                 120                 125
```

<210> SEQ ID NO 64
<211> LENGTH: 406
<212> TYPE: PRT
<213> ORGANISM: Cyanothece ATCC51142

<400> SEQUENCE: 64

```
Met Ala Lys Gly Phe Ala Asp Gln Lys Gln Ser Ser Lys Lys Lys Lys
1               5                   10                  15

Glu Lys Gly Asn Ile Ala Ser Ile Asp Glu Ile Gln Asn Asn Leu Leu
            20                  25                  30

Gly Tyr Val Lys Glu Ile Glu Asp Pro Arg Val Gln Arg Ser Lys Lys
        35                  40                  45

His Leu Leu Lys Asp Val Leu Ala Ile Ala Ile Leu Ala Val Ile Ala
    50                  55                  60

Gly Ser Gln Gly Trp Glu Asp Met Glu Asn Tyr Gly Ile Ala Lys Gln
65                  70                  75                  80

Glu Trp Leu Ser Glu Phe Leu Glu Leu Pro His Gly Ile Pro Ser Asp
                85                  90                  95

Asp Thr Phe Arg Arg Val Phe Glu Arg Ile Asp Pro Glu Ser Leu Gln
            100                 105                 110

Lys Cys Leu Gln Lys Trp Val Gln Ser Ile Met Asn Ser Ile Gln Gly
        115                 120                 125

Glu Ile Ile Pro Ile Asp Gly Lys Thr Leu Arg Gly Ser Tyr Asp Arg
    130                 135                 140

Asn Ala Gly Gln Cys Ala Leu His Thr Val Thr Ala Trp Ala Ser Gln
145                 150                 155                 160

Gln Ser Leu Val Leu Gly Gln Val Lys Val Glu Asn Tyr Ser Asn Glu
                165                 170                 175
```

```
Ile Thr Ala Ile Pro Ala Leu Leu Glu Leu Leu Asp Ile Thr Gly Ser
            180                185                190

Ile Ile Thr Ile Asp Ala Met Gly Thr Gln Thr Ser Ile Ile Gln Gln
        195                200                205

Ile Cys Arg Gln Lys Ala Asp Tyr Ile Val Thr Leu Lys Ala Asn His
    210                215                220

Pro Thr Leu Phe Ser Gln Val Lys Gln Trp Phe Thr Asp Thr Gln Asn
225                230                235                240

Asn Gly Trp Asp Gly Ile Glu His Asp Tyr Tyr Lys Ser Val Thr Lys
                245                250                255

Gly His His Arg Thr Glu Lys Arg Tyr Val Trp Ala Ile Pro Val Ala
            260                265                270

Ala Met Gly Glu Leu Tyr Gln Gln Gln Gln Trp His Gly Leu Gln Thr
        275                280                285

Ile Val Val Val Glu Arg Ile Arg His Leu Trp Asn Lys Thr Thr His
    290                295                300

Asp Ile Gln Phe Tyr Leu Thr Ser Leu Pro Pro Asn Ala Gln Phe Leu
305                310                315                320

Cys His Ala Ile Arg Thr His Trp Ser Ile Glu Asn Asn Leu His Trp
                325                330                335

Thr Leu Asp Val Thr Phe Ser Glu Asp Gln Cys Arg Ile Arg Ser Glu
            340                345                350

Tyr Ser Pro Gln Asn Phe Ala Leu Leu Arg Arg Leu Ala Leu Asn Val
        355                360                365

Leu His Gln Glu Lys Thr Phe Lys Arg Ser Leu Arg Gln Lys Met Lys
    370                375                380

Gln Ala Ala Met Asn Asn Asn Tyr Met Met Thr Val Leu Asn Ser Phe
385                390                395                400

Cys Gln Ala Asp Phe Arg
                405


<210> SEQ ID NO 65
<211> LENGTH: 67
<212> TYPE: PRT
<213> ORGANISM: Cyanothece ATCC51142

<400> SEQUENCE: 65

Met Thr Thr Ile Asn Tyr Thr Pro Asp Pro Glu Lys Lys Ala Gln Leu
1               5                   10                  15

Ser Gln Glu Gln Leu Ser Arg Leu Glu Glu Leu Ser Asp Glu Asp Ile
            20                  25                  30

Asp Tyr Ser Asp Ile Pro Glu Leu Asp Asp Asn Phe Trp Glu Asn Ala
        35                  40                  45

Glu Ile Val Asn Thr Asp Val Thr Gln Asn Thr Val Ser Ser Thr Leu
    50                  55                  60

Gly Asn Phe
65


<210> SEQ ID NO 66
<211> LENGTH: 61
<212> TYPE: DNA
<213> ORGANISM: Artificial Sequence
<220> FEATURE:
<223> OTHER INFORMATION: Synthetic sequence

<400> SEQUENCE: 66
```

-continued

```
cggggatccc acgtacaacg acacctagac cacgtgttcc taggctgttt cctggtggga     60

t                                                                     61


<210> SEQ ID NO 67
<211> LENGTH: 22
<212> TYPE: DNA
<213> ORGANISM: Artificial Sequence
<220> FEATURE:
<223> OTHER INFORMATION: Synthetic Primer

<400> SEQUENCE: 67

ccagtcacga cgttgtaaaa cg                                              22


<210> SEQ ID NO 68
<211> LENGTH: 22
<212> TYPE: DNA
<213> ORGANISM: Artificial Sequence
<220> FEATURE:
<223> OTHER INFORMATION: Synthetic Primer

<400> SEQUENCE: 68

cgccaagcta tttaggtgag ac                                              22
```